US012565519B2

(12) United States Patent　　　　　(10) Patent No.:　US 12,565,519 B2
Ercek et al.　　　　　　　　　　　　　(45) Date of Patent:　　Mar. 3, 2026

(54) RECOMBINANT STRAINS AND MEDIUM FORMULATION FOR ENHANCING SECRETION TITER USING A TYPE III SECRETION SYSTEM

(71) Applicant: Northwestern University, Evanston, IL (US)

(72) Inventors: Danielle Tullman Ercek, Wilmotte, IL (US); Lisa A. Burdette, Evanston, IL (US); Han Teng Wong, Evanston, IL (US)

(73) Assignee: Northwestern University, Evanston, IL (US)

( * ) Notice: Subject to any disclaimer, the term of this patent is extended or adjusted under 35 U.S.C. 154(b) by 1022 days.

(21) Appl. No.: 17/310,094

(22) PCT Filed: Jan. 16, 2020

(86) PCT No.: PCT/US2020/013963
　　§ 371 (c)(1),
　　(2) Date: Jul. 15, 2021

(87) PCT Pub. No.: WO2020/150533
　　PCT Pub. Date: Jul. 23, 2020

(65) Prior Publication Data
US 2022/0064227 A1　　　Mar. 3, 2022

Related U.S. Application Data

(60) Provisional application No. 62/793,226, filed on Jan. 16, 2019.

(51) Int. Cl.
　　*C07K 14/255*　　　(2006.01)
　　*C12N 1/20*　　　　(2006.01)
　　*C12N 15/74*　　　(2006.01)
　　*C12P 21/02*　　　(2006.01)
(52) U.S. Cl.
　　CPC ............. *C07K 14/255* (2013.01); *C12N 1/20* (2013.01); *C12N 15/74* (2013.01); *C12P 21/02* (2013.01)
(58) Field of Classification Search
　　CPC .... C12R 2001/42; C07K 14/255; C12N 1/20; C12N 15/74; C12P 21/02
　　See application file for complete search history.

(56) References Cited

U.S. PATENT DOCUMENTS 6,664,386 B1 *　12/2003　Galan ..................... C12N 15/74
　　　　　　　　　　　　　　　　　　　　　435/69.3
7,396,664 B2　　7/2008　Daly et al.
2012/0231502 A1　　9/2012　Hamilton et al.

FOREIGN PATENT DOCUMENTS

WO　　　2020150533 A1　　7/2020

OTHER PUBLICATIONS

Baxter, M. Aaron, et al. "HilE interacts with HilD and negatively regulates hilA transcription and expression of the *Salmonella enterica* serovar Typhimurium invasive phenotype." Infection and immunity 71.3 (2003): 1295-1305. (Year: 2003).*
Mcclelland, M., Sanderson, K., Spieth, J. et al. Complete genome sequence of *Salmonella enterica* serovar Typhimurium LT2. Nature 413, 852-856 (2001). https://doi.org/10.1038/35101614 (Year: 2001).*
El Mouali Y et al. CRP-CAMP mediates silencing of *Salmonella virulence* at the post-transcriptional level. PLoS Genetics. 2018. 14/(6):e1007401. (Year: 2018).*
Singh RK et al. Protein Engineering Approaches in the Post-Genomic Era. 2017, 18, 1-11. (Year: 2017).*
Zhang M et al. Propagated Perturbations from a Peripheral Mutation Show Interactions Supporting WW Domain Thermostability. 2018. Structure. 26, 1474-1485. (Year: 2018).*
Altschul, S. F. et al. Basic Local Alignment Search Tool. J. Mol. Biol. 1990;215:403 410.
Altschul et al., Gapped BLAST and PSI-BLAST: a new generation of protein database search programs. Nucl. Acids Res. 1997;25: 3389-3402.
Anne J, Maldonado B, Van Impe J, Van Mellaert L, Bernaerts K. Recombinant protein production and streptomycetes. Journal of Biotechnology. 2012;158:159-67.
Anne J, Vrancken K, Van Mellaert L, Van Impe J, Bernaerts K. Protein secretion biotechnology in Gram-positive bacteria with special emphasis on Streptomyces lividans. Biochim Biophys Acta. 2014; 1843:1750-61.
Azam A, Li C, Metcalf KJ, Tullman-Ercek D. Type III secretion as a generalizable strategy for the production of full-length biopolymer-forming proteins. Biotechnol Bioeng. 2015.
Baxter MA, Fahlen TF, Wilson RL, Jones BD. HilE Interacts with HilD and Negatively Regulates hilA Transcription and Expression of the *Salmonella enterica Serovar* Typhimurium Invasive Pheno-type. Infect Immun. 2003;71:1295-305.
Baxter MA, Jones BD. Two-Component Regulators Control hilA Expression by Controlling fimZ and hilE Expression within *Salmonella enterica* Serovar Typhimurium. Infect Immun. 2015;83:978-85.
Berkowitz D, Hushon JM, Whitfield HJ, Roth J, Ames BN. Procedure for identifying nonsense mutations. J Bacteriol. 1968;96:215-20.

(Continued)

*Primary Examiner* — Paul J Holland
(74) *Attorney, Agent, or Firm* — Quarles & Brady LLP

(57) ABSTRACT

The present disclosure provides a recombinant *Salmonella* strain having a Type III secretion system (T3SS) comprising mutation which enhance protein expression and production. Additionally, methods and kits for using the recombinant *Salmonella* strain for producing a protein of interest are provided. Additionally, an optimized medium that increases protein expression in a *Salmonella* strain having a Type III secretion system (T3SS) is provided.

22 Claims, 33 Drawing Sheets
Specification includes a Sequence Listing.

(56)　　　　　References Cited

OTHER PUBLICATIONS

Buchholz K, Collins J. The roots—a short history of industrial microbiology and biotechnology. Appl Microbiol Biotechnol. 2013;97:3747-62.

Chen, Xiaoying et al. "Fusion protein linkers: property, design and functionality" Advanced drug delivery reviews vol. 65, 10 (2012): 1357-69.

Chubiz, J. E. C., Golubeva, Y. A., Lin, D., Miller, L. D. & Slauch, J. M. FliZ Regulates Expression of the *Salmonella* Pathogenicity Island 1 Invasion Locus by Controlling HilD Protein Activity in *Salmonella enterica Serovar* Typhimurium. J. Bacteriol. 192, 6261-6270 (2010).

Clark EDB. Protein refolding for industrial processes. Current Opinion in Biotechnology. 2001; 12:202-7.

Deng W, Marshall NC, Rowland JL, McCoy JM, Worrall LJ, Santos AS, et al. Assembly, structure, function and regulation of type III secretion systems. Nature Reviews Microbiology. 2017;15:323-37.

Ellermeier CD, Ellermeier JR, Slauch JM. HilD, HilC and RtsA constitute a feed forward loop that controls expression of the SPI1 type three secretion system regulator hilA in *Salmonella enterica* serovar Typhimurium. Molecular Microbiology. 2005;57:691-705.

Ellermeier JR, Slauch JM. Adaptation to the host environment: regulation of the SPI1 type III secretion system in *Salmonella enterica* serovar Typhimurium. Current Opinion in Microbiology. 2007;10:24-9.

Ellermeier, J. R. & Slauch, J. M. Fur Regulates Expression of the *Salmonella* Pathogenicity Island 1 Type III Secretion System through HilD. J. Bacteriol. 190, 476 486 (2008).

Engler C, Kandzia R, Marillonnet S. A One Pot, One Step, Precision Cloning Method with High Throughput Capability. PLoS One. 2008;3:e3647.

Erhardt M, Dersch P. Regulatory principles governing Salmonella and Yersinia virulence. *Salmonella*. 2015;949.

Galan JE, Lara-Tejero M, Marlovits TC, Wagner S. Bacterial Type III Secretion Systems: Specialized Nanomachines for Protein Delivery into Target Cells. Annual Review of Microbiology. 2014;68:415-38.

Glasgow AA, Wong HT, Tullman-Ercek D. A Secretion-Amplification Role for *Salmonella enterica* Translocon Protein SipD. ACS Synth Biol. 2017;6:1006-15.

Golubeva YA, Sadik AY, Ellermeier JR, Slauch JM. Integrating Global Regulatory Input Into the *Salmonella* Pathogenicity Island 1 Type III Secretion System. Genetics. 2012;190:79-90.

Good NE, Winget GD, Winter W, Connolly TN, Izawa S, Singh RM. Hydrogen ion buffers for biological research. Biochemistry. 1966;5:467-77.

Grenz, J. R., Chubiz, J. E. C., Thaprawat, P. & Slauch, J. M. HilE Regulates HilD by Blocking DNA Binding in *Salmonella enterica* Serovar Typhimurium. J. Bacteriol. 200, (2018).

Hartman EC, Jakobson CM, Favor AH, Lobba MJ, Álvarez-Benedicto E, Francis MB, et al. Quantitative characterization of all single amino acid variants of a viral capsid-based drug delivery vehicle. Nature Communications. 2018;9:1385.

Hu J, Worrall LJ, Hong C, Vuckovic M, Atkinson CE, Caveney N, et al. Cryo-EM analysis of the T3S injectisome reveals the structure of the needle and open secretin. Nature Communications. 2018;9:1-11.

Karlin and Altschul, 1990, Proc. Natl. Acad. Sci. USA 87: 2267-2268.

Kim E, Jakobson CM, Tullman-Ercek D. Engineering transcriptional regulation to control Pdu bacterial microcompartment formation. PLoS One. 2014. vol. 9, No. 11, pp. 1-14.

Kim, K., Golubeva, Y. A., Vanderpool, C. K. & Slauch, J. M. Oxygen-dependent regulation of SPI1 type three secretion system by small RNAs in *Salmonella enterica* serovar Typhimurium. Mol. Microbiol. 111, 570-587 (2019).

Kim, K., Palmer, A. D., Vanderpool, C. K. & Slauch, J. M. The Small RNA PinT Contributes to PhoP-Mediated Regulation of the

*Salmonella* Pathogenicity Island 1 Type III Secretion System in *Salmonella enterica* Serovar Typhimurium. J. Bacteriol. 201, (2019).

Laemmli UK. Cleavage of Structural Proteins during the Assembly of the Head of Bacteriophage T4. Nature. 1970;227:680-5.

Leysath CE, Monzingo AF, Maynard JA, Barnett J, Georgiou G, Iverson BL, et al. Crystal Structure of the Engineered Neutralizing Antibody M18 Complexed to Domain 4 of the Anthrax Protective Antigen. Journal of Molecular Biology. 2009;387:680-93.

López-Garrido, J., Puerta-Fernandez, E. Casadesús, J. A eukaryotic-like 3' untranslated region in *Salmonella enterica* hilD mRNA. Nucleic Acids Res. 42, 5894-5906 (2014).

Loquet A, Sgourakis NG, Gupta R, Giller K, Riedel D, Goosmann C, et al. Atomic model of the type III secretion system needle. Nature. 2012;486:276-9.

Maynard JA, Maassen CBM, Leppla SH, Brasky K, Patterson JL, Iverson BL, et al. Protection against anthrax toxin by recombinant antibody fragments correlates with antigen affinity. Nature Biotechnology. 2002;20:597-601.

Metcalf KJ, Bevington JL, Rosales SL, Burdette LA, Valdivia E, Tullman-Ercek D. Proteins adopt functionally active conformations after type III secretion. Microbial Cell Factories. 2016;15:213.

Metcalf KJ, Finnerty C, Azam A, Valdivia E, Tullman-Ercek D. Using Transcriptional Control To Increase Titers of Secreted Heterologous Proteins by the Type III Secretion System. Applied and Environmental Microbiology. 2014;80:5927-34.

Metcalf KJ. Engineering heterologous protein secretion for improved production. University of California, Berkeley; 2016.

Mizusaki H, Takaya A, Yamamoto T, Aizawa S-I. Signal Pathway in Salt-Activated Expression of the *Salmonella* Pathogenicity Island 1 Type Ill Secretion System in *Salmonella enterica* Serovar Typhimurium. J Bacteriol. 2008;190:4624-31.

Neidhardt FC, Bloch PL, Smith DF. Culture Medium for Enterobacteria Culture Medium for Enterobacteria. 1974;119.

Petrone BL, Stringer AM, Wade JT. Identification of HilD-Regulated Genes in *Salmonella enterica* Serovar Typhimurium. J Bacteriol. 2014;196:1094-101.

Reed B, Chen R. Biotechnological applications of bacterial protein secretion: from therapeutics to biofuel production. Research in Microbiology. 2013;164:675-82.

Rosano GL, Ceccarelli EA. Recombinant protein expression in *Escherichia coli*: advances and challenges. Front Microbiol. 2014;5:172.

Song M, Sukovich DJ, Ciccarelli L, Mayr J, Fernandez-Rodriguez J, Mirsky EA, et al. Control of type III protein secretion using a minimal genetic system. Nature Communications. 2017;8:14737.

Studier FW. Protein production by auto-induction in high density shaking cultures. Protein Expr Purif. 2005;41:207-34.

Sturm A, Heinemann M, Arnoldini M, Benecke A, Ackermann M, Benz M, et al. The Cost of Virulence: Retarded Growth of *Salmonella typhimurium* Cells Expressing Type III Secretion System 1. PLOS Pathog. 2011;7:e1002143.

Teplitski M, Goodier RI, Ahmer BMM. Catabolite repression of the SirA regulatory cascade in *Salmonella enterica*. International Journal of Medical Microbiology. 2006;296:449-66.

Thomason LC, Sawitzke JA, Li X, Costantino N, Court DL. Recombineering: Genetic Engineering in Bacteria Using Homologous Recombination. Current Protocols in Molecular Biology. 2014;106:1.16.1-1.16.39.

Widmaier DM, Tullman-Ercek D, Mirsky EA, Hill R, Govindarajan S, Minshull J, et al. Engineering the *Salmonella* type II secretion system to export spider silk monomers. Molecular Systems Biology. 2009;5:309.

Widmaier DM, Voigt CA. Quantification of the physiochemical constraints on the export of spider silk proteins by *Salmonella* type III secretion. Microbial Cell Factories. 2010;9:78.

International Search Report and Written Opinion issued in corresponding PCT Application No. PCT/US2020/013963, mailed Apr. 9, 2020.

Extended European Search Report issued in corresponding EP Application No. 20742129.8, mailed Dec. 19, 2022.

* cited by examiner

FIGS. 2A-2C
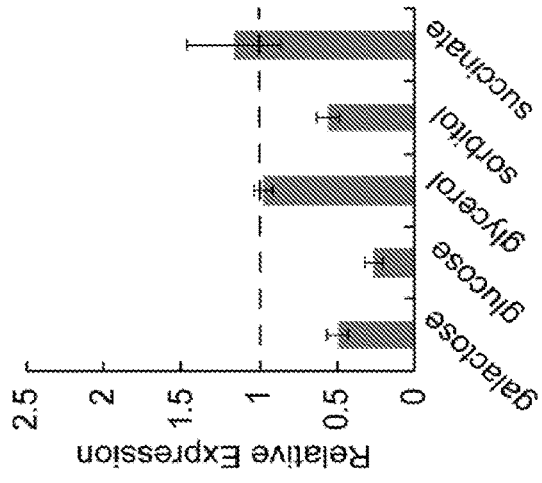
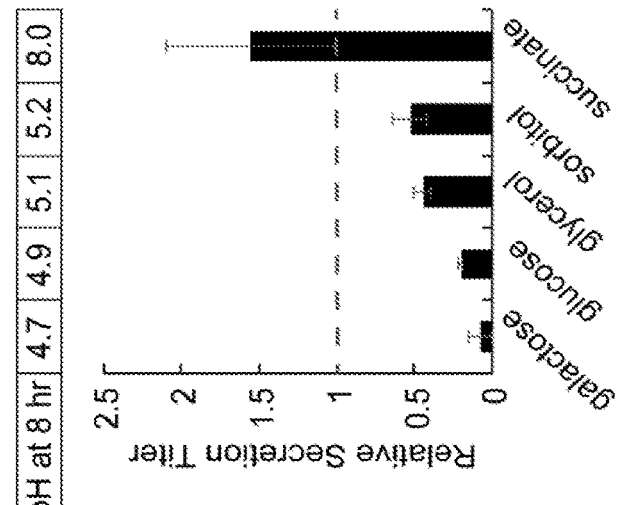
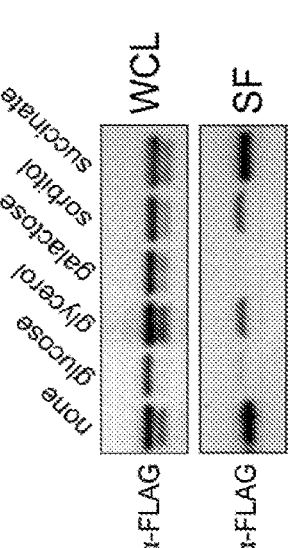

FIGS. 14A-14B
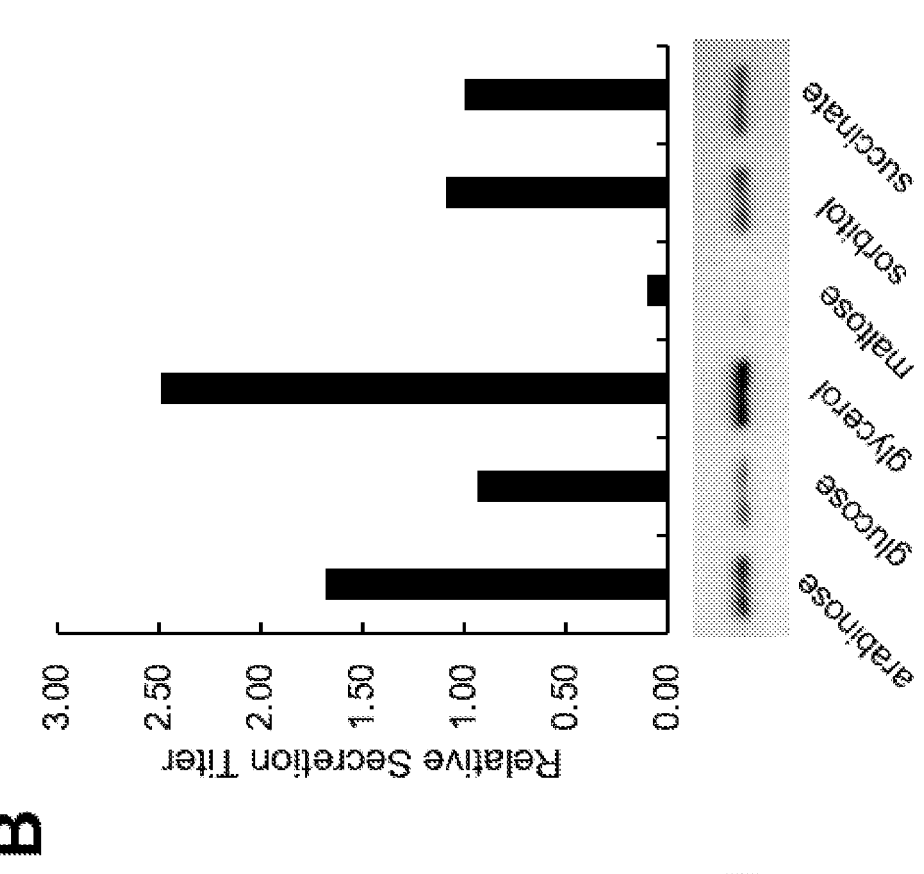
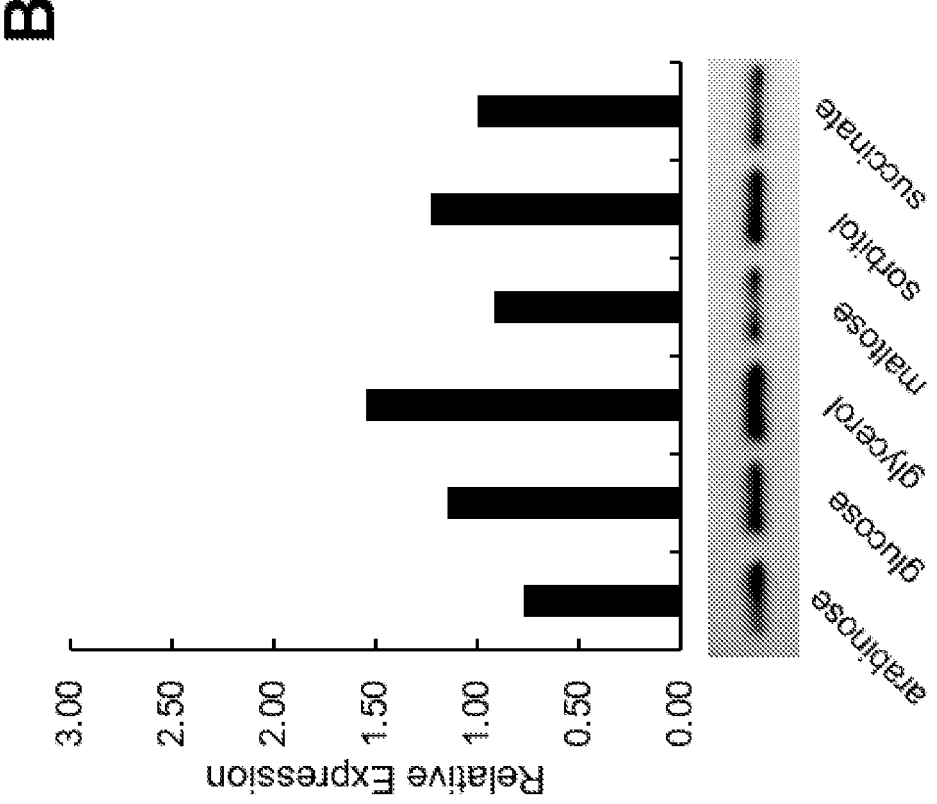

◇ 0 µM IPTG
◆ 1 µM IPTG
◆ 5 µM IPTG
◆ 10 µM IPTG
◆ 50 µM IPTG
◆ 100 µM IPTG
◆ 500 µM IPTG
◆ 1000 µM IPTG d pHilD
pHilA
pInvF
pSicA c a b

RECOMBINANT STRAINS AND MEDIUM FORMULATION FOR ENHANCING SECRETION TITER USING A TYPE III SECRETION SYSTEM

CROSS-REFERENCE TO RELATED APPLICATIONS

This application represents the U.S. national s age entry of International Patent Application Serial No. PCT/US2020/013963, filed on Jan. 16, 2020, which claims priority to U.S. Provisional Application No. 62/793,226 filed on Jan. 16, 2019, the contents of which are incorporated by reference in their entirety.

STATEMENT REGARDING FEDERALLY SPONSORED RESEARCH

This invention was made with government support under NSF1706125 awarded by National Science Foundation. The government has certain rights in the invention.

BACKGROUND OF THE INVENTION

The field of the invention is related to recombinant bacterial strains and modified medium for improving bacterial protein production.

The ever-increasing diversity of commercial protein products coupled with the high cost of developing these products is driving engineering efforts to develop low-cost, easy-to-manipulate production systems. Bacterial hosts are robust, genetically tractable, and inexpensive to cultivate, but traditional intracellular expression strategies present several challenges [1,2]. Products must be recovered from a complex lysate mixture, which requires several downstream purification steps. Further, intracellular overexpression of heterologous proteins often causes aggregation in insoluble inclusion bodies [3]. Initial product purity is often higher in inclusion bodies, but resolubilization and refolding processes must be developed for each product. Finally, many heterologous proteins, including those biomaterials such as spider silk, are difficult to express at high levels because they are toxic to the host [4]. Engineering bacteria to secrete heterologous proteins into the extracellular space eliminates these constraints.

The type III secretion system (T3SS), is a promising platform for protein secretion in bacteria as it secretes proteins from the cytoplasm to the extracellular space in a single step [5,6]. It is not required for cell viability, which facilitates engineering efforts and allows it to be used solely for heterologous cargo. The T3SS is a multimeric protein needle complex that spans the inner and outer membranes of the bacterial cell. It is well-characterized and exists in two classes, the injectisome and the flagellum. The *Salmonella* Pathogenicity Island I (SPI-1) T3SS of *Salmonella enterica* Typhimurium is an injectisome that has been successfully engineered to secrete high titers of several heterologous proteins, including spider silk monomers, antimicrobial peptides, and scFvs [4,7,8]. Despite these successes, achieving high titers requires synthetic overexpression of a master regulator, HilA, from a plasmid. Secretion titers remain below 1 g/L even with hilA overexpression, and secretion system function is sensitive to environmental conditions, including those favored for industrial protein production.

Therefore, there is need for better systems for promoting high titers of heterologous protein which are of high purity. The present invention is directed to meeting this and other needs.

SUMMARY OF THE INVENTION

Certain embodiments of the present disclosure substantially overcome the aforementioned drawbacks by providing a novel recombinant bacterial strain and methods of use to produce secrete protein at high titers and purity.

In one aspect, the present disclosure provides a recombinant *Salmonella* strain (cell) having a Type III secretion system (T3SS) comprising (a) a deletion or inactivation of hilE; or (b) insertion of a tag protein at the beginning of the hill 3'UTR suitable to increase hilD expression in the strain; or (c) both (a) and (b). In some aspects, the recombinant *Salmonella* strain has at least 2 fold increased secretion titer of a heterologous protein of interest by the Type III secretion system as compared to a non-recombinant *Salmonella* strain having a Type III secretion system.

In another aspect, the present disclosure provides an in vitro method of making a heterologous protein of interest, the method comprising: (a) expressing a heterologous protein of interest in a recombinant *Salmonella* cell having a Type III secretion system (T3SS) comprising (a) a deletion or inactivation of hilE; or (b) insertion of a protein coding sequence at the beginning of the hill 3'UTR suitable to increase hilD expression in the strain; or (c) both (a) and (b), wherein the protein of interest is fused to a targeting polypeptide that directs the protein to the Type III secretion system (T3SS), and wherein the protein of interest is secreted into medium in which the *Salmonella* cells are suspended.

In yet another aspect, the present disclosure provides an in vitro culture comprising: (a) a recombinant *Salmonella* strain described herein; and (b) culture medium for increasing protein secretion comprising: about 10 g/L peptone, about 5 g/L yeast extract, about 0.4% w/v glycerol or glucose, and about 40 mM or 90 mM potassium phosphate pH 7.4. In a preferred embodiment, the culture medium further comprises about 150 nM to about 210 nM NaCl. In another aspect, the culture medium is chemically defined medium comprising about 0.4% w/v glycerol or glucose, and about 40 mM or 90 mM potassium phosphate pH 7.4, and about 150 nM to about 210 nM NaCl (for example, medium as described in Table 11).

In another aspect, the present disclosure provides a kit for making a heterologous protein of interest comprising a recombinant *Salmonella* strain described herein and instructions for use.

The foregoing and other aspects and advantages of the invention will appear from the following description. In the description, reference is made to the accompanying drawings which form a part hereof, and in which there is shown by way of illustration at least one preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIGS. 2A-2C. Non-ionic carbon sources effect on titer. Relative bulk secretion titer (i), expression (ii), and representative western blots (iii) of SptP-DH-2×FLAG-6×His. Error bars represent one standard deviation. Expression and secretion titer were normalized to LB-L with no carbon source using densitometry measurements on western blots. Western blots are representative of three biological replicates. The pH of the secreted fraction was recorded at the end of the experiment.

FIGS. 8A-8B. Sugars and buffers have a synergistic effect on expression and secretion titer. (A) Relative bulk secretion titer (left) and expression (right) of SptP-DH-2×FLAG-6× His secreted in media containing 10 g/L tryptone, 5 g/L yeast extract, and the additives listed in Table 7. Bulk expression and secretion titer were normalized to LB-L with no additives (dotted lines). (B) Western blots are representative of three biological replicates. Samples were diluted to fall within the linear range of the LB-L signal. Boxed bands are from the same blot but were rearranged for clarity. "WCL" is whole culture lysate and "SF" is secreted fraction.

FIGS. 14A-14B. Relative expression and secretion titer in NCE with various carbon sources. Expression (A) and secretion titer (B) of SptP-Bla-2×FLAG-6×His at 8 hours were measured via semi-quantitative western blotting and normalized to succinate. 1×EZ Supplement was included in NCE. All carbon sources were 0.4% w/v. $P_{lacUV5}$ hilA induction facilitated T3SS and SptP-Bla-2×FLAG-6×His expression. Data represents one biological replicate.

DETAILED DESCRIPTION OF THE INVENTION

Figures 1A, 1B, 1C:
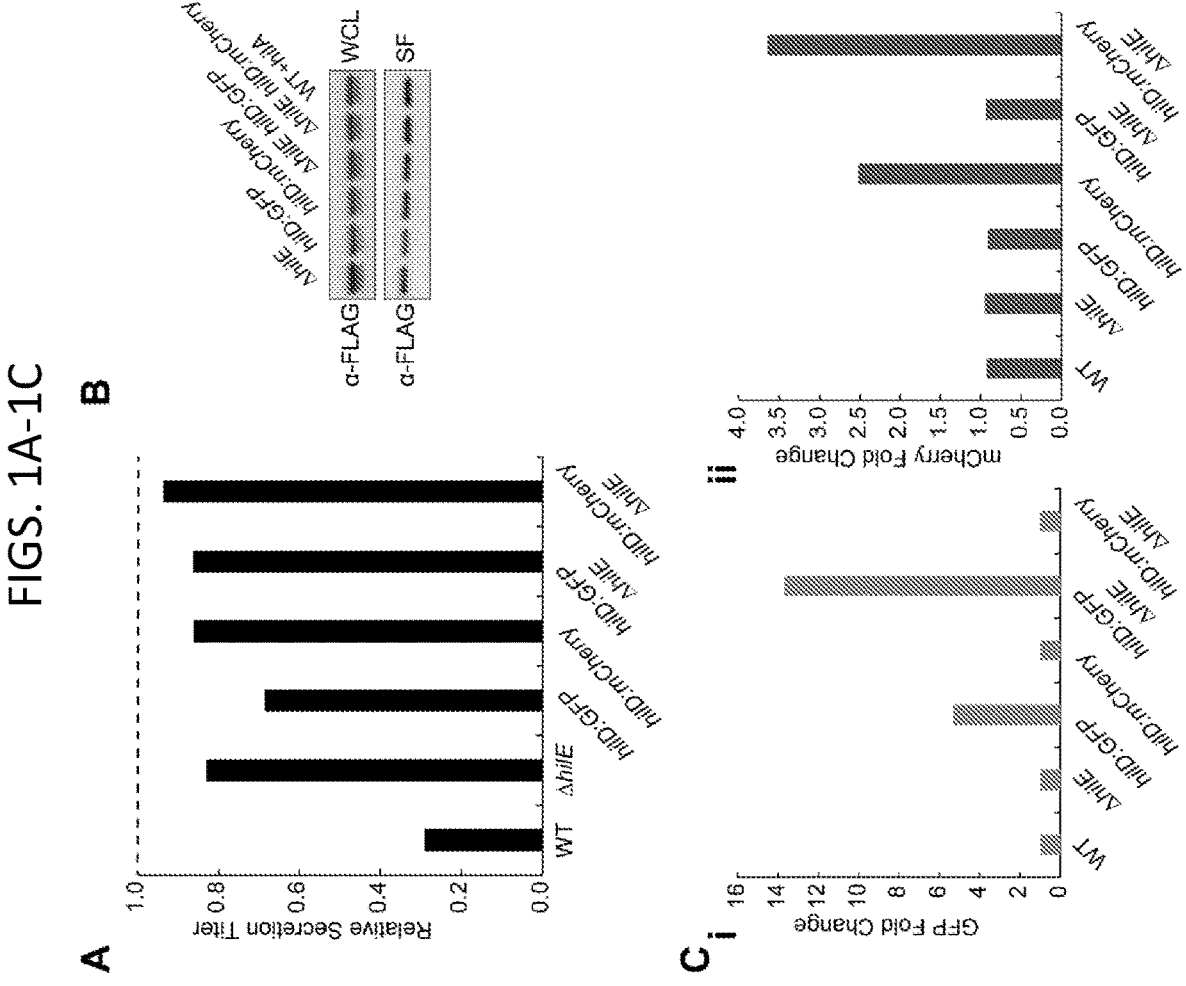
FIGS. 1A-1C. Secretion titer and transcriptional activity of genomically modified strains compared to the state-of-the-art system. Densitometry and fluorescence values were normalized to ASTE13 secretion in LBL with hilA overexpression. Results represent a single biological replicate. (A) Relative secretion titer of DH by densitometry. ASTE13 in LBL with hilA overexpression is represented as a dashed line. (B) Western Blot analysis of data in (A). (C) Fold change of fluorescence geometric mean for GFP and mCherry according to flow cytometry.

The present invention has been described in terms of one or more preferred embodiments, and it should be appreciated that many equivalents, alternatives, variations, and modifications, aside from those expressly stated, are possible and within the scope of the invention. Before the present invention is described, it is understood that this invention is not limited to the particular methodology, protocols, and reagents described, as these may vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

The present disclosure provides a Gram-negative bacterial recombinant strain, specifically a modified *Salmonella* strain, that is capable of increased protein yield and secretion capacity over the prior methods. The modified recombinant *Salmonella* strain can additionally comprise deletion or reduction of one or more pathogenicity or virulence genes (e.g., one or more pathogenicity islands) to provide a non-pathogenic strain capable of producing secreted proteins at higher yields. In one embodiment, increasing expression of the T3SS master regulator HilD via genomic engineering yielded a strain with enhanced protein expression and secretion capacity without the need for synthetic overexpression of HilA. Further, an optimized defined growth media was developed containing glycerol and a high concentration of phosphate buffer which further increases protein secretion titer about twofold. Combining the enhanced strain and the optimized defined medium has a more than additive effect on protein secretion titer, increasing secretion titer fourfold and creating an optimal secretion system for heterologous protein production in Gram-negative bacteria. The protein is secreted into the medium and found to have high purity, providing a system that is able to produce large quantities of a protein of interest with less processing steps.

Recombinant proteins are central to nearly every aspect of our daily lives. Industrial enzymes, biomaterials, and protein therapeutics comprise billion dollar markets. Currently, the least expensive method to manufacture these proteins is using living organisms as production platforms. Bacteria are an ideal choice because they are robust, easy to manipulate, and inexpensive to culture at large scale. Traditional bacterial production processes require recovery of the product from inside the organism, however, which complicates product purification and increases production costs. Secreting the product outside of the cell retains the benefits of bacterial protein expression while simplifying product purification. Broad efforts to engineer protein secretion in bacteria have yielded diverse options, but many are limited by low titers and poorly characterized secretion mechanisms.

The present disclosure provides a platform for heterologous protein secretion to the extracellular environment in an organism that secretes few other proteins. The advancements described here include an enhanced strain that streamlines secretion activation and an optimized growth medium that promotes consistently high secretion titers. The recombinant strain, methods, and kits provide protein production in bacteria at high titer and purity, which eliminates the extensive downstream processing required of non-secretion based bacterial production systems. In so doing, costs for R&D and production will be lowered substantially. The recombinant strain, kits and methods described herein further provide secreted bacterial protein production using a mechanism that bypasses the periplasm and so yields purer product requiring less downstream steps (saving money for the process but also reducing development costs and time).

In one embodiment, the present invention provides a recombinant *Salmonella* strain having a Type III secretion system (T3SS) comprising (a) a deletion or inactivation of hilE; or (b) insertion of a protein coding sequence at the beginning of the hill 3'UTR suitable to increase hilD expression in the strain; or (c) both (a) and (b). In a preferred embodiment, the recombinant *Salmonella* strain comprises (a) a deletion or inactivation of hilE (e.g., knockout of hilE) and (b) insertion of a tag protein sequence (e.g., B-barrel fluorescent protein) at the beginning of the hilD 3'UTR suitable to increase hilD expression in the strain. The recombinant *Salmonella* strain is capable of increased protein expression and production of a protein of interest. The recombinant *Salmonella* strain, in some embodiments, may further comprise a vector encoding the protein of interest.

In some embodiments, the modified *Salmonella* strain provides an increase in titer of the produced protein. The increased titer is relative to the same unmodified strain and in non-optimized media. [

As used herein, the term "*Salmonella* strain" can be used interchangeable with the term "*Salmonella* cell."

In one embodiment, the present invention provides a recombinant *Salmonella* strain having a Type III secretion system (T3SS) comprising (a) a deletion or inactivation of hilE. In the Examples, the inventors demonstrate that hilE knock out increased the secretion titer by 3-fold compared to the wild type strain without hilA overexpression (see para [0078] and FIG. 1A). Notably, the inventors targeted this gene because HilE was known to reduce hilA activation by binding to and negatively regulating HilD. Suitable methods of deletion or inactivation of hilE gene are known in the art. For example, the strain may contain a knockout of the hilE gene, wherein all or part of the hilE gene is removed or disrupted by insertion of non-native sequence. Knockouts may be generated using any known method of genetic engineering, including, without limitation, recombineering and nuclease mediated genome editing (e.g., CRISPR/Cas, and λ-Red-mediated recombination, among others). Alternatively, hilE gene expression may be reduced or eliminated at the RNA level using methods such as anti-sense RNA or CRISPR-based silencing (e.g., CRISPRi). In the Examples, HilE knock out strains (ΔhilE) were generated using recombineering (see para [0078]). Briefly, "recombineering" is a molecular biology technique in which PCR products and synthetic oligonucleotides are supplied as substrates, and bacteriophage-derived recombination proteins are used to recombine these oligonucleotides with homologous sites in the genome (Curr Protoc Mol Biol. (2014) 106:1.16.1-39). For example, the primers listed in Table 2 were used to generate hilE knock out strains and strains with an insertion in the hill 3'UTR (as indicated) using this method.

In another embodiment, the present invention provides a recombinant *Salmonella* strain having a Type III secretion system (T3SS) comprising (b) insertion of a tag protein at the beginning of the hilD 3'UTR suitable to increase HilD expression in the strain. Previous studies had demonstrated that the hill 3'UTR is a target for hilD mRNA degradation by the degradosome, and that eliminating a portion of the hilD 3' UTR increases transcript stability (Nucleic Acids Res. (2014) 42(9):5894-906). However, the inventors discovered that the hilD transcript could also be stabilized by inserting an exogenous protein coding sequence into the beginning of the 3' UTR. Suitable methods of inserting a non-native nucleotide sequence into a specific genomic site are known in the art (e.g., the genetic engineering methods discussed in the previous paragraph). Suitable protein coding sequences include any sequences that are able, when inserted in the hill 3'UTR, to increase hilD expression in the strain. In the Examples, the inventors found that inserting the β-barrel fluorescent proteins green fluorescent protein (GFP) and mCherry at the start of the hill 3'UTR (i.e., immediately after the coding sequence of hilD) and leaving the 3' UTR otherwise intact increased the secretion titer by 2.4-fold compared to the wild type strain without hilA overexpression (see para and FIG. 1A). Thus, in some embodiments, the protein coding sequence encodes a B-barrel protein, preferably a β-barrel fluorescent protein. However, one skilled in the art would be able to determine other suitable protein coding sequences. Protein coding sequences that can be inserted are known in the art and can include any full-length protein coding sequence that can be inserted between the hill coding sequence and the hill 3'UTR, which can increase protein secretion titer relative to an unmodified secretory system. Suitable protein coding insertions are demonstrated in FIG. 24. Any protein coding sequence is contemplated that is capable of being inserted allowing the 3'UTR to be left intact, and the protein coding sequence should be inserted immediately after the hill coding sequence and immediately before the 3'UTR (i.e. nothing is deleted). Protein coding sequence can include, for example, luminescent proteins, fluorescent proteins (e.g., fluorescein, fluorescein isothiocyanate, rhodamine, dichlorot[pi]azinylamine fluorescein, green fluorescent protein (GFP), red fluorescent protein (RFP), blue fluorescent dyes excited at wavelengths in the ultraviolet (UV) part of the spectrum (e.g., AMCA (7-amino-4-methylcoumarin-3-acetic acid); Alexa Fluor 350), green fluorescent dyes excited by blue light (e.g., FITC, Cy2, Alexa Fluor 488), red fluorescent dyes excited by green light (e.g., rhodamines, Texas Red, Cy3, Alexa Fluor dyes 546, 564 and 594), or proteins excited with infrared light (e.g., Cy5, dansyl chloride, and phycoerythrin), or enzymatic proteins (e.g., horseradish peroxidase, alkaline phosphatase, beta-galactosidase, glucose-6-phosphatase, and acetylcholinesterase). Other protein coding sequences are contemplated and not limited by the above examples.

In suitable embodiments, the recombinant *Salmonella* strain is a recombinant form of the *enterica* serovar Typhimurium LT2 strain. In the Examples, the inventors utilized the LT2-derived lab strain ASTE13. ASTE13 is similar to DW01, which was sequenced by Song et al. (Nature Communications (2017) 8:14737; see Supplementary Note 1A and Supplementary Table 1 for sequencing data). Suitable LT2 strains are publically available, for example, from the ATCC, for example, ATCC #700720 or ATCC #19585. In a suitable embodiment, the modified strain is derived from ATCC #700720.

Preferably, in some embodiments, the strain can further comprise one or more modifications to reduce the pathogenicity or virulence of the *Salmonella* strain. In some embodiments, the *Salmonella* strain is altered to increase the safety of handling of the strain. For example, in some embodiments one or more pathogen or virulent genes has been knocked out, deleted or silenced. Disclosed herein is a bacterium that has been made deficient in one or more genes associated with virulence in addition to the deletion or reduction of HilE and/or the insertion of a tag in the 3'UTR of hilD. As used herein, "deficient" means that the bacterium does not express a functional form of a protein encoded by the gene.

As such, deficiencies may include deletions, insertion, premature stop codons and the like, but preferably the bacteria disclosed herein have been made deficient in one or more genes associated with virulence via deletion of at least a portion of the gene, and preferably the entirety of the gene.

A "deletion" refers to a change in the amino acid or nucleotide sequence that results in the absence of one or more amino acid residues or nucleotides. A deletion removes at least 1, 2, 3, 4, 5, 10, 20, 50, 100, or 200 amino acids residues or nucleotides. A deletion may include an internal deletion or a terminal deletion (e.g., an N-terminal truncation or a C-terminal truncation of a reference polypeptide or a 5'-terminal or 3'-terminal truncation of a reference polynucleotide).

Suitable methods of reducing the pathogenicity or virulence are known in the art. Suitable pathogenic or virulence genes are known to one skilled in the art and include, but are not limited to, for example, sipD, sipB, sipC, flhDC, pathogenicity islands 1, 4 and 5 (SPI-4, SPI-5), pSLT, pathogenicity island 2 (SPI-2), pathogenicity island 3 (SPI-3), csgD among others, some of which are demonstrated in the examples below. In one example, the strain is ΔsipD. In another example, the strain is ΔSPI-4 or ΔSPI-5. One skilled in the art would be able to knock out or reduce expression of the one or more pathogenicity or virulence genes by methods known in the art.

In some embodiments, the recombinant *Salmonella* strain has at least 2 fold increased secretion titer of a protein of interest by the Type III secretion system as compared to a non-recombinant *Salmonella* strain having a Type III secretion system. In some embodiments, the recombinant *Salmonella* strain has at least 2.5 fold increased secretion titer, alternatively at least 3 fold increased secretion titer, alternatively at least 3.5 fold increase in secretion titer, alternatively at least 4 fold increase in secretion titer of a protein of interest by the Type III secretion system as compared to a non-recombinant *Salmonella* strain having a Type III secretion system.

The present disclosure further provides an in vitro method of making a heterologous protein of interest or a fusion protein comprising the protein of interest using the recombinant bacterial strain, e.g., *Salmonella* strain/cell described herein. The method comprises (a) expressing a heterologous protein of interest or a fusion protein of the protein of interest in the recombinant *Salmonella* strain described herein. The protein of interest is secreted into medium in which the *Salmonella* are suspended. The protein of interest can then be isolated from the medium. In some embodiments, the medium is an optimized medium which increases protein expression from the recombinant *Salmonella*. In some examples, the methods comprise introducing only one vector encoding the protein of interest into the modified bacterial strain to produce a secreted protein which can be isolated from the medium.

Suitably, in one embodiment, no additional exogenous factors (e.g. IPTG) are necessary to induce protein secretion of the protein of interest from the recombinant *Salmonella* cells.

In some embodiments, the heterologous protein of interest is a fusion exogenous protein of interest and a targeting tag. The targeting tag directs the fusion protein to the *Salmonella* Type III secretion system (T3SS). Suitable targeting tags for use in a T3SS system are known in the art, for example, as described in Song et al. 2017, Metcalf et al. 2014 (21, 22), Widmaier et al 2009 (ref 7 in Example 1), incorporated by reference in their entireties. Suitably, in some embodiments, the targeting tag is a suitable heterologous *Salmonella* tag.

One skilled in the art would be able to design a suitable fusion protein of the protein of interest and targeting tag. In one embodiment, the heterologous protein of interest comprises a protein of interest fused to a targeting peptide where the targeting polypeptide is an N-terminal secretion tag under control of a promoter that participates in the activation signal cascade for T3SS. Other promoters may also be used and contemplated in the practice of the present invention, including inducible promoters such as pTet, pLac, etc. In another embodiment, the heterologous protein of interest comprises a cleavable linker between the targeting polypeptide and the protein of interest. The cleavable linker may be a known sequence able to be cleaved by a specific protease or enzyme. Suitable cleavable linkers are known in the art, for example, as described in Chen, Xiaoying et al. "Fusion protein linkers: property, design and functionality" Advanced drug delivery reviews vol. 65, 10 (2012): 1357-69, the contents of which are incorporated by reference in its entirety.

The term "protein of interest" is any protein that is to be produced in in vitro culture that is heterologous to the wild type *Salmonella* and is not naturally secreted by the *Salmonella*. Suitable proteins of interest include, but are not limited to, for example, industrial enzymes, including, but not limited to, for example, cellulases, amylases, and other detergent additives; protein biomaterials, for example, spider silk, silkworm silk, biopolymers, fibroin, elastin-like polypeptides, human elastin, and antimicrobial peptides; therapeutic proteins, including, for example, insulin, drugs, hormones, receptors, growth factors, human extracellular matrix proteins, among others; diagnostic proteins, including, but not limited to, for example, antibodies (e.g. monoclonal antibodies, single chain antibodies, humanized antibodies, etc.), antibody fragments, antigen binding fragments, modified antibodies, tags, among others. Therapeutic proteins are polypeptides which can be administered to a subject to treat a particular disease or disorder. The subject can be a mammal, preferably a primate or human.

The term "recombinant" when used with reference to a cell, nucleic acid, protein, or vector, indicates that the cell, nucleic acid, protein or vector has been artificially modified by adding a heterologous nucleic acid or protein sequence, by altering or deleting part of the native nucleic acid or protein sequence, or that the protein or nucleic acid is derived from a cell so modified. For example, recombinant *Salmonella* cells express genes that are not found within the native *Salmonella* strain (non-recombinant) cell or express native genes that are otherwise abnormally expressed, under expressed or not expressed at all.

The term "isolated" with regard to polypeptide or peptide fragment or polynucleotides as used herein refers to a polypeptide or a peptide fragment or polynucleotide which either has no naturally-occurring counterpart or has been separated or purified from components which naturally accompany it. In some embodiments, the polypeptide or peptide fragment or polynucleotide is considered "isolated" when it is at least 70%, by dry weight, free from the proteins and other naturally-occurring organic molecules with which it is naturally associated.

In some embodiments, the in vitro method of producing a protein of interest comprises introducing a vector encoding the heterologous protein of interest into the recombinant *Salmonella* strain, wherein the heterologous protein of interest is expressed by the recombinant *Salmonella* in culture.

The vector is a recombinant vector (e.g., a recombinant expression vector) comprising the nucleic acid sequence encoding the heterologous protein of interest according to the present invention. The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors" or "recombinant expression vectors."

One type of vector is a "plasmid", which refers to a circular double stranded DNA loop into which additional DNA segments may be ligated, specifically exogenous DNA segments encoding the targeted protein. Another type of vector is a viral vector, wherein additional DNA segments may be ligated into the viral genome. Certain vectors are capable of autonomous replication in a host cell into which they are introduced. Moreover, certain vectors are capable of directing the expression of exogenous genes to which they are operatively linked. In general, vectors of utility in recombinant DNA techniques are often in the form of plasmids.

The vectors are heterogeneous exogenous constructs containing sequences from two or more different sources. Suitable vectors include, but are not limited to, plasmids, expression vectors, among others and includes constructs that are able to express the protein of interest in bacterial cells, preferably *Salmonella* cells.

A vector can preferably transduce, transform or infect a cell, thereby causing the cell to express the nucleic acids and/or proteins encoded by the vector.

The present disclosure also provides a host cell containing a recombinant expression cassette or a recombinant expression vector according to an embodiment of the present disclosure. The host cell is capable of expressing the proteins of the present disclosure. Suitable host cells include, but are not limited to, *Salmonella* cells. In some embodiments, the host cell is used to produce large quantities of the protein.

The vectors disclosed herein may be utilized to transform host cells. Suitable host cells include bacterial.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed below).

Percentage of sequence identity. "Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Protein and nucleic acid sequence identities are evaluated using the Basic Local Alignment Search Tool ("BLAST"), which is well known in the art (Karlin and Altschul, 1990, Proc. Natl. Acad. Sci. USA 87:2267-2268; Altschul et al., 1997, Nucl. Acids Res. 25:3389-3402). The BLAST programs identify homologous sequences by identifying similar segments, which are referred to herein as "high-scoring segment pairs," between a query amino or nucleic acid sequence and a test sequence which is preferably obtained from a protein or nucleic acid sequence database. Preferably, the statistical significance of a high-scoring segment pair is evaluated using the statistical significance formula (Karlin and Altschul, 1990), the disclosure of which is incorporated by reference in its entirety. The BLAST programs can be used with the default parameters or with modified parameters provided by the user. The term "substantial identity" of amino acid sequences for purposes of this invention normally means polypeptide sequence identity of at least 40%. Preferred percent identity of polypeptides can be any integer from 40% to 100%. More preferred embodiments include at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100%.

In some embodiments, the method of making the heterologous protein of interest further comprises isolating the heterologous protein of interest from the medium. The protein of interest can then be isolated from the medium in which the *Salmonella* is cultured. Suitable methods of isolating the protein of interest are also known in the art, for example, size chromatography, affinity chromatography, resin columns, ion exchange, HIC, centrifugation, among others. In some embodiments, the proteins are substantially pure in the medium, and dialysis may be used to exchange the medium for suitable buffer.

After isolation from the medium containing the bacterium from which it was derived, the heterologous protein of interest may be cleaved from the targeting peptide. In one embodiment, the method can comprise contacting the heterologous protein of interest with an enzyme capable of cleaving the protein of interest from the targeting tag. Suitable enzymes, including proteases, are known in the art and are determined by and specific to the cleavable linker sequence selected.

The present disclosure also provides an optimized medium for use in the production of a protein of interest. Specifically, the optimized medium increases the protein secretion titer from *Salmonella* cells, preferably the recombinant *Salmonella* cells described herein. The optimized defined culture medium is able to increase protein secretion for the recombinant bacterial cells. The optimized defined culture medium comprises potassium phosphate and glucose or glycerol, preferably in some examples, glycerol, in an amount effective to increase the ionic content of the media.

The inventors have discovered that if you increasing the ionic content of the media greatly increases the expression and secretion titer from recombinant *Salmonella* cells. Specifically, the inventors found that expression was maximal in the highest concentrations of sodium chloride, MOPS+ NaCl, and potassium phosphate (see para [00135] and FIGS. 7A-7B). The inventors unexpectedly found that there was a synergistic effect in the combination of a carbon source, a buffering agent, and high ionic content which results in an unexpected increase in the secretion titer of the proteins being expressed. The present invention provides in some embodiments a chemically defined medium, wherein the chemically defined medium comprises about 0.4% w/v glycerol or glucose, and about 40 mM or 120 mM potassium phosphate pH 7.4, and about 150 nM to 210 nM NaCl.

Suitably, the optimized defined medium comprises LB broth (about 10 g/L peptone and about 5 g/L yeast extract), with about 80 mM to about 120 mM potassium phosphate, about 0.2% to about 2% w/v glycerol, preferably, in one example, about 0.4% w/v glycerol, and about which in combination increase the ionic content of the media. In one example, the media comprises about 80 mM to 100 mM potassium phosphate. In a suitable example, the potassium phosphate is added from a mixture of 1M $K_2HPO_4$ and 1M $KH_2PO_4$ at a 3:1 ratio, and a pH of about pH 7.2 to pH 7.6, preferably pH of 7.4.

The pH is also important in the optimized media for increasing titer of protein, as demonstrated in the Example below and FIG. 8, carbon sources that acidify the medium (e.g., glucose and glycerol) decrease secretion titer unless they are used in combination with a buffering agent.

In one example, the optimized culture medium able to increase protein secretion comprises LB (about 10 g/L peptone and about 5 g/L yeast extract), about 0.2%-2% w/v glycerol, preferably about 0.4% w/v glycerol, and about 80-120 mM potassium phosphate at a pH of about 7.4, preferably about 90 mM potassium phosphate. In one preferred embodiment, the medium comprises: about 10 g/L peptone, about 5 g/L yeast extract, about 0.4% w/v glycerol, and about 90 mM potassium phosphate pH 7.4. In another example, the optimized culture medium able to increase protein secretion comprises LB (about 10 g/L peptone and about 5 g/L yeast extract), about 0.2%-2% w/v glycerol, preferably about 0.4% w/v glycerol, and about 40-120 mM potassium phosphate, and about 150 nM to about 210 nM NaCl at a pH of about 7.4, preferably about 40 mM potassium phosphate and 150 nM-210 nM NaCl.

In one embodiment, the present disclosure provides an in vitro culture comprising: (a) the recombinant *Salmonella* cell described herein; and (b) defined culture medium for increasing protein secretion as described herein. In one embodiment, the defined culture medium comprises: about 10 g/L peptone, about 5 g/L yeast extract, about 0.2% to about 2% glycerol or glucose (e.g., 0.4% w/v glycerol), and about 80 mM to 100 mM potassium phosphate pH 7.4 (preferably, about 90 mM potassium phosphate).

Methods of isolating the produced protein of interest are known in the art. Suitable methods include, without limitation, size exclusion chromatography, ion exchange chromatography, hydrophobic interaction chromatography, free-flow electrophoresis, affinity chromatography, immunoprecipitation, and high performance liquid chromatography (HPLC). Suitably, the purification strategy may utilize a tag that was engineered into the protein (e.g., a His-tag, a Strep-tag, or an antigen peptide tag), precipitation (e.g., with ammonium sulfate). Tags may also include a TEV cleavage sequence.

Suitably, the isolated protein of interest is substantially pure in the media. By "substantially pure" we mean a preparation in which has a ten fold or greater increase in the purity as compared to traditional (i.e. established) bacterial production methods (for example, either cytosolic or peri-plasmic). Further, the modified strain(s) (e.g., FIG. 5C-5D) significantly increases the starting purity of the product relative to the unoptimized strain.

Kits

In some embodiments, kits for carrying out the methods described herein are provided. The kits provided may contain the necessary components with which to carry out one or more of the above-noted methods. In one embodiment, the present disclosure provides a kit for making a heterolo-gous protein of interest comprising: a recombinant *Salmo-nella* cell of described herein and instructions for culturing and expressing the heterologous protein of interest. The kit may further include the optimized medium described herein. In another embodiment, a kit comprising an in vitro culture system is provided, comprising a recombinant *Salmonella* cell of described herein, a vector capable of being used to express a protein of interest, and optimized medium is provided.

The present recombinant strain, kits and methods provide the benefits of bacterial production (robust, low-cost) com-bined with benefits of eukaryotic protein production (prod-uct purification simplified by recovering product from extra-cellular medium. Further, the optimized growth medium provides a new method of enhancing protein expression via the T3SS. No small molecule addition necessary to induce secretion system or heterologous protein production.

As used herein, "about", "approximately," "substan-tially," and "significantly" will be understood by persons of ordinary skill in the art and will vary to some extent on the context in which they are used. If there are uses of the term which are not clear to persons of ordinary skill in the art given the context in which it is used, "about" and "approxi-mately" will mean plus or minus ≤10% of the particular term and "substantially" and "significantly" will mean plus or minus >10% of the particular term.

Aspects of the disclosure described with respect to the former method can be applicable to the latter method, and vice versa, unless the context clearly dictates otherwise.

The present invention has been described in terms of one or more preferred embodiments, and it should be appreciated that many equivalents, alternatives, variations, and modifi-cations, aside from those expressly stated, are possible and within the scope of the invention.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclu-sive manner, so the referenced elements, components, or steps may be combined with other elements, components, or steps that are not expressly referenced. Embodiments refer-enced as "comprising" certain elements are also contem-plated as "consisting essentially of" and "consisting of" those elements. The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. For example, with regard to sequences "consisting of" refers to the sequence listed in the SEQ ID NO. and does refer to larger sequences that may contain the SEQ ID as a portion thereof.

The invention will be more fully understood upon con-sideration of the following non-limiting examples.

EXAMPLES

Example 1

This Example describes the design and making of a recombinant T3SS expression system for producing exog-enous proteins, methods of producing recombinant proteins and optimized medium for increasing protein secretion titer from the recombinant T3SS system.

Environmental conditions are the key regulators of T3SS expression, and many of the regulators—especially activa-tors—of this process are known [9-14]. Adapting the SPI-1 T3SS for heterologous protein production requires removing or circumventing native regulation that inhibits secretion system activity. T3SS activation is facilitated directly by HilA and its activator, HilD[15-17]. The HilD regulator integrates numerous environmental signals to ensure that the secretion system is activated via HilA only when it senses the appropriate environmental conditions. HilA activation in turn triggers a transcriptional activation cascade that leads to a functional T3SS and secretion. While knowledge of the regulatory network is ever-expanding, it is highly complex and integrated with essential cellular functions, which makes it difficult to engineer directly.

We employed two complementary approaches to address these challenges. First, we increased hilD expression via genomic engineering in the strain to increase SPI-1 activity and thus secretion titer. The function of hilD is controlled from transcription to post-translation, so we could exercise control over its expression at multiple levels. We knocked out HilE (ΔhilE), a negative regulator of HilD, and we attempted to stabilize the hill transcript by adding a 3' transcriptional fusion of a β-barrel fluorescent protein such as GFP or mCherry [18]. Second, we created an optimized growth medium with a combination of glycerol and phos-phate buffer that allows increased cell density while pro-moting secretion via the T3SS. The enhanced strain and optimized growth medium simplify secretion via the engi-neered T3SS and surprisingly provided consistently high secretion titers of the protein.

Results

Methods to Overexpress hilD Confer Increased Secretion

The state-of-the-art method for producing high protein secretion titers using the SPI-1 T3SS is a two-plasmid system: one plasmid carries the heterologous protein product with an N-terminal secretion tag under the control of a promoter that participates in the activation signal cascade for the T3SS, and the second is a synthetically inducible plas-mid for hilA overexpression. Activating the T3SS via plas-mid-based synthetic overexpression of hilA is undesirable for two reasons—first, multiple plasmids increase the com-plexity of the system and require cellular resources for maintenance, and second, an expensive small molecule, IPTG, must be added to the culture to induce hilA overex-pression. Thus, we sought to engineer the genome to elimi-nate this plasmid from the system. We focused on engineer-ing expression of hilD, as more points of control are known for hilD than hilA. First we targeted HilE, which is known to reduce hilA activation by binding to HilD. Previous studies showed that ΔhilE strains confer increased hilA activity [14,19]. HilD activity and therefore hilA activation is also controlled by hilD mRNA stability via its 3' UTR [18]. Previous studies demonstrated that eliminating a portion of the hilI 3' UTR increased transcript stability and secretion system activation. We found, however, that inserting a β-barrel fluorescent protein such as GFP or mCherry at the start of the hilI 3'UTR (i.e., immediately after the coding sequence of hilD) and leaving the 3' UTR otherwise intact significantly increased secretion titer (FIG. 1A). Secretion titer increased 2.4-fold in the hilD::GFP strain and 3-fold in the ΔhilE and hilD::mCherry strains compared to the wild type strain without hilA overexpression. The combination of hilE and hilD::GFP provided a 3-fold increase, while the hilI and hilD::mCherry strain yielded the highest secretion titer, a 3.2-fold increase. Flow cytometry performed at the endpoint of the experiment showed that adding the hilE knockout to the hilD::GFP or hilD::mCherry strains increased hilD expression (FIG. 1B). The enhanced strains produced secretion titers at 80-90% of the state-of-the-art system with only the plasmid carrying the heterologous protein product. No inducer is necessary for protein secretion.

Medium Optimization

Energy-Rich Carbon Sources Decrease Secretion Titer

Added carbon sources and buffering agents are necessary for industrial-scale growth of microorganisms as they allow increased cell density and longer growth times, which generally increase protein product titer. The growth medium used for the state-of-the-art system is LB-Lennox (LB-L), which consists of an LB base (see Methods) with 5 g/L NaCl. Energy-rich carbon sources such as glucose and glycerol strongly decreased secretion titer in LB-L without added buffers, however (FIG. 2A). Only the energy-poor carbon source succinate had a minimal effect on secretion titer. Energy-rich carbon sources repress SPI-1 activity via two known mechanisms: catabolite repression and acidification of the medium [9,11].

High-Phosphate Media Enhances Secretion with Energy-Rich Carbon Sources

Acidification of the medium can be alleviated by adding a buffering agent. In the search for a buffering agent, we discovered that adding 90 mM potassium phosphate at pH 7.4 had a specific beneficial effect in the presence of energy-rich carbon sources (FIG. 2B). We reasoned that this could be a result of buffering or an increase in ionic strength or osmolarity, as we previously showed that increasing the sodium chloride concentration in the growth medium to 17 g/L had a positive effect on secretion titer [8]. We compared phosphate-buffered LB to LB with 17 g/L NaCl and LB with 90 mM MOPS and 10 g/L NaCl in glucose, glycerol and succinate. We measured the conductivity of the media without added carbon sources as a proxy for ionic strength or osmolarity because the LB base remained the same in all conditions tested. Glucose and glycerol increase osmolarity but not conductivity, while succinate increases both osmolarity and conductivity. Though the conductivity of both NaCl-containing media was higher than that of phosphate-buffered LB, neither alternative could match the secretion titers observed in phosphate-buffered LB with glucose or glycerol. Furthermore, phosphate buffer not only rescued the decrease in secretion observed in the presence of rich carbon sources, it produced an additional increase in bulk secretion titer specifically in combination with glycerol.

Figures 3A, 3B:
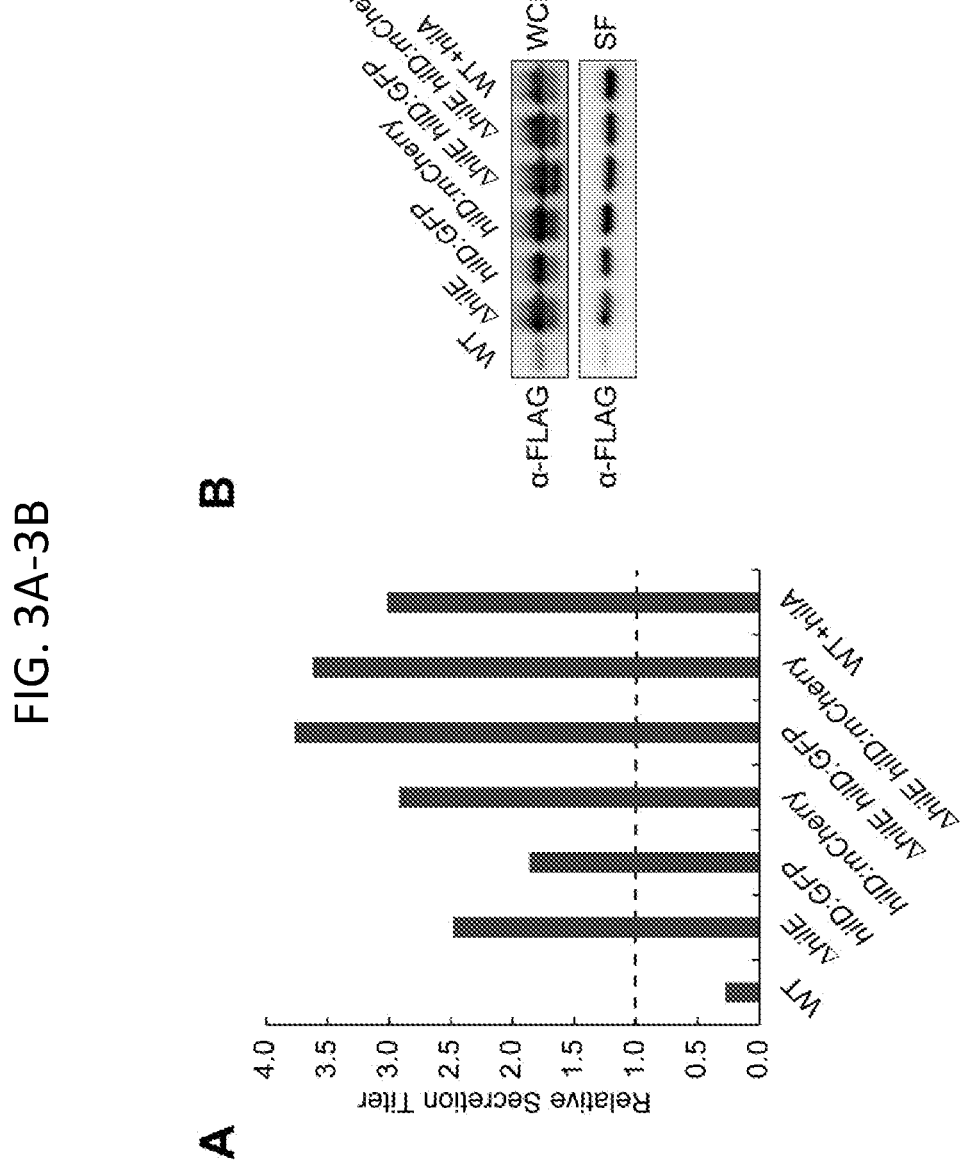
FIG. 3A-3B. Secretion using the enhanced strains in an optimized medium. (A) Secretion titer of SptP-DH-2× FLAG-6×His from the genomically modified strains was normalized to ASTE13 WT in LB-L with hilA overexpression by performing densitometry on western blots. "WT" denotes a genetically wild type strain without the hilA overexpression plasmid. (B) Western blots used for densitometry (SF) and that depict total protein expression (WCL). "SF" is secreted fraction and "WCL" is whole culture lysate.
Figure 3C:
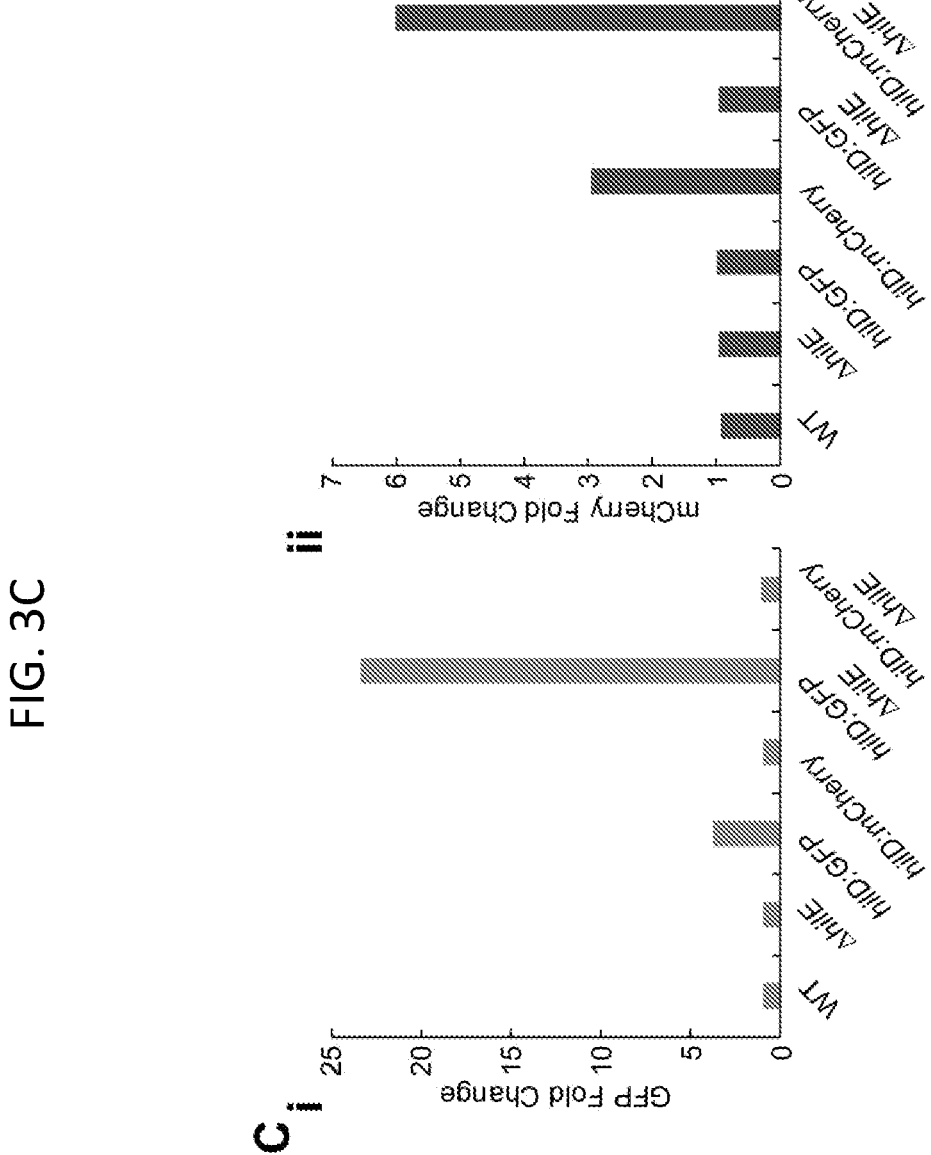
FIG. 3C. Fold change of fluorescence geometric mean for GFP and mCherry according to flow cytometry showing synergy. Results represent a single biological replicate.

Combining Media and Strain Improvements Leads to Synergistic Effects on Secretion Secretion Titer is Maximized by Overexpressing hilD in High-Phosphate Media While the enhanced strains, HASTE15g and HASTE15c, and the optimized medium, LB with 0.4% w/v glycerol and 90 mM potassium phosphate pH 7.4, separately increase the utility of the T3SS for protein production, they have a more than additive effect when combined (FIG. 3). An approximately fourfold increase in secretion titer is observed with the enhanced strain in the optimized medium compared to a threefold increase in the optimized medium observed with the state-of-the-art two-plasmid system.

Methods

Strains and Growth Conditions

The *Salmonella enterica* serovar Typhimurium LT2 strains and isogenic mutant strains used in this work are listed in Table 1. DW01 is found in Song et al. "Control of type III protein secretion using a minimal genetic system." Nature Communications. 2017; 8:14737, the content of which is incorporated by reference in its entirety. The DW01 lab strain was sequenced can be found Supplementary Note 1A and Supplementary Table 1 of Song et al., incorporated by reference in its entirety herein.

Secretion experiments were started by growing a single colony from a fresh streak of a frozen glycerol stock in the lysogeny broth Lennox formulation (10 g/L peptone, 5 g/L yeast extract, 5 g/L NaCl) with appropriate antibiotics (34 μg/mL chloramphenicol for secretion plasmid, 50 μg/mL kanamycin for hilA overexpression plasmid) for 12-16 hours overnight in an orbital shaker at 37° C. and 225 rpm. Overnight cultures were diluted 1:100 into the appropriate medium and supplemented as necessary with 100 μg/mL isopropyl β-D-1-thiogalactopyranoside (IPTG) and antibiotics. All culturing steps were performed in 24-well deepwell blocks (Axygen). Secretion was performed for 8 hours at 37° C. and 225 rpm in an orbital shaker. Whole culture lysate samples for SDS-PAGE were prepared by adding 10 μL of cell suspension to 50 μL of 4× Laemmli buffer at the end of secretion. The secretion fraction was harvested by centrifuging cultures at 4000×g for 10 minutes. SDS-PAGE samples for the secretion fraction were prepared by adding 10 μL of supernatant to 30 μL of $H_2O$ and 16 μL of 4× Laemmli buffer. All SDS-PAGE samples were boiled at 95° C. for 5 minutes immediately after preparation.

TABLE 1

Strains and plasmids used in this study.

| Strain Name | Comment | Reference |
|---|---|---|
| ASTE13 | LT2-derived lab strain similar to DW01 | This study; DW01 [21] |
| ASTE13 hilE | hilE knockout | This study |
| ASTE13 hilD::GFPmut2 | GFPmut2 inserted immediately downstream of hilD coding sequence | This study |
| ASTE 13 hilD::mCherry | mCherry inserted immediately downstream of hilD coding sequence | This study |
| HASTE15g | hilE knockout; GFPmut2 inserted immediately downstream of hilD coding sequence | This study |

TABLE 1-continued

| Strains and plasmids used in this study. | | |
|---|---|---|
| HASTE15c | hilE knockout; mCherry inserted immediately downstream of hilD coding sequence | This study |

| Plasmid Name | ORFs | under inducible control | ORI | ab$^R$ | Reference |
|---|---|---|---|---|---|
| P$_{sic}$ DH | sicP | sptP-DH-2xFLAG-6xHis | colE1 | cam | [22] |
| P$_{sic}$ Bla | sicP | sptP-bla-2xFLAG-6xHis | colE1 | cam | [22] |
| P$_{lacUV5}$ hilAhilA | | | p15a | kan | [22] |

Medium Formulations

"LB" refers to a base medium formulation of 10 g/L peptone and 5 g/L yeast extract, and "TB" is the standard Terrific Broth formulation: 12 g/L peptone, 24 g/L yeast extract, 9.4 g/L K2HPO4, and 2.2 g/L KH2PO4. LB-L is 10 g/L peptone, 5 g/L yeast extract, and 5 g/L NaCl. Carbon sources were prepared as 20% solutions, sterile filtered, and diluted to 0.4% at the time of subculture. Unless otherwise specified, phosphate buffers were created by diluting 1M $K_2HPO_4$ and 1M $KH_2PO_4$ to the appropriate concentration in a 3:1 ratio to produce a solution with pH 7.4. MOPS buffer was a 1M solution pH adjusted to 7.4 with NaOH. Different medium formulations were prepared by adding the appropriate amounts of sterile 1M buffers, 5M sodium chloride (NaCl), and 20% carbon source solutions to an autoclaved LB base medium. Sterile ultrafiltered water was added if necessary to ensure each sample had an equal volume of added solutions. Peptone, tryptone and yeast extract were sourced from BD Bacto.

DNA Manipulations

Plasmids used in this work are listed in Table 1. Genomic modifications were created using recombineering as described by Court and colleagues [20]. Primers used for recombineering and the sequenced genetic changes are listed in Table 2.

TABLE 2

| Primers used for recombineering. | |
|---|---|
| Sequence | Used to Construct This Strain |
| AACTACGCCATCGACATTCATAAAAATGGCGAACC ATTAAATTAAAGAGGAGAAAGGTCATGAG (SEQ ID NO: 1) | ASTE13 hilD::GFPmut2 |
| TTAATAAAAATCTTTACTTAAGTGACAGATACAAA AAATGTTATTTGTATAGTTCATCCATGCCATG (SEQ ID NO: 2) | ASTE13 hilD::GFPmut2 |
| AACTACGCCATCGACATTCATAAAAATGGCGAACC ATTAAATTAAAGAGGAGAAAGGTCATGGTTTCCAAGGGCG (SEQ ID NO: 3) | ASTE13 hilD::mCherry |
| TTAATAAAAATCTTTACTTAAGTGACAGATACAAA AAATGTTATTTGTACAGCTCATCCATGC (SEQ ID NO: 4) | ASTE13 hilD::mCherry |
| AACTACGCCATCGACATTCATAAAAATGGCGAACC (SEQ ID NO: 5) | ASTE13 hilD::GFPmut2, |
| ATTAATGTGACGGAAGATCACTTCG (SEQ ID NO: 6) | ASTE13 hilD::mCherry |
| ATAAAAATCTTTACTTAAGTGACAGATACAAAAAA (SEQ ID NO: 7) | ASTE13 hilD::GFPmut2, |
| TGATCAAAGGGAAAACTGTCCATAT (SEQ ID NO: 8) | ASTE13 hilD::mCherry |
| ACGAAATGGCTGGAAAATGGAACGTTCTTTCATTG TTGGCTGTGACGGAAGATCACTTCG (SEQ ID NO: 9) | ASTE13 hilE |
| GTCCTCATCGCCACAGCGCCTGTCGGTGAAGAGGC CGCCATCAAAGGGAAAACTGTCCAT (SEQ ID NO: 10) | ASTE13 hilE |
| ATGGCTGGAAAATGGAACGTTCTTTCATTGTTGGC GGCGGCCTCTTCACCGACAGGCGCTGTGGCGATGA (SEQ ID NO: 11) | ASTE13 hilE |

Protein Separation and Western Blotting

Samples were separated by SDS-PAGE and transferred to a polyvinylidene fluoride membrane (PVDF, Millipore) for western blotting using the Bio-Rad Transblot SD unit or the Bio-Rad Criterion blotter. Membranes were probed with mouse anti-FLAG per manufacturer's instructions (Sigma Aldrich). To facilitate chemiluminescent detection, a secondary labeling step was performed with goat anti-mouse IgG (H+L) HRP conjugate according to manufacturer's instructions (Thermo Fisher). Bands were detected with the SuperSignal West Pico substrate (Thermo Fisher) and a ChemiDoc XRS+imaging system (Bio-Rad).

Protein Quantification

All relative protein quantities were calculated by performing densitometry using Image Lab software (Bio-Rad) and normalizing as specified.

Flow Cytometry

Strains were grown and induced as specified in "Strains and Growth Conditions". Samples were prepared by diluting cultures to an optical density at 600 nm of 0.005 to 0.05 in sterile PBS in round-bottom 96-well plates (Greiner Bio-One #650101). Plates were sealed and stored at 4° C. for analysis. For each sample, an Attune NXT flow cytometer (Life Technologies) was used to collect 10,000 events within a gated population determined to be cells. Data was analyzed using FlowJo 10.5.3 (TreeStar, Inc.).

REFERENCES

1. Rosano G L, Ceccarelli E A. Recombinant protein expression in *Escherichia coli*: advances and challenges. Front Microbiol. 2014; 5:172.
2. Reed B, Chen R. Biotechnological applications of bacterial protein secretion: from therapeutics to biofuel production. Research in Microbiology. 2013; 164:675-82.
3. Clark E D B. Protein refolding for industrial processes. Current Opinion in Biotechnology. 2001; 12:202-7.
4. Azam A, Li C, Metcalf K J, Tullman-Ercek D. Type III secretion as a generalizable strategy for the production of full-length biopolymer-forming proteins. Biotechnol Bioeng. 2015; n/a-n/a.
5. Deng W, Marshall N C, Rowland J L, McCoy J M, Worrall L J, Santos A S, et al. Assembly, structure, function and regulation of type III secretion systems. Nature Reviews Microbiology. 2017; 15:323-37.
6. Galán J E, Lara-Tejero M, Marlovits T C, Wagner S. Bacterial Type III Secretion Systems: Specialized Nanomachines for Protein Delivery into Target Cells. Annual Review of Microbiology. 2014; 68:415-38.
7. Widmaier D M, Tullman-Ercek D, Mirsky E A, Hill R, Govindarajan S, Minshull J, et al. Engineering the *Salmonella* type III secretion system to export spider silk monomers. Mol Syst Biol. 2009; 5:309.
8. Metcalf K J, Bevington J L, Rosales S L, Burdette L A, Valdivia E, Tullman-Ercek D. Proteins adopt functionally active conformations after type III secretion. Microbial Cell Factories. 2016; 15:213.
9. Golubeva Y A, Sadik A Y, Ellermeier J R, Slauch J M. Integrating Global Regulatory Input Into the *Salmonella* Pathogenicity Island 1 Type III Secretion System. Genetics. 2012; 190:79-90.
10. Teplitski M, Goodier R I, Ahmer B M M. Catabolite repression of the SirA regulatory cascade in *Salmonella enterica*. International Journal of Medical Microbiology. 2006; 296:449-66.
11. Ellermeier J R, Slauch J M. Adaptation to the host environment: regulation of the SPI1 type III secretion system in *Salmonella enterica* serovar Typhimurium. Current Opinion in Microbiology. 2007; 10:24-9.
12. Mizusaki H, Takaya A, Yamamoto T, Aizawa S-I. Signal Pathway in Salt-Activated Expression of the *Salmonella* Pathogenicity Island 1 Type III Secretion System in *Salmonella enterica* Serovar Typhimurium. J Bacteriol. 2008; 190:4624-31.
13. Erhardt M, Dersch P. Regulatory principles governing *Salmonella* and *Yersinia* virulence. *Salmonella*. 2015; 949.
14. Baxter M A, Jones B D. Two-Component Regulators Control hilA Expression by Controlling fimZ and hilE Expression within *Salmonella enterica* Serovar Typhimurium. Infect Immun. 2015; 83:978-85.
15. Petrone B L, Stringer A M, Wade J T. Identification of HilD-Regulated Genes in *Salmonella enterica* Serovar Typhimurium. J Bacteriol. 2014; 196:1094-101.
16. Sturm A, Heinemann M, Arnoldini M, Benecke A, Ackermann M, Benz M, et al. The Cost of Virulence: Retarded Growth of *Salmonella* Typhimurium Cells Expressing Type III Secretion System 1. PLoS Pathog. 2011; 7:e1002143.
17. Ellermeier C D, Ellermeier J R, Slauch J M. HilD, HilC and RtsA constitute a feed forward loop that controls expression of the SPI1 type three secretion system regulator hilA in *Salmonella enterica* serovar Typhimurium. Molecular Microbiology. 2005; 57:691-705.
18. López-Garrido J, Puerta-Fernández E, Casadesús J. A eukaryotic-like 3' untranslated region in *Salmonella enterica* hilD mRNA. Nucleic Acids Res. 2014; 42:5894-906.
19. Baxter M A, Fahlen T F, Wilson R L, Jones B D. HilE Interacts with HilD and Negatively Regulates hilA Transcription and Expression of the *Salmonella enterica* Serovar Typhimurium Invasive Phenotype. Infect Immun. 2003; 71:1295-305.
20. Thomason L C, Sawitzke J A, Li X, Costantino N, Court D L. Recombineering: Genetic Engineering in Bacteria Using Homologous Recombination. Current Protocols in Molecular Biology. 2014; 106:1.16.1-1.16.39.
21. Song M, Sukovich D J, Ciccarelli L, Mayr J, Fernandez-Rodriguez J, Mirsky E A, et al. Control of type III protein secretion using a minimal genetic system. Nature Communications. 2017; 8:14737.
22. Metcalf K J, Finnerty C, Azam A, Valdivia E, Tullman-Ercek D. Using Transcriptional Control To Increase Titers of Secreted Heterologous Proteins by the Type III Secretion System. Appl Environ Microbiol. 2014; 80:5927-34.

Example 2

This Example describes additional modifications that may be made to the recombinant strains (HASTE15g and HASTE15c). Here, the inventors determined that individual gene knockouts of several pathogenic operons and native SPI-1 substrates had minimal effects on protein expression and secretion titer.

This Example also describes the effect of several non-essential gene knockouts on heterologous protein expression and secretion and identify genomic modifications that mimic the effects of synthetic hilA overexpression. Individual gene knockouts of several pathogenic operons and native SPI-1 substrates had minimal effects on protein expression and secretion titer. The SPI-1 regulator HilD acts upstream of hilA, so we hypothesized that genomic modifications that increased HilD expression would have the same effect as synthetic hilA overexpression. Indeed, deleting the HilD repressor HilE and inserting genes between the hilD coding sequence and its 3' UTR achieved similar levels of heterologous protein expression and secretion as synthetic hilA overexpression. In combination with the LB-(KH$_2$PO$_4$/K$_2$HPO$_4$) medium with glycerol, the engineered strain produced higher secretion titers than those achieved with synthetic hilA overexpression.

Results

SPI-1 Effector Knockouts do not Alter Secretion Titer

Figures 4A, 4B:
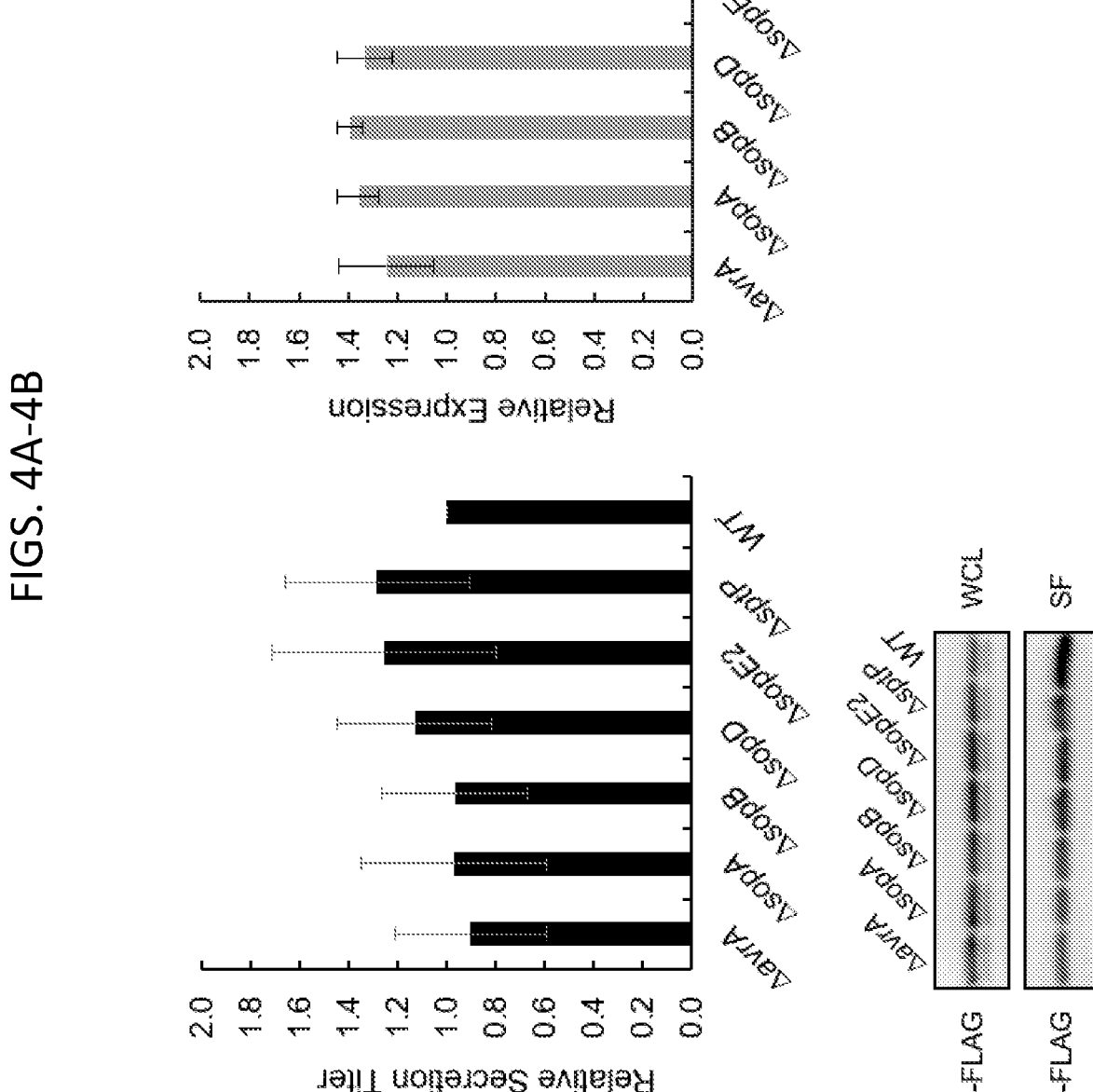
FIGS. 4A-4B. Relative expression and secretion titer for individual SPI-1 effector knockouts. (A) Relative bulk secretion titer (left) and expression (right) of SptP-DH-2× FLAG-6×His in ASTE13 WT and SPI-1 effector knockouts in LB-L with hilA overexpression. Expression and secretion titer were measured via semi-quantitative western blotting and normalized to ASTE13 WT. Error bars represent standard error. (B) Western blots are representative of three biological replicates.

Deleting native substrates of the SPI-1 T3SS (effectors) achieves two goals simultaneously: first, they are incapable of executing their pathogenic function, and second, their absence increases the purity of the secreted protein. Though no literature evidence suggested that knocking out non-structural native SPI-1 T3SS substrates would change secretion behavior, it was important to evaluate the effect of each knockout individually. Fortunately, of the seven effector knockouts tested, none had a significant impact on secretion titer of SptP-DH-2×FLAG-6×His (FIGS. 4A-4B). All of the knockouts increased relative expression by a small margin.

A T3SS Tip Complex Knockout Increases Secretion Titer Twofold

Figures 5A, 5B:
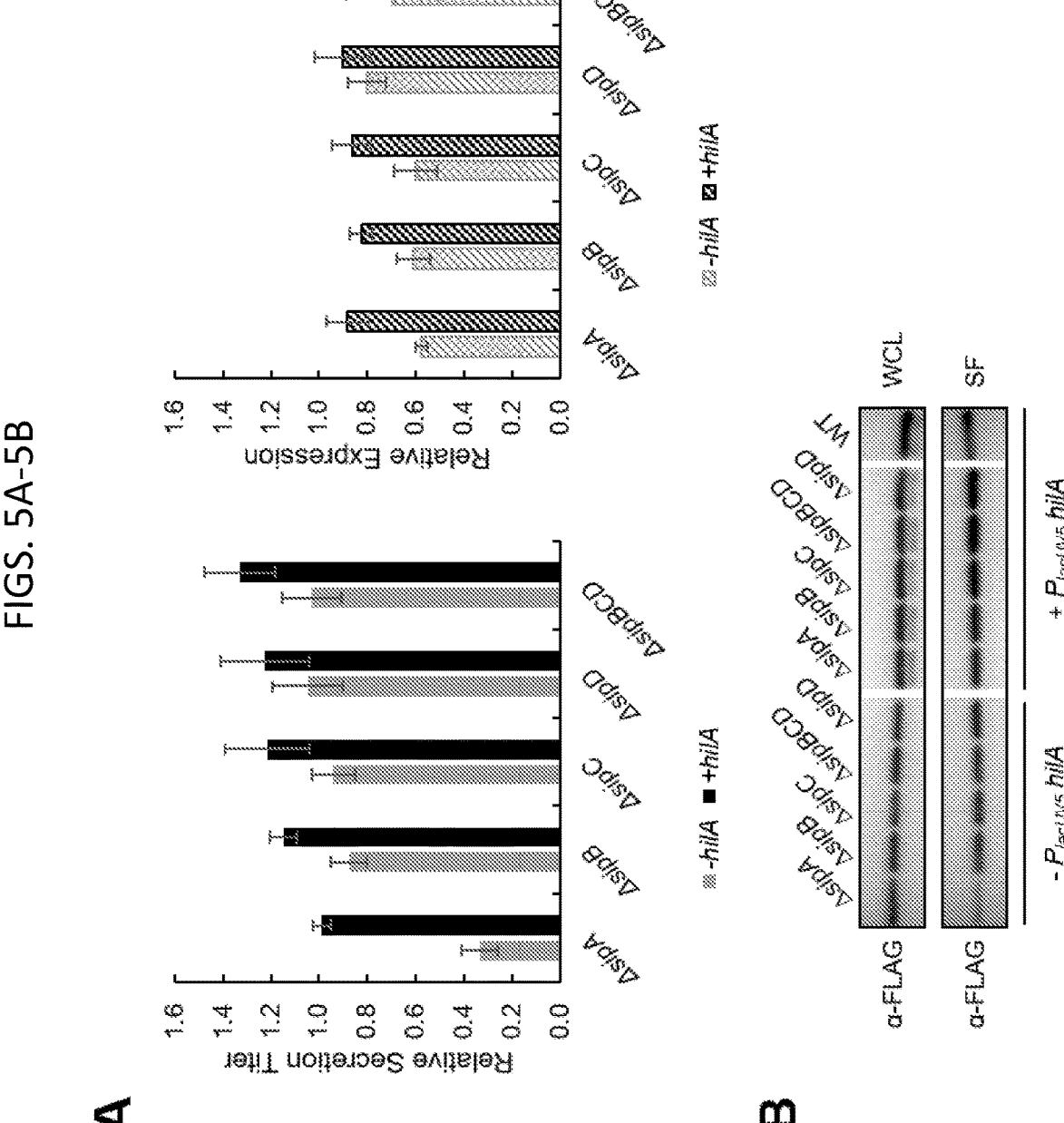
FIGS. 5A-5B. Relative expression and secretion titer for sip knockouts. (A) Relative bulk secretion titer (left) and expression (right) of SptP-DH-GFP11-2×FLAG-6×His in ASTE13 WT and the listed sip knockouts in LB-L with hilA overexpression. Expression and secretion titer were measured via semi-quantitative western blotting and normalized to ASTE13 WT. Error bars represent standard error. (B) Western blots are representative of three biological replicates.

In previous work we showed that ΔsipD strains increase heterologous secretion titer via the SPI-1 T3SS [52], but the impact of deleting the remaining tip complex members SipB and SipC and the secreted effector SipA was unknown. In combination with hilA overexpression, the individual knockout strains ΔsipB, ΔsipC, and ΔsipD had the same effect of increased secretion titer, but they were not additive (FIGS. 5A-5B). We were surprised to observe that the individual and combined knockouts of SipB, SipC, and SipD produced similar heterologous protein expression and secretion titer in strains with and without the hilA overexpression vector.

A Double Knockout Increases the Purity of the Secreted Product

Figures 5C, 5D:
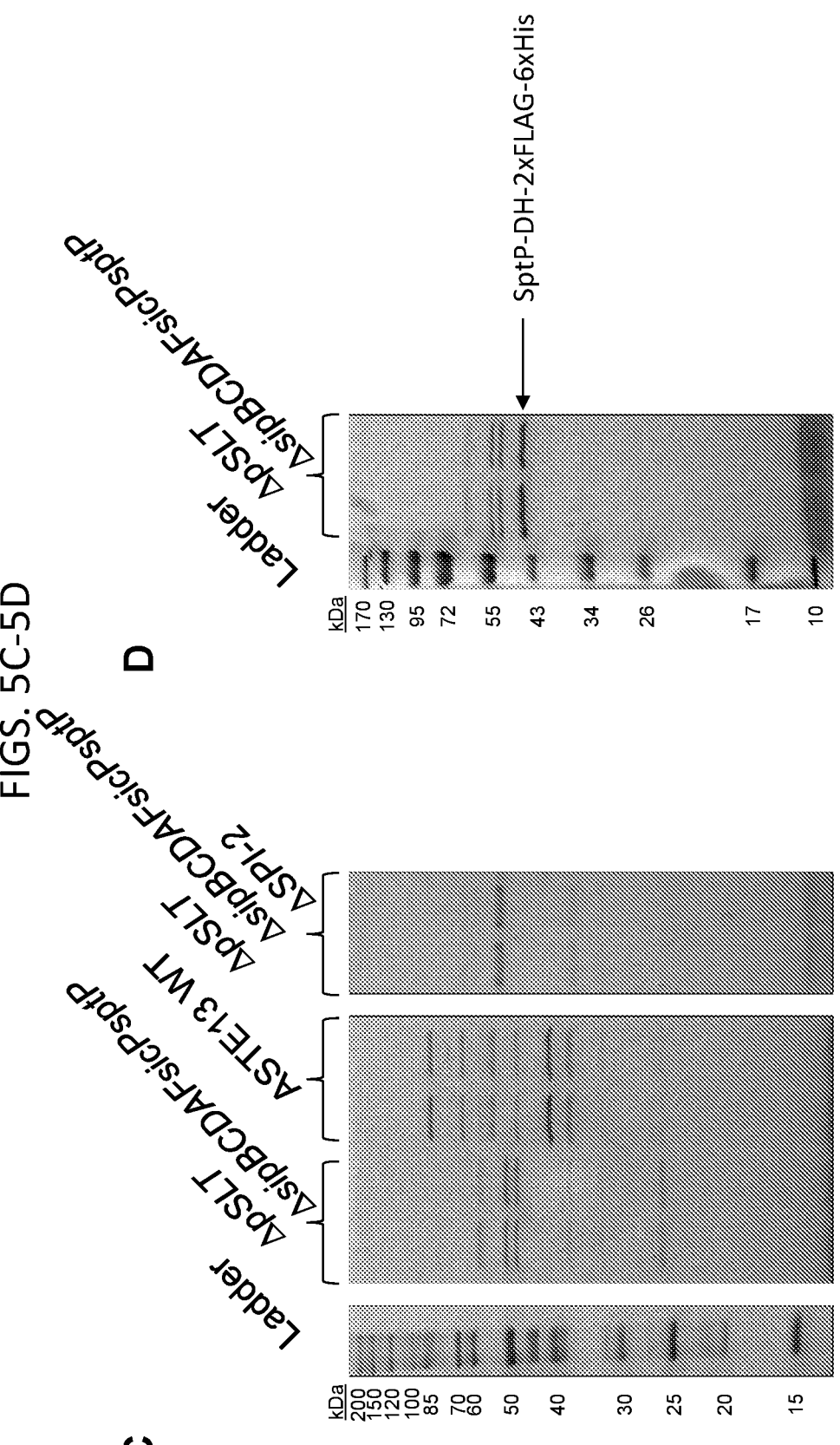
FIGS. 5C-5D. Coomassie-stained secretion fraction for ΔsipBCDAFsicPsptP and a ΔsipBCDAFsicPsptP ΔSPI-2 double knockout. (A) Secreted fractions compared to ASTE13 WT with no heterologous secreted protein. All strains were induced to overexpress hilA. (B) ASTE13 ΔsipBCDAFsicPsptP with hilA overexpression and PsicA sptP-DH-2×FLAG-6×His.

Building on the tip complex and individual SPI-1 T3SS substrate knockouts, we deleted the entire sic operon to create ASTE13 sipBCDAFsicPsptP. To that strain, we added a SPI-2 knockout, which encodes a second T3SS. The sipBCDAFsicPsptP knockout significantly improves the purity of the secreted fraction relative to the unmodified ASTE13 WT strain. The purity of the secreted fraction is further increased by adding the SPI-2 knockout (FIG. 5C-D). The sipBCDAFsicPsptP strain is functional for secretion, and the strength of the band on a Coomassie-stained gel suggests that the sipBCDAFsicPsptP knockout confers a similar increase in secretion as the sipBCD knockout (FIG. 5C-5D).

Non-Essential Pathogenic Gene Knockouts do not Alter Secretion Titer

Figures 6A, 6B:
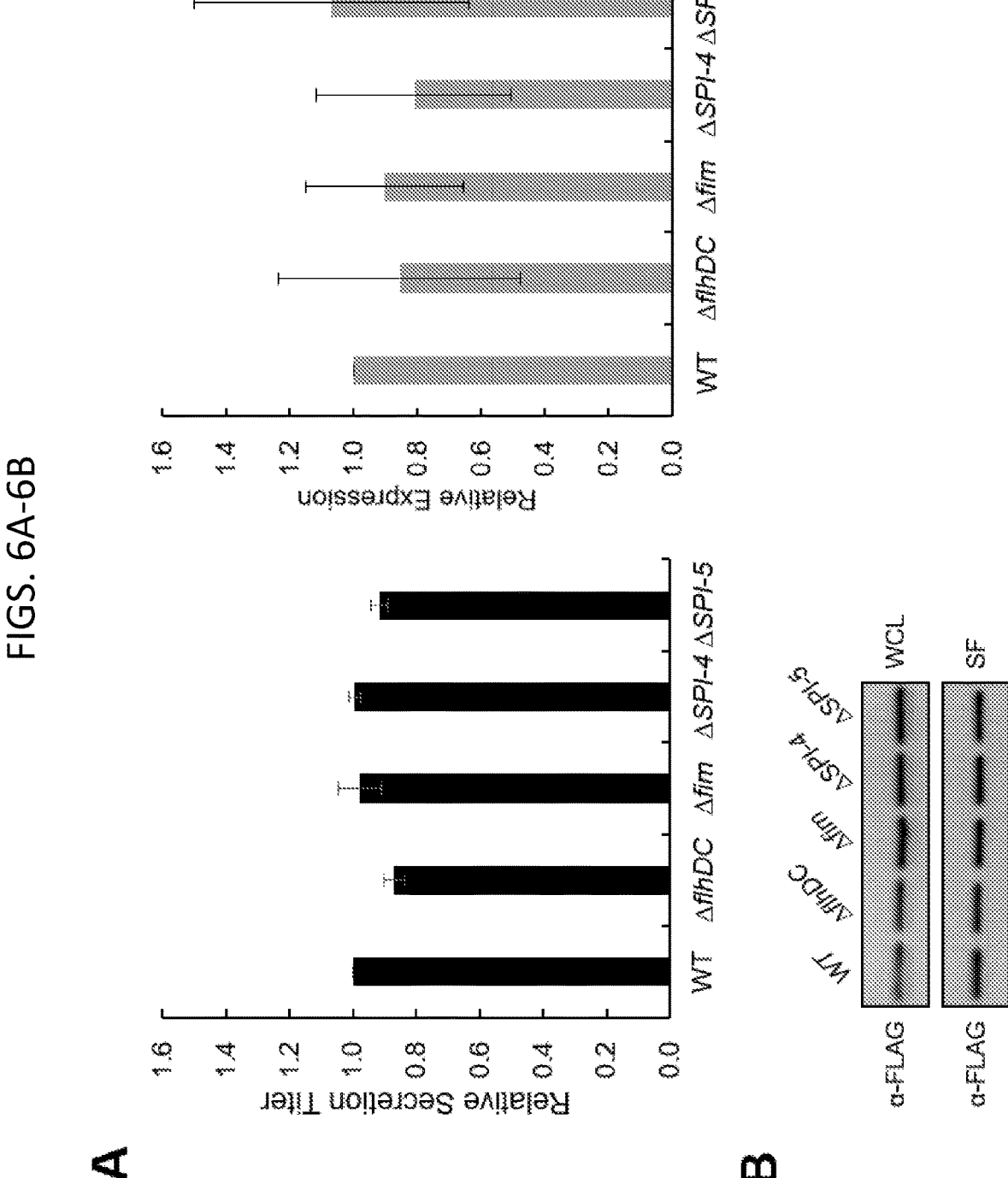
FIGS. 6A-6B. Relative expression and secretion titer for non-essential pathogenic gene knockouts. (A) Relative bulk secretion titer (left) and expression (right) of SptP-DH-2× FLAG-6×His in ASTE13 WT and the specified gene knockouts in TB with hilA overexpression. Expression and secretion titer were measured via semi-quantitative western blotting and normalized to ASTE13 WT. Error bars represent one standard deviation. (B) Western blots are representative of three biological replicates.

The genome of *Salmonella enterica* Typhimurium contains many operons that facilitate its pathogenic program, and these genes should be removed to create a non-pathogenic organism and improve heterologous protein production by freeing cellular resources. As with the native substrates of the SPI-1 T3SS, it was important to evaluate the effects of removing those operons individually. Fortunately, the impact of knocking out the flagellar master regulators FlhDC, the type I fimbriae-producing fim operon, and *Salmonella* pathogenicity islands 4 and 5 (SPI-4 and SPI-5) was minimal (FIGS. 6A-6B). No significant differences in expression were observed among the knockout strains. The ΔflhDC and ΔSPI-5 strains showed a 10-20% decrease in secretion titer, but that will likely be negligible in combination with other strain and process improvements.

Methods

Strains and Growth Conditions

Strains and plasmids used in this work are listed in Table 3 and Table 4. Secretion experiments were started by growing a single colony from a fresh streak of a frozen glycerol stock in the lysogeny broth Lennox formulation (10 g/L tryptone, 5 g/L yeast extract, 5 g/L NaCl) with appropriate antibiotics (34 μg/mL chloramphenicol for the plasmid expressing the secreted protein, 50 μg/mL kanamycin for the P$_{lacUV5}$ hilA overexpression vector) for 12-16 hours overnight in an orbital shaker at 37° C. and 225 rpm. Overnight cultures were diluted 1:100 into the appropriate medium supplemented with appropriate antibiotics and 100 μg/mL isopropyl β-D-1-thiogalactopyranoside (IPTG) if the strain carried P$_{lacUV5}$ hilA. All culturing steps were performed in 24-well deepwell plates (Axygen). Secretion was performed for 8 hours at 37° C. and 225 rpm in an orbital shaker. Whole culture lysate samples for SDS-PAGE were prepared by adding cell suspension to Laemmli buffer in a 1:2 ratio at the end of secretion. The secretion fraction was harvested by centrifuging cultures at 4000×g for 10 minutes. SDS-PAGE samples for the secretion fraction were prepared by adding supernatant to Laemmli buffer in a 3:1 ratio. All SDS-PAGE samples were boiled at 95° C. for 5 minutes immediately after preparation.

TABLE 3

| Strains used in Example 2 | | |
| --- | --- | --- |
| Strain Name | Comment | Reference |
| ASTE13 | LT2-derived lab strain similar to DW01 | This study; DW01 [21] |
| ASTE13 hilE | hilE knockout | This study |
| ASTE13 hilD::GFPmut2 | GFPmut2 inserted immediately downstream of hilD coding sequence | This study |
| ASTE 13 hilD::mCherry | mCherry inserted immediately downstream of hilD coding sequence | This study |
| HASTE15g | hilE knockout; GFPmut2 inserted immediately downstream of hilD coding sequence | This study |
| HASTE15c | hilE knockout; mCherry inserted immediately downstream of hilD coding sequence | This study |
| ASTE13 avrA | avrA knockout | This study |
| ASTE13 sopA | sopA knockout | This study |
| ASTE13 sopB | sopB knockout | This study |
| ASTE13 sopD | sopD knockout | This study |
| ASTE13 sopE2 | sopE2 knockout | This study |

TABLE 3-continued

| Strains used in Example 2 | | |
|---|---|---|
| Strain Name | Comment | Reference |
| ASTE13 sptP | sptP knockout | This study |
| ASTE13 sipA | sipA knockout | This study |
| ASTE13 sipB | sipB knockout | This study |
| ASTE13 sipC | sipC knockout | This study |
| ASTE13 sipD | sipD knockout | This study |
| ASTE13 sipBCD | sipBCD knockout | This study |
| ASTE13 fim | fim knockout | This study |
| ASTE13 flhDC | flhDC knockout | This study |
| ASTE13 SPI-4 | SPI-4 knockout | This study |
| ASTE13 SPI-5 | SPI-5 knockout | This study |
| ASTE13 pSLT sipBCDAFsicPsptP | pSLT sipBCDAFsicPsptP knockout | This study |
| ASTE13 pSLT sipBCDAFsicPsptP SPI-2 | pSLT sipBCDAFsicPsptP SPI-2 knockout | This study |

TABLE 4

| Plasmids used in Example 2 | | | | |
|---|---|---|---|---|
| Plasmid Name | ORFs under inducible control | ORI | ab$^R$ | Reference |
| P$_{sic}$ DH | sicP    sptP-DH-2xFLAG-6xHis | colE1 | cam | [22] |
| P$_{sic}$ Bla | sicP    sptP-bla-2xFLAG-6xHis | colE1 | cam | [22] |
| P$_{lacUV5}$ hilA | hilA | p15a | kan | [22] |

Recombineering

Recombineering was performed in *S. enterica* Typhimurium ASTE13 as described by Thomason et al. [152]. Briefly, a cat-sacB cassette conferring chloramphenicol resistance and sucrose sensitivity was amplified using primers with 40 bp of homology 5' and 3' to the locus of interest. Genes for GFPmut2 and mCherry were amplified using primers containing the same 40 bp of homology 5' and 3' to the locus of interest as used for the cat-sacB cassette. PCR was performed with Phusion DNA polymerase and the primers listed in Table 5. *S. enterica* Typhimurium ASTE13 was first transformed with pSIM6. A first round of recombineering was performed to insert the cat-sacB cassette at the locus of interest, and a second round of recombineering replaced the cat-sacB cassette with GFPmut2 or mCherry for transcriptional fusions or a 60 bp oligo containing the first and last 30 bp of hilE for the hilE gene knockout. The genomic modifications were confirmed by Sanger sequencing (Quintara), and the strains were cured of pSIM6.

TABLE 5

| Primers used in Example 2 | |
|---|---|
| Sequence | Used to Construct This Strain |
| AACTACGCCATCGACATTCATAAAAATGGCGAACC ATTAAATTAAAGAGGAGAAAGGTCATGAG (SEQ ID NO: 1) | ASTE13 hilD::GFPmut2 |
| TTAATAAAAATCTTTACTTAAGTGACAGATACAAA AAATGTTATTTGTATAGTTCATCCATGCCATG (SEQ ID NO: 2) | ASTE13 hilD::GFPmut2 |
| AACTACGCCATCGACATTCATAAAAATGGCGAACC ATTAAATTAAAGAGGAGAAAGGTCATGGTTTCCAA GGGCG (SEQ ID NO: 3) | ASTE13 hilD::mCherry |
| TTAATAAAAATCTTTACTTAAGTGACAGATACAAA AAATGTTATTTGTACAGCTCATCCATGC (SEQ ID NO: 4) | ASTE13 hilD::mCherry |
| AACTACGCCATCGACATTCATAAAAATGGCGAACC ATTAATGTGACGGAAGATCACTTCG (SEQ ID NO: 12) | ASTE13 hilD::GFPmut2, ASTE13 hilD::mCherry |
| ATAAAAATCTTTACTTAAGTGACAGATACAAAAAA TGATCAAAGGGAAAACTGTCCATAT (SEQ ID NO: 13) | ASTE13 hilD::GFPmut2, ASTE13 hilD::mCherry |
| ACGAAATGGCTGGAAAATGGAACGTTCTTTCATTG TTGGCTGTGACGGAAGATCACTTCG (SEQ ID NO: 9) | ASTE13 hilE |
| GTCCTCATCGCCACAGCGCCTGTCGGTGAAGAGGC CGCCATCAAAGGGAAAACTGTCCAT (SEQ ID NO: 10) | ASTE13 hilE |

TABLE 5-continued

| Primers used in Example 2 | |
| --- | --- |
| Sequence | Used to Construct This Strain |
| ATGGCTGGAAAATGGAACGTTCTTTCATTGTTGGC GGCGGCCTCTTCACCGACAGGCGCTGTGGCGATGA (SEQ ID NO: 11) | ASTE13 hilE |
| TTATAATTTCATTACGGTTTAAGTAAAGACTTATAT TCAGTGTGACGGAAGATCACTTCG (SEQ ID NO: 14) | ASTE13 avrA |
| AAGTTAAAGATGATATTTTCGGTGCAGGAGCTATC ATGTGATCAAAGGGAAAACTGTCCATAT (SEQ ID NO: 15) | ASTE13 avrA |
| TTTCATTACGGTTTAAGTAAAGACTTATATTCAGCA CATGATAGCTCCTGCACCGAAAATATCATCTTTA (SEQ ID NO: 16) | ASTE13 avr A |
| AGGAATTCTAATGAAGATATCATCAGGCGCAATTA ATTTTTGTGACGGAAGATCACTTCG (SEQ ID NO: 17) | ASTE13 sopA |
| TGAGGCTGGACTACGCCCAGGCCAGTGGCAGGATG GATGAATCAAAGGGAAAACTGTCCATAT (SEQ ID NO: 18) | ASTE13 sopA |
| TTCTAATGAAGATATCATCAGGCGCAATTAATTTTT CATCCATCCTGCCACTGGCCTGGGCGTAGTCCAG (SEQ ID NO: 19) | ASTE13 sopA |
| ACGTATTAAATTATGCATAATGCTCTTTCAATTGCT TCACTGTGACGGAAGATCACTTCG (SEQ ID NO: 20) | ASTE13 sopB |
| TAAAAACGCTATGCAAATACAGAGCTTCTATCACT CAGCTATCAAAGGGAAAACTGTCCATAT (SEQ ID NO: 21) | ASTE13 sopB |
| TTAAATTATGCATAATGCTCTTTCAATTGCTTCACA GCTGAGTGATAGAAGCTCTGTATTTGCATAGCGT (SEQ ID NO: 22) | ASTE13 sopB |
| GGAAAATATTATGCCAGTCACTTTAAGCTTCGGTA ATCATTGTGACGGAAGATCACTTCG (SEQ ID NO: 23) | ASTE13 sopD |
| CTGACTATCTTTATGTCAGTAATATATTACGACTGC ACCCATCAAAGGGAAAACTGTCCATAT (SEQ ID NO: 24) | ASTE13 sopD |
| ATATTATGCCAGTCACTTTAAGCTTCGGTAATCATG GGTGCAGTCGTAATATATTACTGACATAAAGATA (SEQ ID NO: 25) | ASTE13 sopD |
| TTTACTACCATCAGGAGGCATTCTGAAGATACTTA TTCGCTGTGACGGAAGATCACTTCG (SEQ ID NO: 26) | ASTE13 sopE2 |
| GAGAACTACCGTGACTAACATAACACTATCCACCC AGCACATCAAAGGGAAAACTGTCCATAT (SEQ ID NO: 27) | ASTE13 sopE2 |
| TACCATCAGGAGGCATTCTGAAGATACTTATTCGC GTGCTGGGTGGATAGTGTTATGTTAGTCACGGTAG (SEQ ID NO: 28) | ASTE13 sopE2 |
| GGAAAGTAAATTGCAAGCACACCAGGATATTATCG CTAATTGTGACGGAAGATCACTTCG (SEQ ID NO: 29) | ASTE13 sptP |
| TATGTTTTTATCAGCTTGCCGTCGTCATAAGCAACT GGGCATCAAAGGGAAAACTGTCCATAT (SEQ ID NO: 30) | ASTE13 sptP ASTE13 pSLT sipBCDAFsicPsptP ASTE13 pSLT sipBCDAFsicPsptP SPI-2 |
| GTAAATTGCAAGCACACCAGGATATTATCGCTAAT GCCCAGTTGCTTATGACGACGGCAAGCTGATAAAA (SEQ ID NO: 31) | ASTE13 sptP |

TABLE 5-continued

| Primers used in Example 2 | |
| --- | --- |
| Sequence | Used to Construct This Strain |
| GCTTCCTGCAAGGATAACAGAAGAGGATATTAATA ATGGTTACAAGTGTATGTGACGGAAGATCACTTCG (SEQ ID NO: 32) | ASTE13 sipA |
| TCAATATCCATATTCATCGCATCTTTCCCGGTTAAT TAACGCTGCATGTGATCAAAGGGAAAACTGTCCAT AT (SEQ ID NO: 33) | ASTE13 sipA |
| CAGTACGATAAGTAGCAGCCTGGAAACCGCCAAA AGCTTCCTGCAAGGATAACAGAAGAGGATATTAAT AATGGTTACAAGTGTACACATGCAGCGTTAA (SEQ ID NO: 34) | ASTE13 sipA |
| CAATACAAGAGGTGATCACTTTTTTGACTCTTGCTT CAATATCCATATTCATCGCATCTTTCCCGGTTAATT AACGCTGCATGTGTACACTTGTAACCAT (SEQ ID NO: 35) | ASTE13 sipA |
| ACAGAGCAGCACAGTGAACAAGAAAAGGAATAAT TATGGTAAATGACGCATGTGACGGAAGATCACTTC G (SEQ ID NO: 36) | ASTE13 sipB ASTE13 sipBCD ASTE13 pSLT sipBCDAFsicPsptP ASTE13 pSLT sipBCDAFsicPsptP SPI-2 |
| ATTAACATATTTTTCTCCCTTTATTTTGGCAGTTTTT ATGCGCGACTCTGATCAAAGGGAAAACTGTCCATA T (SEQ ID NO: 37) | ASTE13 sipB |
| CGTTGGTCTATCTGGAGGCGCTAAAAACGGCGGAG ACAGAGCAGCACAGTGAACAAGAAAAGGAATAAT TATGGTAAATGACGCACAGAGTCGCGCATAA (SEQ ID NO: 38) | ASTE13 sipB |
| TTAAATAAGCGGCGGGATTTATTCCCACATTACTA ATTAACATATTTTTCTCCCTTTATTTTGGCAGTTTTT ATGCGCGACTCTGTGCGTCATTTACCAT (SEQ ID NO: 39) | ASTE13 sipB |
| GCGCATAAAAACTGCCAAAATAAAGGGAGAAAAA TATGTTAATTAGTAATTGTGACGGAAGATCACTTC G (SEQ ID NO: 40) | ASTE13 sipC |
| TCACACCCATGATGGCGTATAGATGACCTTTCAGA TTAAGCGCGAATATTATCAAAGGGAAAACTGTCCA TAT (SEQ ID NO: 41) | ASTE13 sipC |
| TGCGGATGCTTCGCGTTTTATTCTGCGCCAGAGTCG CGCATAAAAACTGCCAAAATAAAGGGAGAAAAAT ATGTTAATTAGTAATAATATTCGCGCTTAA (SEQ ID NO: 42) | ASTE13 sipC |
| AAATATCCCCAGTTCGCCATCAGGAGCGCGATTAAA TCACACCCATGATGGCGTATAGATGACCTTTCAGA TTAAGCGCGAATATTATTACTAATTAACAT (SEQ ID NO: 43) | ASTE13 sipC |
| TTTAATCGCGCTCCTGATGGCGAACTGGGGATATT ATGCTTAATATTCAATGTGACGGAAGATCACTTCG (SEQ ID NO: 44) | ASTE13 sipD |
| CTTACACTTGTAACCATTATTAATATCCTCTTCTGT TATCCTTGCAGGAAATCAAAGGGAAAACTGTCCAT AT (SEQ ID NO: 45) | ASTE13 sipD ASTE13 sipBCD |
| TCTGAAAGGTCATCTATACGCCATCATGGGTGTGA TTTAATCGCGCTCCTGATGGCGAACTGGGGATATT ATGCTTAATATTCAATTCCTGCAAGGATAA (SEQ ID NO: 46) | ASTE13 sipD |
| TCTGCATACCTGGCATTATGACGGGGGGCTGAGTC CTTACACTTGTAACCATTATTAATATCCTCTTCTGT TATCCTTGCAGGAATTGAATATTAAGCAT (SEQ ID NO: 47) | ASTE13 sipD |

TABLE 5-continued

Primers used in Example 2

| Sequence | Used to Construct This Strain |
|---|---|
| TGGTCTATCTGGAGGCGCTAAAAACGGCGGAGACA GAGCAGCACAGTGAACAAGAAAAGGAATAACAGA AGAGGATATTAATAATGG (SEQ ID NO: 48) | ASTE13 sipBCD |
| GGTCTGCATACCTGGCATTATGACGGGGGGCTGAG TCCTTACACTTGTAACCATTATTAATATCCTCTTCT GTTATTCCTTTTCTTG (SEQ ID NO: 49) | ASTE13 sipBCD |
| TGTGTAATTCAAGGGAAATCCATGAAACATAAATT AATGATGTGACGGAAGATCACTTC (SEQ ID NO: 50) | ASTE13 fim |
| GGATATTTTTTTATGCTGCGTATCGCTATTAAGGAA ATCAAAGGGAAAACTGTCCATATG (SEQ ID NO: 51) | ASTE13 fim |
| AAGGGAAATCCATGAAACATAAATTAATGATTCCT TAATAGCGATACGCAGCATAAAAAA (SEQ ID NO: 52) | ASTE13 fim |
| ACCGTTTCGGTTAAACAGCCTGTTCGATCTGTTCAT CCAGTGTGACGGAAGATCACTTCG (SEQ ID NO: 53) | ASTE13 flhDC |
| GTGTAAGGCGAATCTCAGTGGGAGGCTGCGTTATA CGTCATCAAAGGGAAAACTGTCCAT (SEQ ID NO: 54) | ASTE13 flhDC |
| TTAAACAGCCTGTTCGATCTGTTCATCCAGGACGT ATAACGCAGCCTCCCACTGAGATTC (SEQ ID NO: 55) | ASTE13 flhDC |
| GTAATATCAGGAGACAACATGGAAGACGAAAGTA ATCCGTTGTGACGGAAGATCACTTC (SEQ ID NO: 56) | ASTE13 SPI-4 |
| TGCGTCACCATGATCAACGTTTTCCCATGAATAAA CATCAAAGGGAAAACTGTCCATATG (SEQ ID NO: 57) | ASTE13 SPI-4 |
| GAGACAACATGGAAGACGAAAGTAATCCGTGTTTA TTCATGGGAAAACGTTGATCATGGT (SEQ ID NO: 58) | ASTE13 SPI-4 |
| CCCGATGTGTCTATTTATTGAAGATGTAGACCATTC TGGGTGTGACGGAAGATCACTTCG (SEQ ID NO: 59) | ASTE13 SPI-5 |
| TGGGAACCTTTATGAAAAAGTATCTTGCATTCGCC GATCAAAGGGAAAACTGTCCATATG (SEQ ID NO: 60) | ASTE13 SPI-5 |
| CTATTTATTGAAGATGTAGACCATTCTGGGCGGCG AATGCAAGATACTTTTTCATAAAGG (SEQ ID NO: 61) | ASTE13 SPI-5 |
| TTATGGTAAATGACGCAAGTAGCATTAGCCGTAGC GCCCAGTTGCTTATGACGACGGCAAGCTGATAAAA (SEQ ID NO: 151) | ASTE13 pSLT sipBCDAFsicPsptP ASTE13 pSLT sipBCDAFsicPsptP SPI-2 |
| CCGCGAAGCGGTCGACGTTACCGGTGGCGAACGCC GCAAA TGTGACGGAAGATCACTTC (SEQ ID NO: 152) | ASTE13 pSLT sipBCDAFsicPsptP SPI-2 |
| CCACAGTAGCAACTATTACCCCAGCGCCCAGAAAC A ATCAAAGGGAAAACTGTCCATATG (SEQ ID NO: 153) | ASTE13 pSLT sipBCDAFsicPsptP SPI-2 |
| GTCGACGTTACCGGTGGCGAACGCCGCAAATGTTT CTGGGCGCTGGGGTAATAGTTGCTA (SEQ ID NO: 154) | ASTE13 pSLT sipBCDAFsicPsptP SPI-2 |

Protein Separation and Western Blotting

Samples were separated by SDS-PAGE and transferred to a polyvinylidene fluoride membrane (PVDF, Millipore) for western blotting using the Bio-Rad Criterion blotter. Membranes were probed with mouse anti-FLAG per manufac-turer's instructions (Sigma Aldrich). To facilitate chemilu-minescent detection, a secondary labeling step was performed with goat anti-mouse IgG (H+L) HRP conjugate according to manufacturer's instructions (Thermo Fisher). Bands were detected with the SuperSignal West Pico Plus substrate (Thermo Fisher) and a ChemiDoc XRS+imaging system (Bio-Rad). All relative protein quantities were calculated by performing densitometry using Image Lab software (Bio-Rad) and normalizing to the specified condition. Coomassie staining was performed according to Studier [153].

Flow Cytometry

Strains were grown and induced as specified in "Strains and Growth Conditions". Samples were prepared by diluting cultures to an optical density at 600 nm of 0.005 to 0.05 in PBS with 1 mg/mL kanamycin in sterile round bottom tubes (Fisher #14-956-3B) and stored at 4° C. for analysis. For each sample, an Attune NXT flow cytometer (Life Technologies) was used to collect 10,000 events within a gated population determined to be cells. Data was analyzed using FlowJo 10.5.3 (TreeStar, Inc.).

Example 3

This Example describes further optimization of the growth media for increasing protein secretion titer from the recombinant T3SS system. In this Example, we screened common rich bacterial growth media and found that carbon source choice, buffering agents, and ionic content were critical factors for T3SS activity and secretion titer. We found that individually, non-ionic carbon sources repressed secretion via the T3SS while high ionic content increased secretion titers. The combination of a carbon source, a buffering agent, and high ionic content, however, had a synergistic effect to boost secretion titer further. SPI-1 T3SS transcriptional activity showed that this optimal combination increased secretion titer in part by elevating transcriptional activity and prolonging secretion system activation. An optimized combination of glycerol, potassium phosphate, and sodium chloride in LB medium increased secretion titer at least fourfold for several model proteins.

Results

Secretion Titer Increases with Ionic Content

Phosphate is a unique buffer species because in addition to providing buffer capacity, it contributes significantly to the ionic content of the media. To decouple the effects of buffering and increased ionic content, we compared secretion titer in media containing a base of 10 g/L tryptone and 5 g/L yeast extract supplemented with a range of concentrations of potassium phosphate, MOPS, sodium chloride, or MOPS supplemented with sodium chloride (Table 6). We selected MOPS as an alternative buffer species because it is the main buffer component in a defined medium explicitly designed for S. enterica cultivation [157], it has a minimal contribution to ionic strength, and it is one of Good's buffers [158]. To mimic the simultaneous contributions of buffering and ionic content inherent to phosphate, we supplemented MOPS with sodium chloride. Finally, sodium chloride changes ionic content without a buffering effect. We monitored ionic content by measuring conductivity. The concentrations of sodium chloride with and without MOPS were chosen to match the conductivities of the specified concentrations of potassium phosphate. Expression and secretion titer were compared to LB-L with no additives using semi-quantitative western blotting.

TABLE 6

| | [KH₂PO₄/ | | | |
|---|---|---|---|---|
| | K₂HPO₄] | [MOPS] | [NaCl] | Conductivity |
| Medium | (mM) | (mM) | (mM) | (mS/cm) |
| 1 | 10 | 0 | 0 | 4.0 |
| 2 | 20 | 0 | 0 | 5.6 |
| 3 | 40 | 0 | 0 | 8.4 |
| 4 | 80 | 0 | 0 | 14 |
| 5 | 160 | 0 | 0 | 25 |
| 6 | 0 | 10 | 0 | 2.5 |
| 7 | 0 | 20 | 0 | 2.8 |
| 8 | 0 | 40 | 0 | 3.5 |
| 9 | 0 | 80 | 0 | 4.7 |
| 10 | 0 | 160 | 0 | 7.1 |
| 11 | 0 | 10 | 12 | 3.8 |
| 12 | 0 | 20 | 24 | 5.4 |
| 13 | 0 | 40 | 48 | 8.1 |
| 14 | 0 | 80 | 97 | 14 |
| 15 | 0 | 160 | 193 | 23 |
| 16 | 0 | 0 | 14 | 3.5 |
| 17 | 0 | 0 | 28 | 4.9 |
| 18 | 0 | 0 | 56 | 7.5 |
| 19 | 0 | 0 | 112 | 13 |
| 20 | 0 | 0 | 224 | 23 |
| LB-L | 0 | 0 | 86 | 11 |
| LB-IM | 0 | 0 | 291 | 31 |

Medium additives for FIGS. 7A-7B.

Figures 7A, 7B:
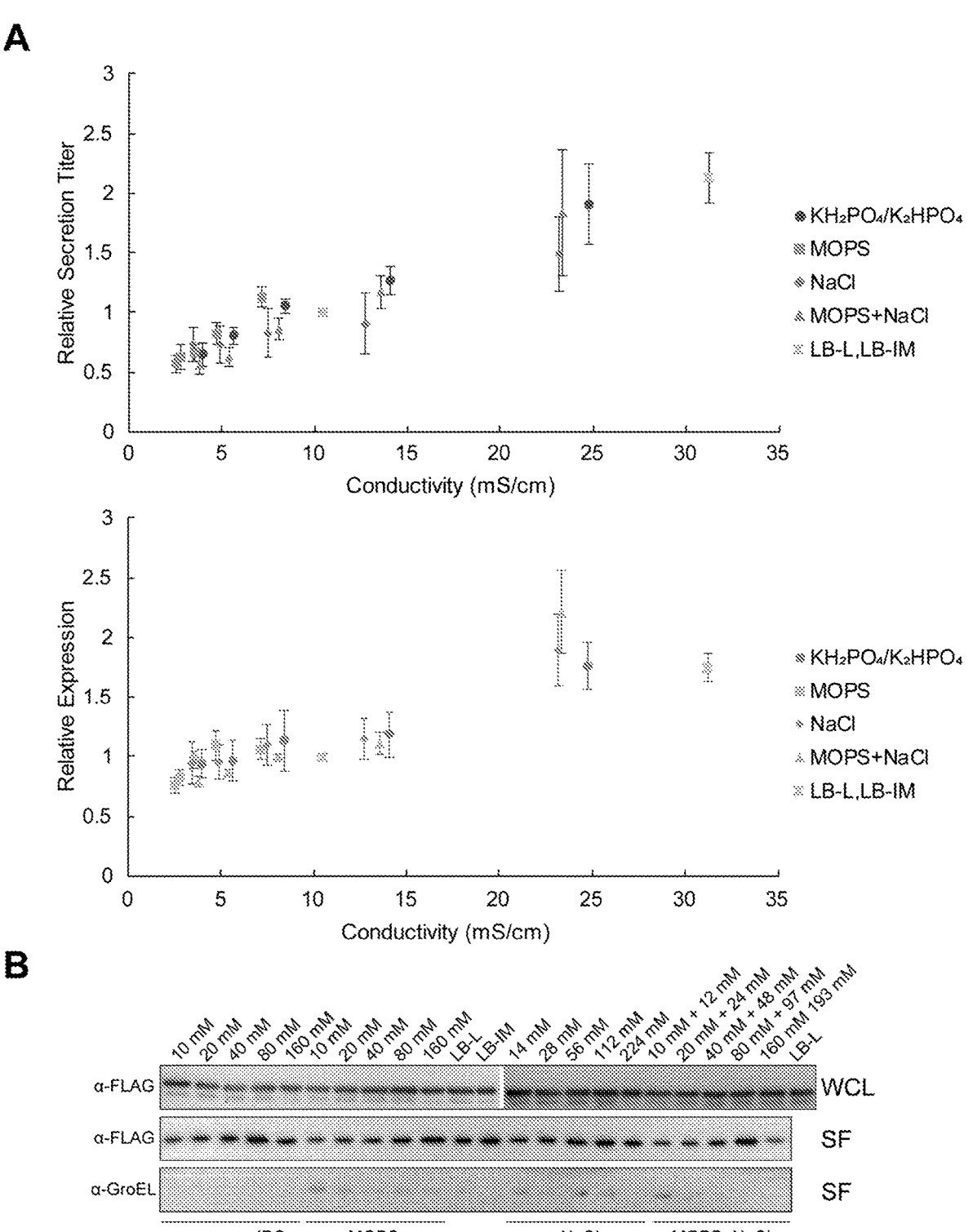
FIGS. 7A-7B. Expression and secretion increase with ionic content. (A) Relative bulk secretion titer (left) and expression (right) of SptP-DH-2×FLAG in media containing 10 g/L tryptone, 5 g/L yeast extract, and the additives specified in Table 6 plotted versus medium conductivity. Bulk expression and secretion titer were normalized to LB-L with no additives (dotted lines). Error bars represent one standard deviation. (B) Western blots are representative of three biological replicates. Samples at the highest additive concentrations were diluted 0.5× to fall within the linear range of the LB-L signal. Boxed bands are from the same blot but were rearranged for clarity. "WCL" is whole culture lysate and "SF" is the secreted fraction.
Figure 9:
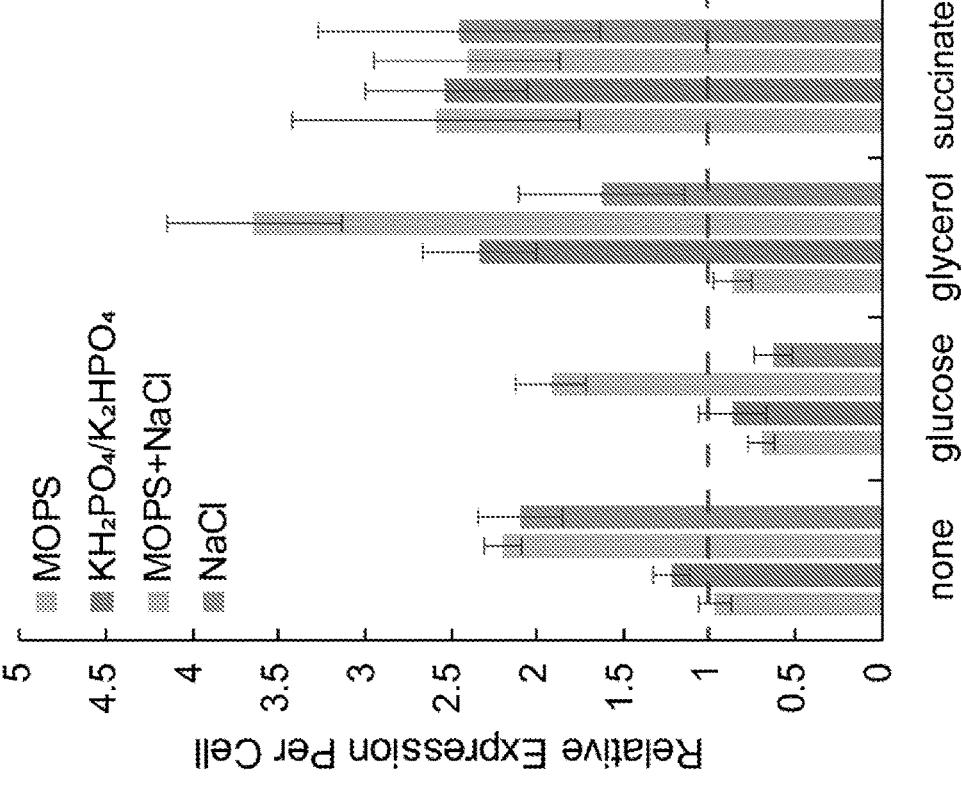
FIG. 9. Expression and secretion per cell vary among combinations of buffers, salts and carbon sources. (left) Relative secretion titer per cell and (right) relative expression per cell of SptP-DH-2×FLAG-6×His in the media listed in Table 7. This is the same data set as FIGS. 8A-8B. Expression and secretion per cell were calculated by dividing densitometry by $OD_{600nm}$ and normalizing to LB-L with no additives. Error bars represent one standard deviation for three biological replicates.
Figure 9:
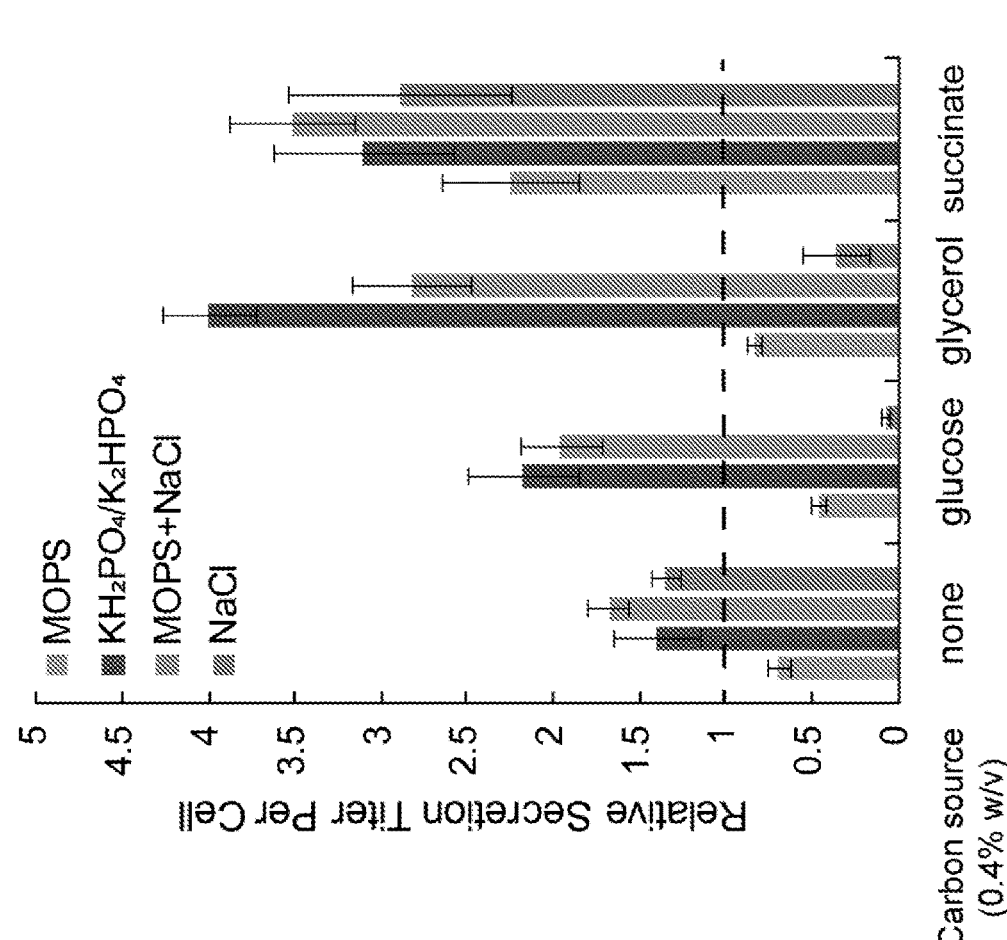

Expression and secretion titer increased linearly with conductivity (FIGS. 7A-7B). The correlation was stronger for secretion titer ($R^2=0.9$) than expression ($R^2=0.8$). LB-IM and the highest concentrations of potassium phosphate and MOPS+NaCl provided the highest secretion titers. Expression was maximal in the highest concentrations of sodium chloride, MOPS+NaCl, and potassium phosphate.

Carbon Sources and Buffers have a Synergistic Effect on Expression and Secretion Titer Independent addition of buffers, salts and carbon sources showed that secretion titer increases with ionic content and decreases with carbon sources that cause acidification of the culture. If acidification of the culture was the sole cause of decreased secretion titer, addition of a buffer would return secretion titer to levels at least equivalent to no added carbon source. Potassium phosphate and glycerol in LB-L had a synergistic effect, however, suggesting that high ionic strength, buffering, and added carbon sources are a critical combination for increased secretion titer.

To determine if the synergistic effect could be a result of any combination of carbon source and buffer at high ionic strength or whether the effect was specific to the combination of phosphate and glycerol, we measured secretion of SptP-DH-2×FLAG-6×His in LB media containing potassium phosphate, MOPS, sodium chloride, and MOPS plus sodium chloride with added glycerol, glucose, or succinate. The potassium phosphate and MOPS concentrations were 90 mM to match the concentration of potassium phosphate in TB, and the concentrations of sodium chloride with and without MOPS buffer were chosen to approximate the conductivity of 90 mM potassium phosphate (Table 7). Expression and secretion titer of SptP-DH-2×FLAG-6×His were measured in comparison to LB-L with no added carbon source using semi-quantitative western blotting.

TABLE 7

| | [KH$_2$PO$_4$/ K$_2$HPO$_4$] | [MOPS] | [NaCl] | Conductivity (mS/cm) | | | |
|---|---|---|---|---|---|---|---|
| Medium | (mM) | (mM) | (mM) | None | Glucose | Glycerol | Succinate |
| KH$_2$PO$_4$/K$_2$HPO$_4$ | 90 | 0 | 0 | 14 | 14 | 14 | 18 |
| MOPS | 0 | 90 | 0 | 5.0 | 5.4 | 5.4 | 9.9 |
| MOPS + NaCl | 0 | 90 | 199 | 20 | 20 | 20 | 24 |
| NaCl | 0 | 0 | 234 | 22 | 22 | 21 | 26 |

Conductivity of LB supplemented with buffers, salts, and carbon sources.

Figures 8A, 8B:
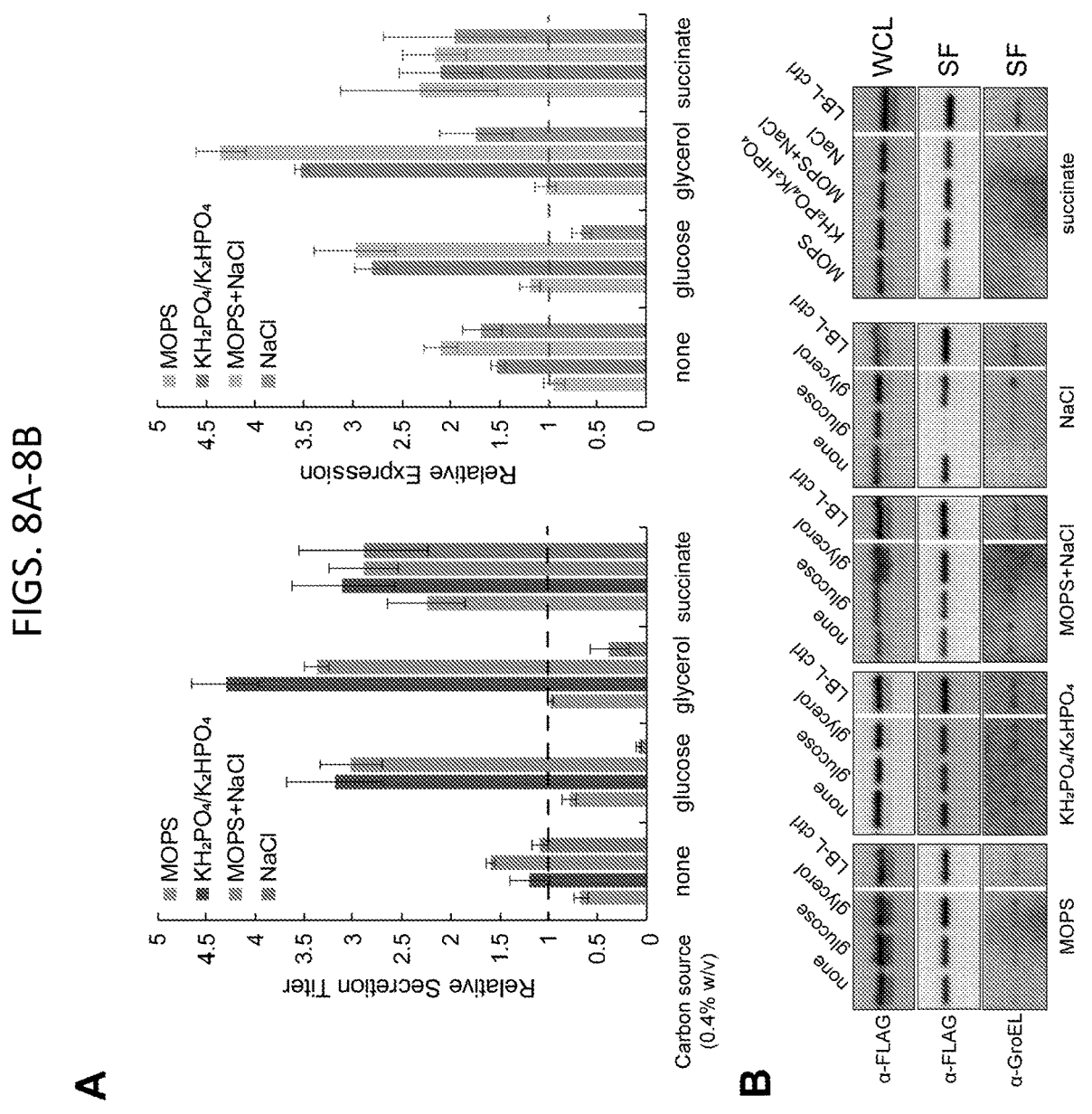

Buffering was essential to maintain secretion in the presence of glucose and glycerol, and the combination of buffering and increased ionic content was necessary to increase expression and secretion titer (FIG. 8A). LB-MOPS with glucose or glycerol produced secretion titers similar to LB-L with no added carbon source, while secretion titer decreased in LB-NaCl with glucose or glycerol. The decrease in secretion was likely due to acidification of the extracellular environment (Table 8). Both LB-(KH$_2$PO$_4$/K$_2$HPO$_4$) and LB-(MOPS+NaCl) with added glucose or glycerol provided at least a threefold increase in secretion titer. The combination of phosphate and glycerol appeared to have a specific beneficial effect on secretion titer—it provided the largest increase in secretion titer even though expression in LB-(MOPS+NaCl) with glycerol increased by a larger margin (FIG. 8B).

Figures 10A, 10B, 10C:
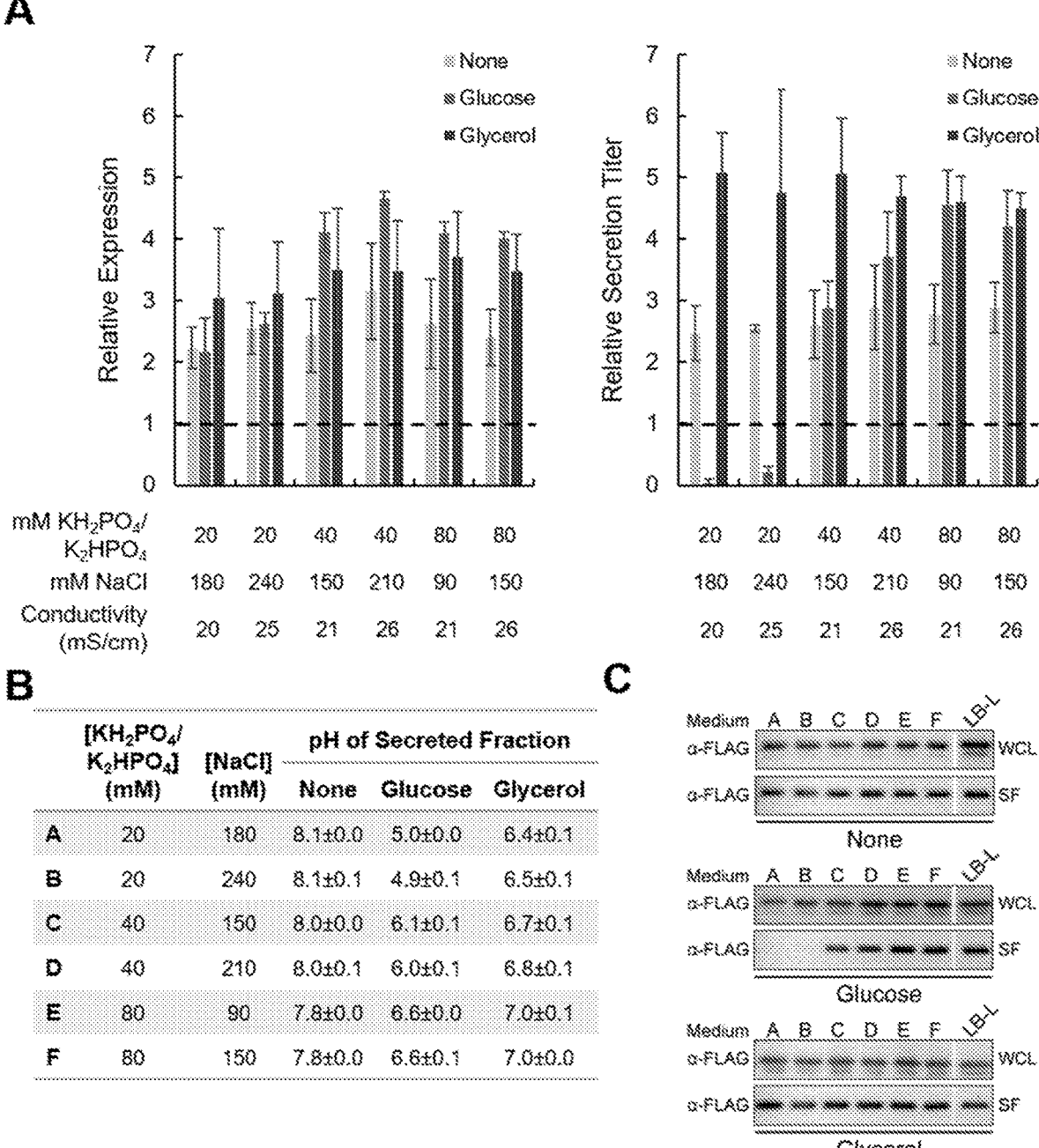
FIGS. 10A-10C. An ideal medium formulation includes glycerol, phosphate, and sodium chloride. (A) Relative bulk expression (left) and secretion titer (right) of SptP-DH-2× FLAG-6×His media with 10 g/L tryptone, 5 g/L yeast extract, and the listed additives at pH 7.4. Glucose and glycerol were 0.4% w/v. Expression and secretion titer were normalized to LB-L with no additives using semi-quantitative western blotting. Error bars represent one standard deviation. (B) pH of the secreted fractions after harvest. (C) Western blots are representative of three biological replicates. Samples were diluted to fall within the linear range of the LB-L signal. Boxed bands are from the same blot but were rearranged for clarity.
Figure 11A:
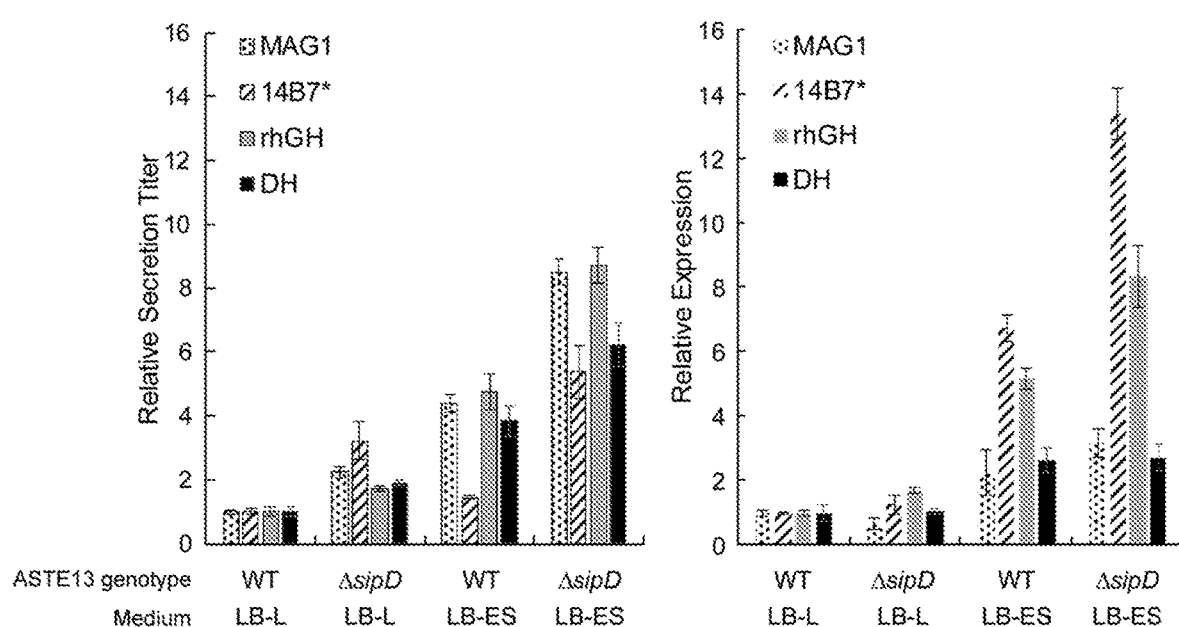
FIGS. 11A-11B. Increases in secretion titer from optimized media and strain modifications are additive. (A) Relative bulk secretion titer (left) and expression (right) of test proteins from WT and ΔsipD strains in LB-L or LB-ES media. "LB-ES" is 10 g/L tryptone, 5 g/L yeast extract, 80 mM $KH_2PO_4/K_2HPO_4$ pH 7.4, 90 mM NaCl, and 0.4% w/v glycerol. Bulk relative expression and secretion titer were normalized to secretion from ASTE13 WT in LB-L for each protein using semi-quantitative western blotting. Error bars represent one standard deviation. (B) Western blots are representative of three biological replicates. Samples were diluted to fall within the linear range of the normalization signal. Boxed bands are from the same blot but were rearranged for clarity.
Figure 11B:
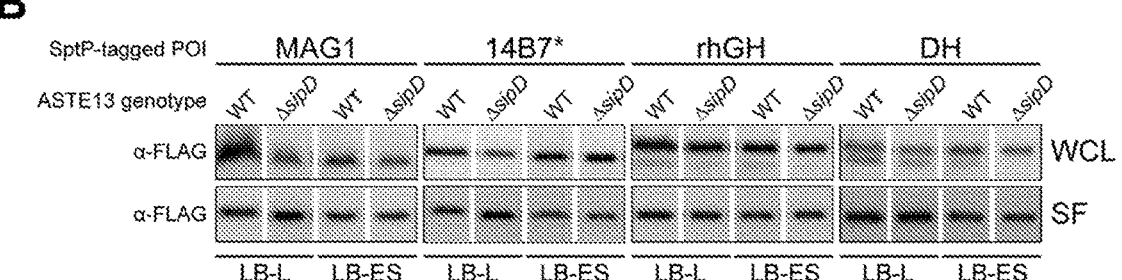
Figures 12A, 12B, 12C:
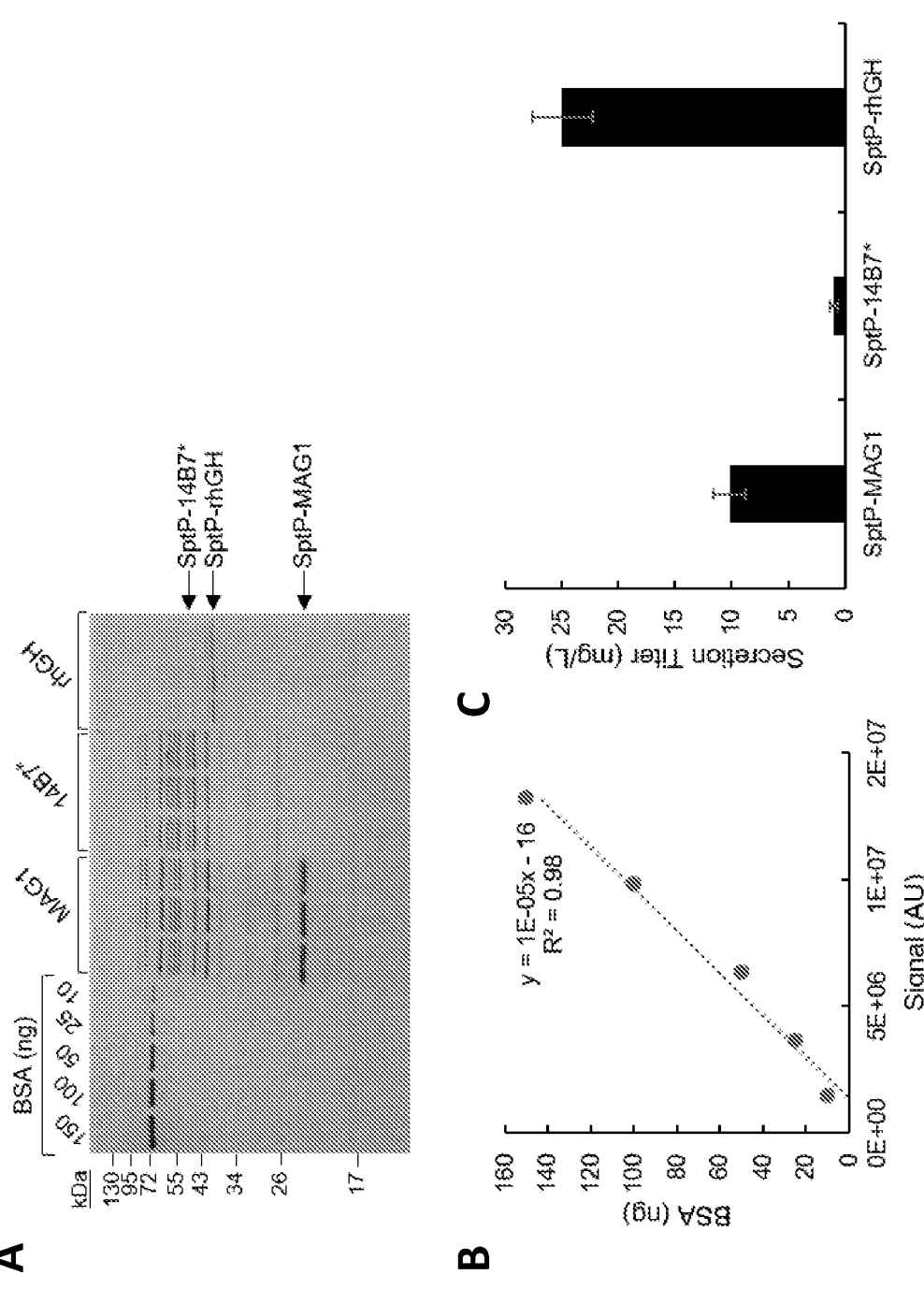
FIGS. 12A-12C. Titer of secreted proteins. MAG1, 14B7*, and rhGH were secreted from an ASTE13 ΔsipD strain in LB-ES as described in the Methods. All proteins were in the format SptP-POI-2×FLAG-6×His. Secretion titer (C) was measured by performing densitometry relative to a BSA standard curve (B) on a Coomassie-stained gel (A). The rhGH secreted fractions were diluted fivefold relative to those of MAG1 and 14B7*. Error bars represent one standard deviation.
Figures 13A, 13B, 13C, 13D, 13E:
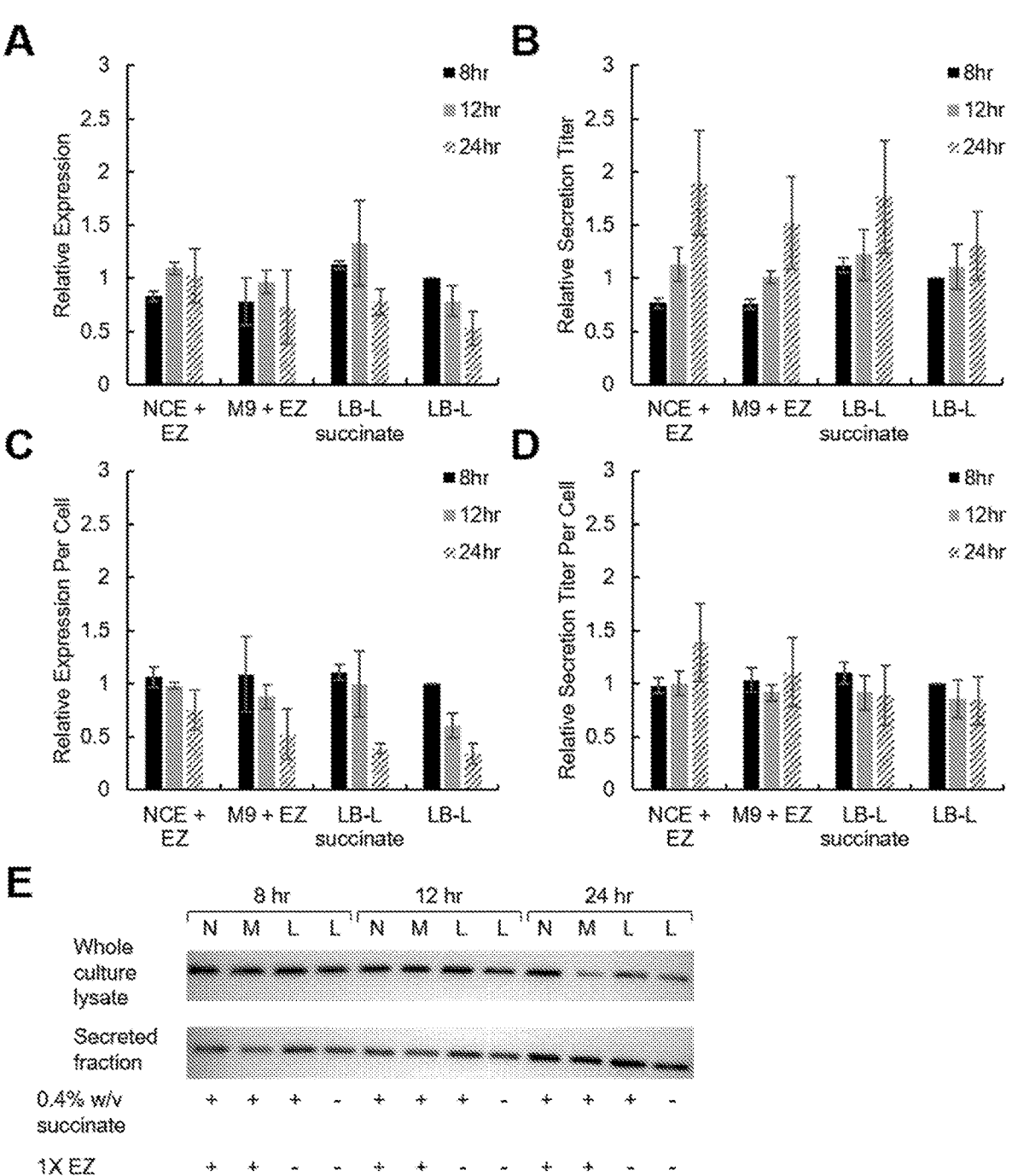
FIGS. 13A-13E. Relative expression and secretion titer in defined media. Relative expression (A,C) and secretion titer (B,D) of SptP-Bla-2×FLAG-6×His in NCE and M9 containing 1×EZ Supplement and 0.4% w/v succinate were compared to LB-L with 0.4% w/v succinate and un-supplemented LB-L. Values represent densitometry on semi-quantitative western blots normalized to LB-L at 8 hours. "Per cell" values are divided by $OD_{600}$ at the specified time point. Induction of $P_{lacUV5}$ hilA facilitated T3SS and SptP-Bla-2×FLAG-6×His expression. Representative western blots are displayed in (E). "Whole culture lysate" represents total expressed protein. "N", "M", and "L" are NCE, M9, and LB-L.
Figures 15A, 15B, 15C, 15D, 15E:
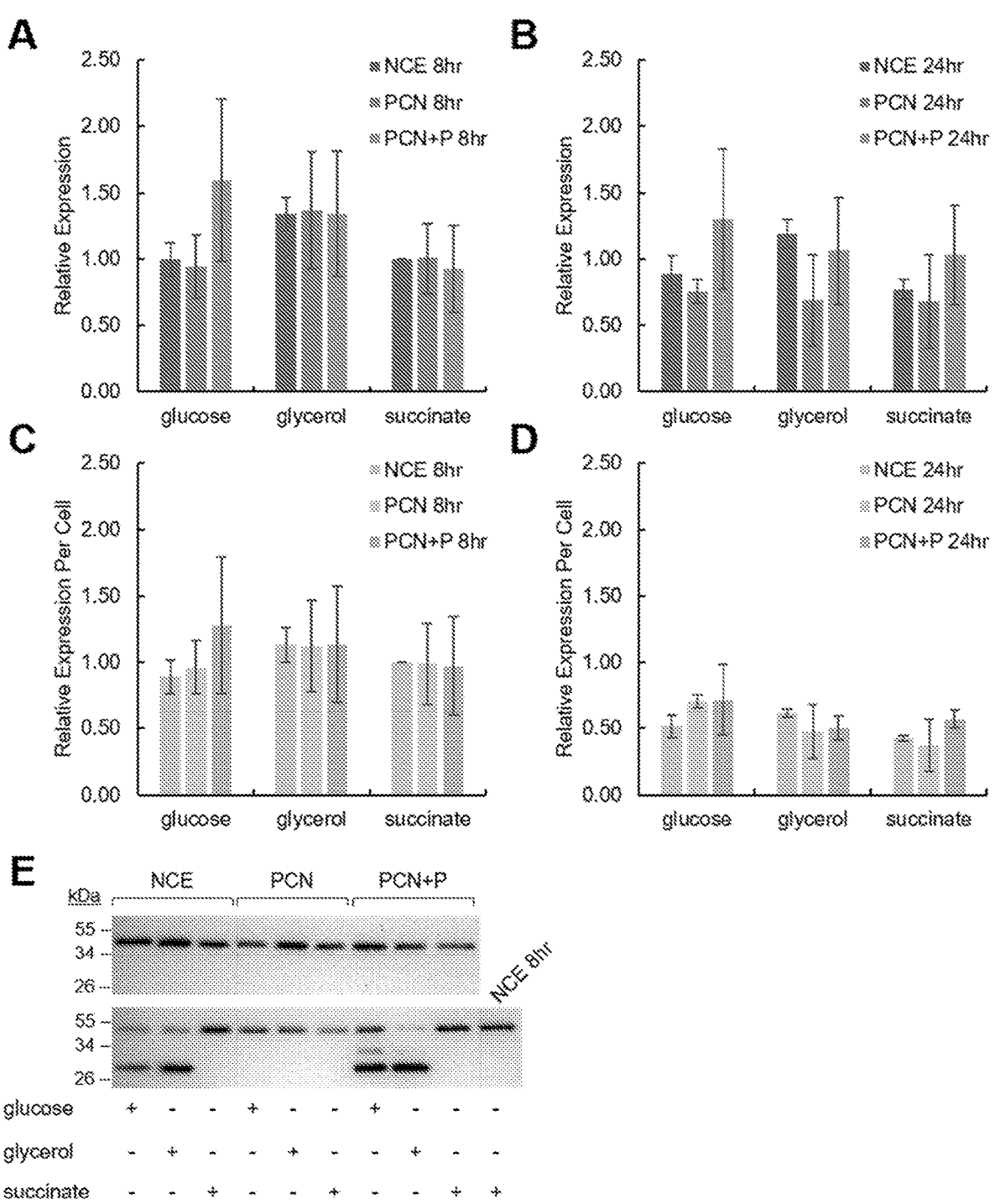
FIGS. 15A-15E. Expression of SptP-Bla-GFP11-2× FLAG-6×His in defined media with glucose, glycerol, or succinate. Expression of SptP-Bla-2×FLAG-6×His was measured in NCE, PCN, and PCN+P at 8 (A, C) and 24 (B, D) hours via semi-quantitative western blotting. Data was normalized to NCE with 0.4% w/v succinate at 8 hours. "Per cell" values are bulk measurements divided by $OD_{600}$ values at the appropriate time point. The T3SS was induced via $P_{lacUV5}$ hilA expression. Representative western blots are shown in (E).
Figures 16A, 16B, 16C, 16D:
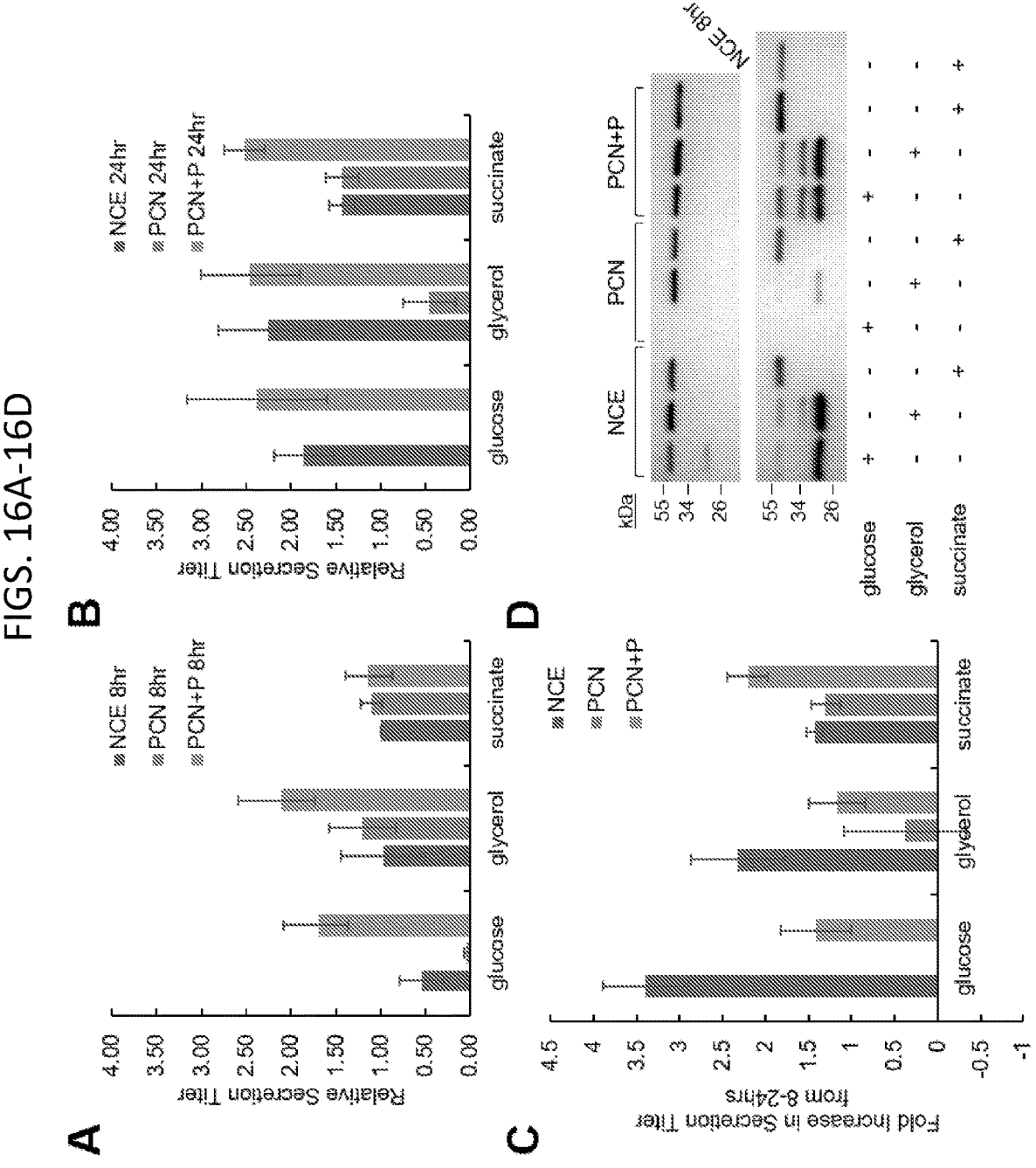
FIGS. 16A-16D. Relative secretion titer of SptP-Bla-GFP11-2×FLAG-6×His in defined media with glucose, glycerol, or succinate. Secretion titer of SptP-Bla-2×FLAG-6×His was measured in NCE, PCN, and PCN+P at 8 (A) and 24 (B) hours via semi-quantitative western blotting. All secretion titers were normalized to NCE with 0.4% w/v succinate at 8 hours. The T3SS was induced via $P_{lacUV5}$ hilA expression. Fold change from 8 to 24 hours was calculated by taking the ratio of relative secretion titers at each time point and propagating error appropriately (C). Representative western blots are shown in (D).

We want to maximize secretion efficiency in addition to bulk secretion titer, so we evaluated expression and secretion on a per cell basis for the combinations of media additives. Total protein expression per cell increased with ionic content if solution pH remained above 5.0 (Table 8) and was highest in LB-(MOPS+NaCl) with glucose and glycerol. Secretion per cell showed a more complex pattern. LB-(KH$_2$PO$_4$/K$_2$HPO$_4$) and LB-(MOPS+NaCl) provided similar increases in secretion per cell in combination with glucose, but glycerol and LB-(KH$_2$PO$_4$/K$_2$HPO$_4$) had a greater synergistic effect than glycerol and LB-(MOPS+ NaCl). Secretion efficiency in LB-(KH$_2$PO$_4$/K$_2$HPO$_4$) was also superior to that in LB-(MOPS+NaCl) with glycerol. Relative secretion per cell was higher than relative bulk secretion for media containing succinate because the high ionic strength of those media limited cell density.

results of FIGS. 7A-7B suggest that the increased conductivity could be responsible for the higher secretion titer. To evaluate the impact of the ratio of potassium phosphate and sodium chloride, we chose two conductivity levels and added the appropriate amount of sodium chloride to 20, 40, or 80 mM potassium phosphate in a base of 10 g/L tryptone and 5 g/L yeast extract to achieve the specified conductivity. We compared expression and secretion of SptP-DH-2× FLAG-6×His in those six media with no added carbon source, 0.4% w/v glucose, and 0.4% w/v glycerol (FIGS. 10A-10C).

Expression was highest in media with 40 mM or 80 mM KH$_2$PO$_4$/K$_2$HPO$_4$ and glucose. Secretion titer was consistent across all media with no added carbon source. Secretion titer in media with glucose varied—secretion titer was negligible in media with 20 mM KH$_2$PO$_4$/K$_2$HPO$_4$, equal to no added carbon source in media with 40 mM KH$_2$PO$_4$/ K$_2$HPO$_4$, and increased fivefold in combination with 80 mM KH$_2$PO$_4$/K$_2$HPO$_4$. Glycerol provided a fivefold increase in all media, though variability was higher in media with lower concentrations of potassium phosphate. The correlation between the pH of the secreted fraction and secretion titer matched the results of FIGS. 8A-8B, and Table 8—when the pH of the secreted fraction dropped below 6.0, secretion titer decreased dramatically.

Increases in Secretion Titer from Optimized Growth Media and Strain Improvements are Additive and General for Diverse Secreted Proteins We previously showed that knocking out a protein in the SPI-1 T3SS tip complex, SipD, increased secretion titer twofold in strains with hilA overexpression [52]. An ideal T3SS production platform would combine all features that

TABLE 8

| | [KH$_2$PO$_4$/ K$_2$HPO$_4$] | [MOPS] | [NaCl] | pH of Secreted Fraction | | | |
|---|---|---|---|---|---|---|---|
| Medium | (mM) | (mM) | (mM) | None | Glucose | Glycerol | Succinate |
| MOPS | 0 | 90 | 0 | 7.6 ± 0.0 | 6.7 ± 0.1 | 6.8 ± 0.0 | 7.6 ± 0.2 |
| KH$_2$PO$_4$/K$_2$HPO$_4$ | 90 | 0 | 0 | 7.5 ± 0.0 | 6.5 ± 0.0 | 6.6 ± 0.0 | 7.6 ± 0.1 |
| MOPS + NaCl | 0 | 90 | 199 | 7.3 ± 0.0 | 6.3 ± 0.0 | 6.8 ± 0.0 | 7.4 ± 0.1 |
| NaCl | 0 | 0 | 234 | 7.9 ± 0.1 | 4.6 ± 0.0 | 4.8 ± 0.0 | 8.0 ± 0.1 | pH of the Secreted Fraction from FIGS. 8A-8B.

An Ideal Medium Formulation Includes Glycerol, Phosphate, and Sodium Chloride

Of the media tested in this work, secretion titer was highest in TB and LB-L with 0.4% w/v glycerol and 89 mM KH$_2$PO$_4$/K$_2$HPO$_4$. The conductivity of LB-L supplemented with glycerol and 89 mM KH$_2$PO$_4$/K$_2$HPO$_4$ was 21 mS/cm, which is higher than the 14 mS/cm measured for the LB-(KH$_2$PO$_4$/K$_2$HPO$_4$) medium listed in Table 7. The increase secretion titer, so we evaluated if ΔsipD was additive with an optimized medium. To determine if the effect was general, we selected a variety of test proteins in addition to DH: magainin-1 (MAG1), an antimicrobial peptide; 14B7*, an scFv against the protective antigen of the anthrax toxin [159,160]; and recombinant human growth hormone (rhGH, mature somatropin). All proteins were cloned in the format SptP-POI-2×FLAG-6×His and secreted in ASTE13 WT and ΔsipD strains in Medium "E" from FIG. 10B (LB-ES for "enhanced secretion").

The ΔsipD strain improvement and the optimized medium were indeed additive for all proteins tested (FIGS. 10A-10C). Secretion titer increased by varying amounts, but the minimum increase provided by the combination of ΔsipD and LB-ES was six-fold above a WT strain in LB-L. Total protein expression showed a different pattern from secretion titer. SptP-MAG1-2×FLAG-6×His and SptP-DH-2×FLAG-6×His followed similar expression patterns, and the apparent effect of ΔsipD and LB-ES was to increase secretion efficiency for these proteins. SptP-rhGH-2×FLAG-6×His and SptP-14B7*-2×FLAG-6×His increased by a surprising eight- and fourteen-fold, however. SptP-rhGH-2×FLAG-6×His expression increased by the same fraction as secretion titer in each condition, suggesting that secretion titer increased with expression while secretion efficiency was unchanged. SptP-14B7*-2×FLAG-6×His secretion titer increased by a much smaller margin than expression in both WT and ΔsipD strains with LB-ES. We hypothesize that the discrepancy was caused by loss of expressed protein to insoluble aggregates, preventing secretion.

Methods

Strains and Growth Conditions

Strains and plasmids used in this work are listed in Table 9 and Table 10. Secretion experiments were started by growing a single colony from a fresh streak of a frozen glycerol stock in the lysogeny broth Lennox formulation (10 g/L tryptone, 5 g/L yeast extract, 5 g/L NaCl) with appropriate antibiotics (34 μg/mL chloramphenicol, 50 μg/mL kanamycin) for 12-16 hours overnight in an orbital shaker at 37° C. and 225 rpm. Overnight cultures were diluted 1:100 into the appropriate medium supplemented with 100 μg/mL isopropyl β-D-1-thiogalactopyranoside (IPTG) with appropriate antibiotics. All culturing steps were performed in 24-well deepwell plates (Axygen). Secretion was performed for 8 hours at 37° C. and 225 rpm in an orbital shaker. Whole culture lysate samples for SDS-PAGE were prepared by adding cell suspension to Laemmli buffer at the end of secretion. The secretion fraction was harvested by centrifuging cultures at 4000×g for 10 minutes. SDS-PAGE samples for the secretion fraction were prepared by adding supernatant to Laemmli buffer. All SDS-PAGE samples were boiled at 95° C. for 5 minutes immediately after preparation.

TABLE 9

Strains used in Example 3.

| Strain Name | Comment | Reference |
|---|---|---|
| ASTE13 | LT2-derived lab strain similar to DW01 | This study; DW01 [65] |
| ASTE13 invE::GFPmut2 | GFPmut2 inserted immediately downstream of invE coding sequence | This study |
| ASTE13 prgH::GFPmut2 | GFPmut2 inserted immediately downstream of prgH coding sequence | This study |
| ASTE13 sipC::GFPmut2 | GFPmut2 inserted immediately downstream of sipC coding sequence | This study |
| ASTE13 ΔphoB | phoB knockout | This study |
| ASTE13 ΔsipD | sipD knockout | Based on [52], newly constructed for this study |

TABLE 10

Plasmids used in Example 3.

| Plasmid Name | ORFs under inducible control | | ORI | abR | Reference |
|---|---|---|---|---|---|
| $P_{sic}$ DH | sicP | sptP-DH-2×FLAG-6×His | colE1 | cam | [41] |
| $P_{sic}$ MAG1 | sicP | sptP-MAG1-2×FLAG-6×His | colE1 | cam | This study |
| $P_{sic}$ 14B7* | sicP | sptP-14B7*-2×FLAG-6×His | colE1 | cam | [38] |
| $P_{sic}$ rhGH | sicP | sptP-rhGH-2×FLAG-6×His | colE1 | cam | This study |
| $P_{lacUV5}$ hilA | hilA | hilA | p15a | kan | [41] |

Medium Formulations

"LB" refers to a base medium formulation of 10 g/L tryptone and 5 g/L yeast extract, and "TB" is the standard Terrific Broth formulation: 12 g/L tryptone, 24 g/L yeast extract, 9.4 g/L $K_2HPO_4$, 2.2 g/L $KH_2PO_4$, and 0.4% w/v glycerol. LB-L is 10 g/L tryptone, 5 g/L yeast extract, and 5 g/L NaCl. Carbon sources were prepared as 20% w/v solutions, sterile filtered, and diluted into the medium to final concentrations of 0.4% w/v at the time of subculture. Media with buffers and salts were formulated by autoclaving LB medium at a 1.2× concentration and adding the appropriate volumes of 1M $K_2HPO_4$, 1M $KH_2PO_4$, 1M MOPS, or 5 M NaCl. Ultrafiltered water was added as necessary to achieve a final 1×LB concentration. The pH of all media was adjusted to 7.4 using HCl or NaOH as appropriate. Tryptone and yeast extract were sourced from BD Bacto. Conductivity and pH were measured using a Fisher Scientific accumet AB150 meter.

Plasmid Construction

PCR was performed with Phusion DNA polymerase using the primers listed in Table 11. Golden gate cloning was used to construct plasmids for this study [151]. Genes for proteins to be secreted were inserted into a modified pPROTet. 133 backbone vector (BD Clontech) under the control of the sic promoter [8]. All secretion plasmids expressed the SptP chaperone sicP and the sptP secretion signal (nucleotides 1 to 477). The SptP secretion tag was fused N-terminal to the protein of interest, and 2×FLAG and 6×His tags were fused C-terminal to the protein of interest. The gene for rhGH was ordered from Twist Biosciences with overhangs compatible with golden gate cloning. All cloning was done in E. coli DH10B cells, and all DNA sequences were confirmed by Sanger sequencing (Quintara).

Recombineering

Recombineering was performed in S. enterica Typhimurium ASTE13 as described by Thomason et al. [152]. Briefly, a cat-sacB cassette conferring chloramphenicol resistance and sucrose sensitivity was amplified using primers with 40 bp of homology 5' and 3' to the locus of interest. The GFPmut2 gene was amplified using primers containing the same 40 bp of homology 5' and 3' to the locus of interest as used for the cat-sacB cassette. PCR was performed with Phusion DNA polymerase with the primers listed in Table 11A. S. enterica Typhimurium ASTE13 was first transformed with pSIM6. A first round of recombineering was performed to insert the cat-sacB cassette at the locus of interest, and a second round of recombineering replaced the cat-sacB cassette with an appropriate DNA product. The replacement DNA was GFPmut2 for transcriptional fusions, a 60 bp oligo containing the first and last 30 bp of phoB for the phoB gene knockout, and a 200 bp double-stranded PCR product containing the first and last 30 bp of sipD flanked 5' and 3' by 70 bp of homology to the sipD genetic locus. The genomic modifications were confirmed by Sanger sequencing (Quintara), and the strains were cured of pSIM6. Primers used for recombineering are listed in Table 11A.

TABLE 11A

| Primers used in Example 3. | | |
| --- | --- | --- |
| Sequence | Amplicon | Used to Construct |
| AATGGCAGAACAGCGTCGTACTATTGA AAAGCTGTCTTAAtgtgacggaagatcacttcg (SEQ ID NO: 62) | cat-sacB | ASTE13 invE::gfpmut2 |
| GAGAAAGCAGCACTATAGGTATCCTGT TAATATTAAAatcaaagggaaaactgtccatat (SEQ ID NO: 63) | cat-sacB | ASTE13 invE::gfpmut2 |
| AATGGCAGAACAGCGTCGTACTATTGA AAAGCTGTCTTAAattaaagaggagaaaggtcatg ag (SEQ ID NO: 64) | gfpmut2 | ASTE13 invE::gfpmut2 |
| GTAGAGAAAGCAGCACTATAGGTATCC TGTTAATATTAAAttatttgtatagttcatccatgccat g (SEQ ID NO: 65) | gfpmut2 | ASTE13 invE::gfpmut2 |
| AATGAGCCCAGGCCATTGGTATTTCCC AAGCCCACTTTAAtgtgacggaagatcacttcg (SEQ ID NO: 66) | cat-sacB | ASTE13 prgH::gfpmut2 |
| AAGGTGTTGCCATAATGACTTCCTTAT TTACGTTAAAatcaaagggaaaactgtccatat (SEQ ID NO: 67) | cat-sacB | ASTE13 prgH::gfpmut2 |
| AATGAGCCCAGGCCATTGGTATTTCCC AAGCCCACTTTAAattaaagaggagaaaggtcatg ag (SEQ ID NO: 68) | gfpmut2 | ASTE13 prgH::gfpmut2 |
| ACCAAGGTGTTGCCATAATGACTTCCT TATTTACGTTAAAttatttgtatagttcatccatgccat g (SEQ ID NO: 69) | gfpmut2 | ASTE13 prgH::gfpmut2 |
| ATCCGCACTCGCTGCTATCGCAGGCAA TATTCGCGCTTAAtgtgacggaagatcacttcg (SEQ ID NO: 70) | cat-sacB | ASTE13 sipC::gfpmut2 |
| AATCACACCCATGATGGCGTATAGATG ACCTTTCAGAatcaaagggaaaactgtccatat (SEQ ID NO: 71) | cat-sacB | ASTE13 sipC::gfpmut2 |
| ATCCGCACTCGCTGCTATCGCAGGCAA TATTCGCGCTTAAattaaagaggagaaaggtcatga g (SEQ ID NO: 72) | gfpmut2 | ASTE13 sipC::gfpmut2 |
| TTAAATCACACCCATGATGGCGTATAG ATGACCTTTCAGAttatttgtatagttcatccatgccat g (SEQ ID NO: 73) | gfpmut2 | ASTE13 sipC::gfpmut2 |
| AAATTATGGCGAGACGTATTCTGGTCG TAGAAGATGAGGCtgtgacggaagatcacttcg (SEQ ID NO: 74) | cat-sacB | ASTE13 ΔphoB |
| GGCATTAAAAGCGGGTCGAAAAACGA TACCCTGTCCCGCatcaaagggaaaactgtccat (SEQ ID NO: 75) | cat-sacB | ASTE13 ΔphoB |
| ATGGCGAGACGTATTCTGGTCGTAGAA GATGAGGCGCGGGACAGGGTATCGTTT TTCGACCCGCTTTTAA (SEQ ID NO: 76) | N/A | ASTE13 ΔphoB |
| TTTAATCGCGCTCCTGATGGCGAACTG GGGATATTATGCTTAATATTCAAtgtgacg gaagatcacttcg (SEQ ID NO: 77) | cat-sacB | ASTE13 ΔsipD |
| CTTACACTTGTAACCATTATTAATATCC TCTTCTGTTATCCTTGCAGGAAatcaaaggg aaaactgtccatat (SEQ ID NO: 45) | cat-sacB | ASTE13 ΔsipD |
| TCTGAAAGGTCATCTATACGCCATCAT GGGTGTGATTTAATCGCGCTCCTGATG GCGAACTGGGGATATTatgcttaatattcaattcct gcaaggataa (SEQ ID NO: 46) | self | ASTE13 ΔsipD |

TABLE 11A-continued

| Primers used in Example 3. | | |
|---|---|---|
| Sequence | Amplicon | Used to Construct |
| TCTGCATACCTGGCATTATGACGGGGG GCTGAGTCCTTACACTTGTAACCATTA TTAATATCCTCTTCTGttatccttgcaggaattgaat attaagcat (SEQ ID NO: 47) | self | ASTE13 ΔsipD |

Protein Separation and Western Blotting

Samples were separated by SDS-PAGE and transferred to a polyvinylidene fluoride membrane (PVDF, Millipore) for western blotting using the Bio-Rad Criterion blotter. Samples were diluted such that all band signals were within twofold of the average signal across the blot. Membranes were probed with mouse anti-FLAG per manufacturer's instructions (Sigma Aldrich). To facilitate chemiluminescent detection, a secondary labeling step was performed with goat anti-mouse IgG (H+L) HRP conjugate according to manufacturer's instructions (Thermo Fisher). Bands were detected with the SuperSignal West Pico Plus substrate (Thermo Fisher) and a ChemiDoc XRS+imaging system (Bio-Rad).

Protein Quantification

All relative protein quantities were calculated by performing densitometry using Image Lab software (Bio-Rad) and normalizing to the average of the replicates of the specified normalization condition. Relative protein amounts were corrected for dilution if appropriate. Absolute secretion titers were measured by performing SDS-PAGE, staining with Coomassie according to Studier [153], and calculating densitometry relative to a bovine serum albumin standard curve (Thermo). Background was calculated by averaging the signal at the same molecular weight as the protein of interest across all other lanes containing secreted fractions and then subtracted from the signal of the protein of interest. Error bars are standard deviation on three biological replicates unless otherwise specified.

Flow Cytometry

ASTE13 strains carrying invE::gfpmut2, prgH::gfpmut2, or sipC::gfpmut2 transcriptional fusions and $P_{lacUV5}$ hilA were grown and induced as specified in "Strains and Growth Conditions". Samples were prepared by diluting cultures to an optical density at 600 nm of 0.005 to 0.05 in PBS with 1 mg/mL kanamycin in round-bottom 96-well plates (Greiner Bio-One #650101). Plates were sealed and stored at 4° C. for analysis. For each sample, an Attune NxT flow cytometer (Life Technologies) was used to collect 10,000 events within a gated population determined to be cells. Data was analyzed using FlowJo 10.5.3 (TreeStar, Inc.). The experiment was performed in biological triplicate, and error bars represent standard error.

Example 4

This Example describes additional optimization of the growth media for increasing protein secretion titer from the recombinant T3SS system.

Results

Supplemented Defined Media Produces Secretion Titers Equivalent to LB-L

Adding the 1×EZ supplement to the defined media allowed secretion experiments to proceed on the same timeline as those in LB-L, so the next step was to compare secretion titer. Previously, secretion experiments ended at eight hours because T3SS transcriptional activity decreased in late exponential phase [41,163]. Previous work showed that transcriptional activity was extended in the presence of buffers and carbon sources, however, so the experiment was extended to 24 hours with sampling at 8 and 12 hours. The data in FIGS. 13A-13E show that secretion continues beyond eight hours in defined media and LB-L with 0.4% w/v succinate.

The decrease in relative expression at 24 hours indicates that expression persisted until at least 12 hours in media that contained succinate but ceased sometime before 24 hours. Within error, all media reached an equivalent maximum secretion titer at 24 hours, but the relative titers at 8 and 12 hours suggest that the average rate of secretion was lower in NCE and M9 compared to LB-L with and without succinate.

Glycerol is an Optimal Carbon Source in NCE

I selected NCE as a base medium to study the effect of a panel of carbon sources on secretion titer. NCE is used for growth and study of *S. enterica* Typhimurium [156,164], and it contains a high concentration of phosphate (Table 11B), which should maximize secretion titer according to the results described above.

TABLE 11B

| Defined media | | | | |
|---|---|---|---|---|
| | Amount (mM) | | | |
| | NCE [ ] | M9 | M9 + ferric citrate | PCN [ ] | PCN + P |
| NaCl | 0 | 8.6 | 8.6 | 50 | 50 |
| MgCl₂ | 0 | 0 | 0 | 0.52 | 0.52 |
| MgSO₄ | 1.0 | 1.0 | 1.0 | 0 | 0 |
| Na₂HPO₄ | 0 | 48 | 48 | 0 | 0 |
| NaH₂PO₄ | 0 | 0 | 0 | 0 | 0 |
| NH₄Cl | 0 | 19 | 19 | 9.5 | 9.5 |
| K₂HPO₄ | 34 | 0 | 0 | 1.7 | 34 |
| KH₂PO₄ | 29 | 22 | 22 | 0 | 29 |
| K₂SO₄ | 0 | 0 | 0 | 0.28 | 0.28 |
| FeSO₄ | 0 | 0 | 0 | 0.010 | 0.010 |
| CaCl₂ | 0 | 0.1 | 0.1 | 0.00050 | 0.00050 |
| Na(NH₄)HPO₄ | 17 | 0 | 0 | 0 | 0 |
| Ferric citrate | 0.050 | 0.050 | 0.050 | 0 | 0 |
| MOPS | 0 | 0 | 0 | 40 | 40 |
| Tricine | 0 | 0 | 0 | 4.0 | 4.0 |
| Micronutrients | 0 | 0 | 0 | See below | See below |

Glycerol provided the highest secretion titer, and the identity of the carbon source had a stronger impact on secretion titer than expression (FIGS. 14A-14B). Maltose was a poor carbon source—it supported a low cell density and negligible secretion titer (Table 12A). Glucose and succinate provided equivalent bulk secretion titers, though secretion per cell was higher with added succinate according to $OD_{600}$ values at 8 hours. The relative expression and secretion titers with added glucose, glycerol and succinate matched the trends observed in Example 3.

TABLE 12A

| Optical density at 8 hours in NCE with various carbon sources. | |
| --- | --- |
| Carbon Source | 8 hr $OD_{600}$ |
| arabinose | 3.4 |
| glucose | 3.1 |
| glycerol | 2.9 |
| maltose | 1.7 |
| sorbitol | 3.4 |
| succinate | 2.4 |

A High Phosphate Concentration is Critical for Increased Secretion Titer in Defined Media To build on these results, I supplemented PCN medium with concentrations of $K_2HPO_4$ and $KH_2PO_4$ equivalent to those in NCE to create "PCN+P" medium (Table 12B). I performed secretion for 24 hours, sampling at eight hours, in NCE, PCN, and PCN+P with 0.4% w/v glucose, glycerol, or succinate. The model protein was SptP-Bla-GFP11-2× FLAG-6×His, as I was optimizing a split GFP assay to measure secretion titer in parallel.

TABLE 12B

| Micronutrients in PCN media | |
| --- | --- |
| PCN Micronutrients [ ] | Amount (mM) |
| $(NH_4)_4Mo_7O_{24}$ | $2.9 \times 10^{-7}$ |
| $H_3BO_3$ | $4.0 \times 10^{-5}$ |
| $CoCl_2$ | $3.0 \times 10^{-6}$ |
| $CuSO_4$ | $9.6 \times 10^{-7}$ |
| $MnCl_2$ | $8.1 \times 10^{-6}$ |
| $ZnSO_4$ | $9.7 \times 10^{-7}$ |

Expression was similar across all media at 8 and 24 hours, which was expected based on the results of Example 3 and the composition of NCE, PCN, and PCN+P (FIGS. 15A-15E). PCN with glucose and glycerol showed a slight decrease in relative expression from 8 to 24 hours. The final cell density was lower in these media than other conditions tested. The end pH from the growth curves suggests that the extracellular environment was acidified, though pH was not measured directly. The decrease in relative expression per cell for all media at 24 hours indicated that expression ceased at some point between 8 and 24 hours.

Secretion titer was more variable than expression. The highest secretion titers were recorded in NCE with glycerol and PCN+P with any carbon source at 24 hours (FIGS. 16A-16D). PCN with glucose had low secretion titer at eight hours, likely due to acidification of the extracellular environment. Secretion titer in PCN with glycerol was similar to PCN with succinate at eight hours, but secretion at 24 hours was lower than secretion at eight hours, indicating that the secreted protein had degraded.

Analyzing the fold change in secretion from 8 to 24 hours suggests that secretion rate varied among the media tested (FIG. 16C), as previously observed when comparing secretion in NCE and M9 to LB-L (FIGS. 13A-13E). Secretion rate was highest in PCN+P with glucose or glycerol—secretion titer in those media had nearly reached their maximum values at eight hours. NCE with glycerol, PCN+P with succinate, and PCN+P with glucose or glycerol achieved similar secretion titers at 24 hours, but secretion rate was about twofold slower in NCE with glycerol and PCN+P with succinate. NCE with glucose had the lowest secretion rate of media that provided increased secretion titer.

Methods

Strains and Growth Conditions

Strains and plasmids used are listed in Table 13 and Table 14. Defined media formulations were as listed in tables above (11B and 12B). Carbon sources were added as specified. Secretion experiments were started by growing a single colony from a fresh streak of a frozen glycerol stock in the lysogeny broth Lennox formulation (LB-L: 10 g/L tryptone, 5 g/L yeast extract, 5 g/L NaCl) with appropriate antibiotics (34 μg/mL chloramphenicol, 50 μg/mL kanamycin) for 12-16 hours overnight in an orbital shaker at 37° C. and 225 rpm. For secretion experiments, overnight cultures were diluted 1:100 into the appropriate medium. All media were supplemented with 100 μg/mL isopropyl β-D-1-thiogalactopyranoside (IPTG) and appropriate antibiotics. All culturing steps were performed in 24-well deepwell plates (Axygen). Secretion was performed for the time specified at 37° C. and 225 rpm in an orbital shaker. Whole culture lysate samples for total protein expression were prepared for SDS-PAGE by adding cell suspension to Laemmli buffer [150] in a 1:2 ratio prior to centrifugation. The secretion fraction was harvested by centrifuging cultures at 4000×g for 10 minutes. SDS-PAGE samples for the secreted fraction were prepared by adding supernatant to Laemmli buffer in a 3:1 ratio [150]. All SDS-PAGE samples were boiled at 95° C. for 5 minutes immediately after preparation.

For growth curves, 1 mL of overnight culture was pelleted at 5000×g for 5 minutes. The supernatant was discarded, and cells were resuspended in 1 mL of the medium used for the growth curve. The resuspended cells were diluted to the specified OD in 5 mL of the appropriate medium supplemented with appropriate antibiotics. All culturing steps were performed in 24-well deepwell plates (Axygen). 100 μL samples were taken hourly for $OD_{600}$ measurement and diluted in $H_2O$ to fall within an $OD_{600}$ range of 0.2-0.8. Growth rates were calculated by identifying the linear region (with a minimum of three time points) and calculating the slope via linear regression. Doubling time was calculated with $t_D = \log(2)/\text{slope}$.

TABLE 13

| Strains used in Example 4. | | |
| --- | --- | --- |
| Strain Name | Comment | Reference |
| ASTE13 | LT2-derived lab strain similar to DW01 | This study; DW01 [65] |
| ASTE13 ΔprgI | prgI knockout | [41] |

TABLE 14

Plasmids used in Example 4.

| Plasmid Name | | ORFs under inducible control | ORI | abR | Reference |
|---|---|---|---|---|---|
| $P_{sic}$ bla | sicP | sptP-bla-2xFLAG-6xHis | colE1 | cam | [41] |
| $P_{sic}$ DH-GFP11 | sicP | sptP-DH-GFP11-2xFLAG-6xHis | colE1 | cam | This study |
| $P_{sic}$ bla-GFP11 | sicP | sptP-bla-GFP11-2xFLAG-6xHis | colE1 | cam | This study |
| $P_{lacUV5}$ hilA | | hilA | p15a | kan | [41] |

TABLE 15

Primers used in Example 4.

| Sequence | Amplicon | Used to Construct |
|---|---|---|
| AGGTCTCAGCTTgatatgttgaccccaactgaaag (SEQ ID NO: 78) | DH-GFP11 | sptP-DH-GFP11-2xFLAG-6xHis |
| AGGTCTCCCGCT*GGTGATGCCCGCCGC* *GTTCACGTATTCATGCAGCACCATATGAT* *CCCGCGAACCACCCCCAGATCCACCCC* agagttctccttctcccgc (SEQ ID NO: 79) | DH-GFP11 | sptP-DH-GFP11-2xFLAG-6xHis |
| AGGTCTCAGCTTcacccagaaacgctggtga (SEQ ID NO: 80) | bla-GFP11 | sptP-bla-GFP11-2xFLAG-6xHis |
| AGGTCTCCCGCT*GGTGATGCCCGCCGC* *GTTCACGTATTCATGCAGCACCATATGAT* *CCCGCGAACCACCCCCAGATCCACCCC* ccaatgcttaatcagtgagg (SEQ ID NO: 81) | bla-GFP11 | sptP-bla-GFP11-2xFLAG-6xHis |

DNA Manipulations

PCR was performed with Phusion DNA polymerase using the primers listed in Table 15. Golden gate cloning was used to construct plasmids [151]. Genes for proteins to be secreted were inserted into a modified pPROTet. 133 backbone vector (BD Clontech) under the control of the sic promoter [8]. All secretion plasmids expressed the SptP chaperone sicP and the sptP secretion signal (nucleotides 1 to 477). The SptP secretion tag was fused N-terminal to the protein of interest, and 2xFLAG and 6xHis tags were fused C-terminal to the protein of interest. The GFP11 tag was added C-terminal to the protein of interest using 3' extensions of the primers to append the tag 3' to the gene of interest. All cloning was done in E. coli DH10B cells, and all DNA sequences were confirmed by Sanger sequencing (Quintara).

Protein Separation and Western Blotting

Samples were separated by SDS-PAGE and stained with Coomassie R-250 according to Studier [153] or transferred to a polyvinylidene fluoride membrane (PVDF, Millipore) for western blotting using the Mini-Transblot cell (Bio-Rad). For western blotting, membranes were probed with mouse anti-FLAG per manufacturer's instructions (Sigma Aldrich). To facilitate chemiluminescent detection, a secondary labeling step was performed with goat anti-mouse IgG (H+L) HRP conjugate according to manufacturer's instructions (Thermo Fisher). Bands were detected with the SuperSignal West Pico or Pico Plus substrate (Thermo Fisher) and a ChemiDoc XRS+imaging system (Bio-Rad). All relative protein quantities were calculated by performing densitometry using Image Lab software (Bio-Rad) and normalizing to the specified normalization condition. Error bars are standard deviation on three biological replicates unless otherwise specified.

Protein Purification

All proteins were purified from S. enterica Typhimurium ASTE13 ΔprgI. Cells were grown and induced as described in "Strains and Growth Conditions" except that the growth vessel was a 250 mL Erlenmeyer flask containing 50 mL of terrific broth (TB). Cells were harvested by pelleting at 5000×g for 10 minutes. The supernatant was discarded, and the cell pellets were frozen at −80° C. Cell pellets were thawed and resuspended in 10 mL 20 mM sodium phosphate pH 7.4 with 500 mM NaCl and 20 mM imidazole. The resuspended cell solution was homogenized via sonication. The soluble and insoluble fractions were separated by centrifugation at 17,000×g for 20 minutes at 4° C. The soluble fraction was filtered with a 0.2 µm syringe filter before being applied to a His GraviTrap column (GE Life Sciences) for purification. The eluted protein was buffer-exchanged into phosphate-buffered saline using a PD-10 desalting column and quantified compared to a BSA standard using densitometry on an SDS-PAGE gel stained with Coomassie R-250 [153].

Example 5

This Examples describe development of secretion and assay conditions for the use of a genomic copy of SptP-AP-2xFLAG-6xHis for library screening, a recombineering method to create a genomically integrated CCM library from a mixture of gene blocks, and a method of scoring variants to construct a secretion fitness landscape according to the secretion titers measured in the library screen. A surprising 2% of screened library members increased secretion titer more than twofold. A majority of substitutions that increased secretion titer were larger and more hydrophobic amino acids, including many at residues that face the interior of the needle and potentially interact with the secreted protein.

Results

Figure 17:
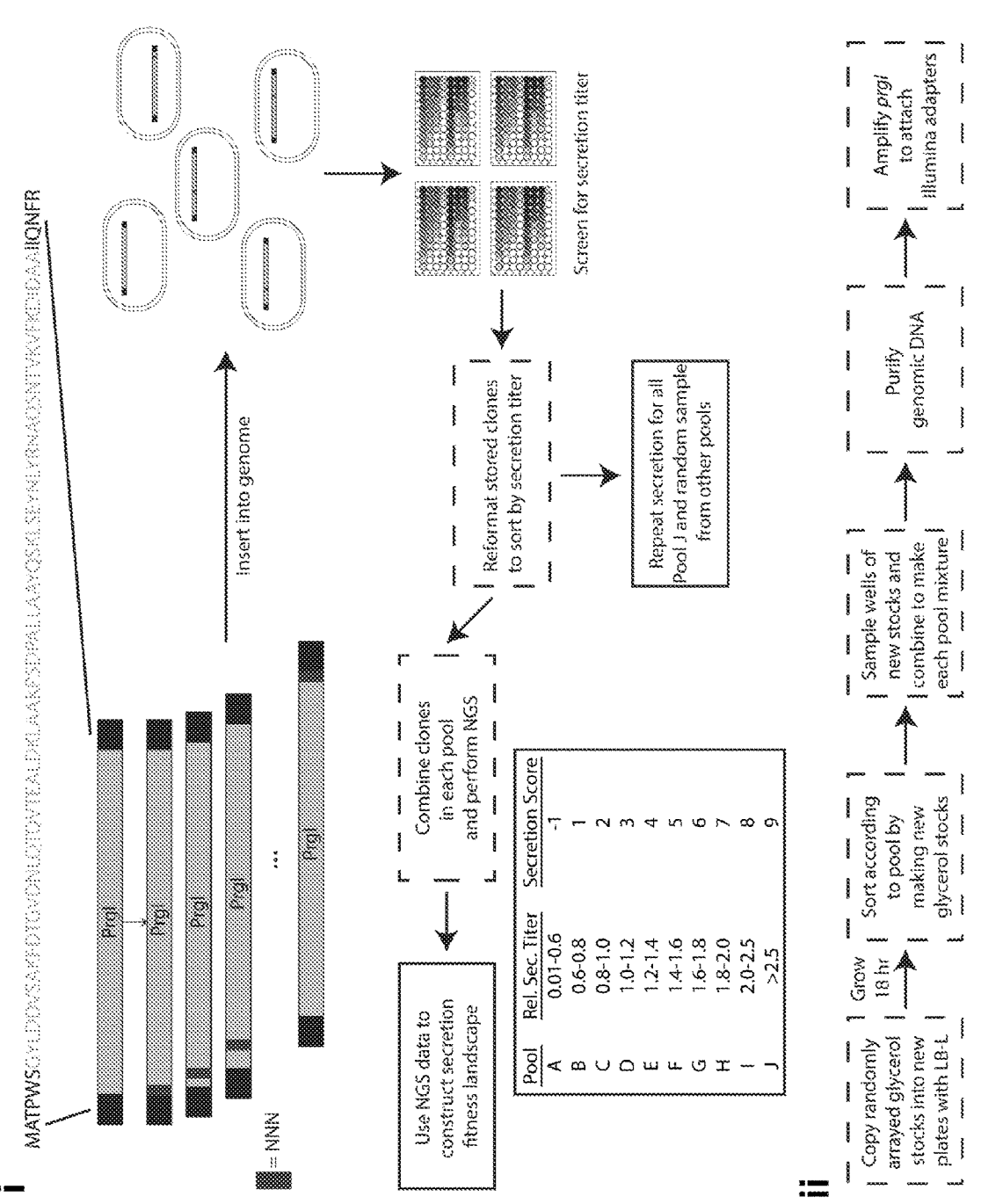
FIG. 17. Workflow for PrgI library assembly, screening, and analysis. Gene blocks coding for a single amino acid change in PrgI (e.g., SEQ ID NO:150) were introduced to ASTE13 sptP::sptP$^{(1-159)}$-phoA-2×FLAG-6×His prgI::cat-sacB as a mixture in a single recombineering event to create the library. Individual colonies were inoculated for secretion and screened for alkaline phosphatase activity as described in Methods. The randomly arrayed clones were sorted according to relative secretion titer, combined into their assigned pools, and prepared for sequencing on an Illumina MiSeq (ii). Data was analyzed as described to construct the secretion fitness landscape.

A "Secretion Fitness Landscape" Predicts Secretion Titer Resulting from a Single Amino Acid Change in PrgI The use of high-throughput sequencing to construct a fitness landscape from comprehensive codon mutagenesis was first developed in our lab to characterize single amino acid mutations that affected assembly of the MS2 viral capsid [187]. The procedure, SyMAPS, was developed for a bulk selection for assembly competence, so we adapted the workflow for the screened PrgI mutants to accommodate the individual clones and known secretion titers. The overall library construction, screening, and analysis workflow is depicted in FIG. 17.

In SyMAPS, the fitness landscape was assembled by comparing the relative abundance of a mutant after applying the selection pressure to its relative abundance in the naïve library [187]. In the PrgI library, "fitness" is relative secretion titer, so we wanted to characterize mutations according to those values. Thus, instead of one "selected pool", we assigned the PrgI library members to ten pools according to their relative secretion titer (FIG. 17). The PrgI library members were randomly arrayed in glycerol stocks, however, so in order to sequence each pool, we had to physically sort the clones. This took longer than expected because while we successfully used a Tecan Fluent to copy the randomly arrayed glycerol stocks and provide fresh cultures, it failed after reformatting pools F-J. The remaining pools were thus sorted by hand. The reformatting workflow is depicted in boxes with dashed borders in FIG. 17.

Figure 18:
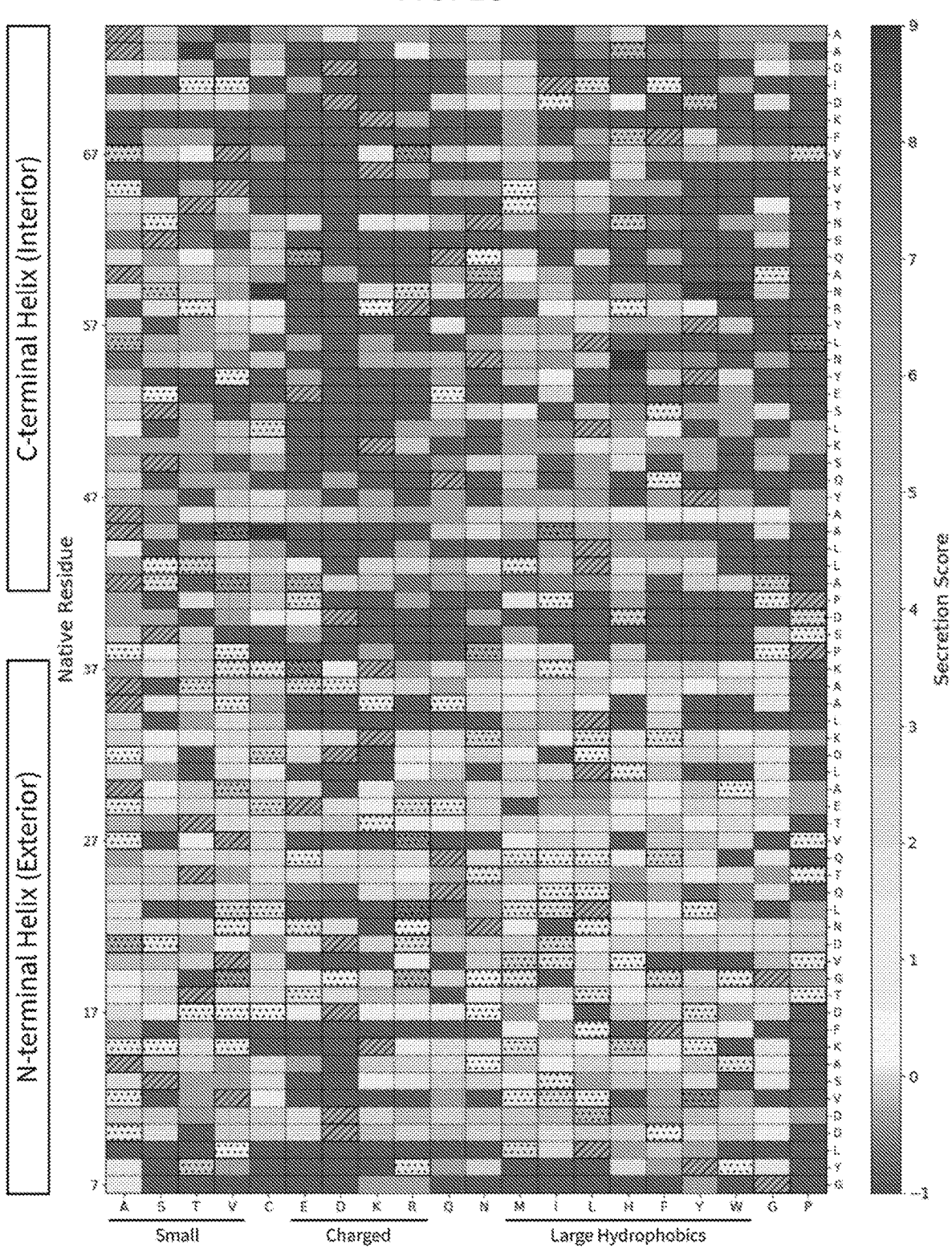
FIG. 18. Weighted-average secretion scores for all single amino acid variants of the modified residues of PrgI. Wild-type residues are indicated by hatches. Dots indicate that the variant appeared in pools B-J but also in pool A. Grey boxes denote variants that did not appear in pools A-J; i.e., those variants were not screened. Magenta boxes indicate that the variant was found only in pool A.

Of the 1292 possible variants, 89% were identified in pools A-J, and 100% were identified in the naïve library. To generate the fitness landscape, each pool was assigned a "secretion score" from −1 for dysfunctional secretion (pool A) to 9 for the highest-secreting clones (pool J). Variants appeared in multiple pools, so we calculated a weighted-average secretion score for each library member using its relative abundance in each pool as weights. The laborious nature of the library screening and reformatting process meant that only a single biological and technical replicate was used to construct the "Secretion Fitness Landscape" (SFL), so it is a semi-quantitative assessment (FIG. 18). The lack of replication made secretion competence uncertain for some amino acid changes—144 variants appeared in functional pools B-J but also in pool A, which contained secretion-incompetent variants. The weighted-average secretion score represents the relative abundance of the amino acid change in each pool, so pink-magenta variants are likely dysfunctional, while teal variants are likely functional.

The SFL revealed a distinct pattern—many substitutions were allowed in the N-terminal helix, but few conferred a significant increase in secretion titer. Conversely, few substitutions were allowed in the C-terminal helix, but the substitutions that were allowed generally conferred a significant increase in secretion titer.

A recent model of the PrgI needle depicted a right-handed groove with alternating charged and hydrophobic residues forming the edges and lumen of the groove, respectively [175]. The raised, charged groove is highly conserved across all species with a T3SS [175,191], so we were not surprised to discover that modifying those residues inhibited secretion (data not shown). We were surprised to discover that modifying the hydrophobic residues that line the groove and face the interior of the needle increased secretion titer, however. In fact, according to the SFL (FIG. 18), it was substitution of bulkier and more hydrophobic amino acids at those residues that conferred increased secretion titer.

The Secretion Fitness Landscape Predicted High-Secreting Variants

Figures 19A, 19B:
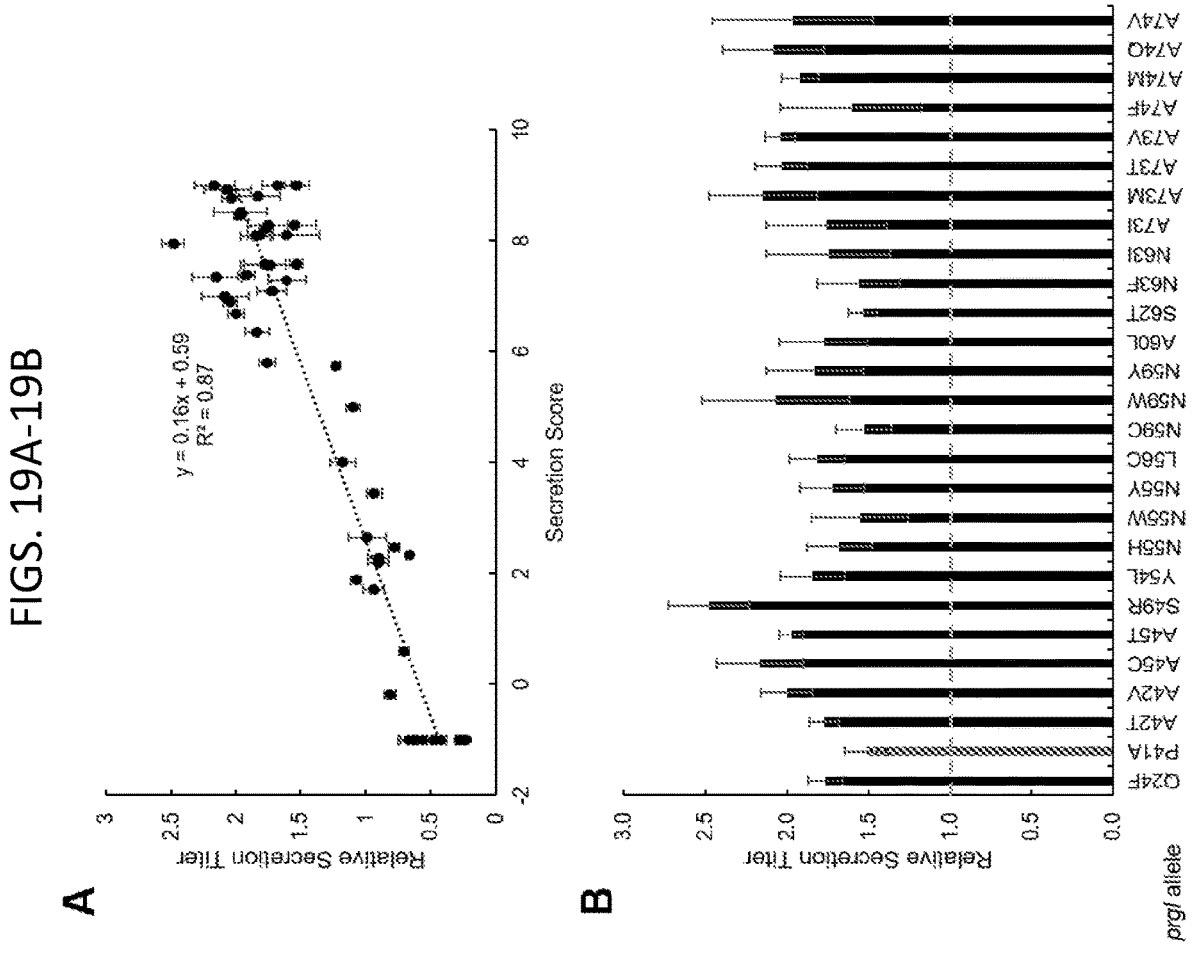
FIGS. 19A-19B. Weighted-average secretion scores predict relative secretion titer. Randomly selected clones from pools A-I and all clones from pool J were patched onto LB-agar plates from the reformatted glycerol stocks. Patched colonies were inoculated for secretion titer measurement, which followed the same workflow as library screening. Clones were Sanger sequenced, and the secretion score was plotted against the newly measured secretion titer (A). Error bars represent standard error of three biological replicates. Clones from pool J were plotted separately to highlight differences (B). WT-level secretion titer is indicated by a dotted line. PrgI$^{P41A}$ (stripes) was included for comparison as the previous best secreting variant. Error bars represent one standard deviation to allow direct comparison among variants.

We validated our SFL and library screening assay by repeating secretion titer measurement via alkaline phosphatase activity for a random assortment of variants from pools A-I and all variants from pool J. Relative secretion titer corresponded well ($R^2$=0.87) with the weighted-average secretion score (FIG. 19A). Though the re-analyzed pool J variants had generally lower relative secretion titers than the values from the library screen, all were at least 1.5-fold above PrgI$^{WT}$ (FIG. 19B).

The variants in pool J fell into the two classes observed for high average secretion scores—those that face the interior of the needle apparatus, and those that involve contact with neighboring residues. Multiple substitutions at residues 55, 59, 73, and 74 appeared in pool J, and most were larger and more hydrophobic than the native amino acid. The remaining variants likely changed interactions with neighboring residues, and those substitutions were of varying types. Most amino acid changes were to larger, more hydrophobic residues, but S49R and A74Q did not follow the pattern of hydrophobic substitutions.

Double Mutants Confer Increased Secretion Titer

Figure 20:
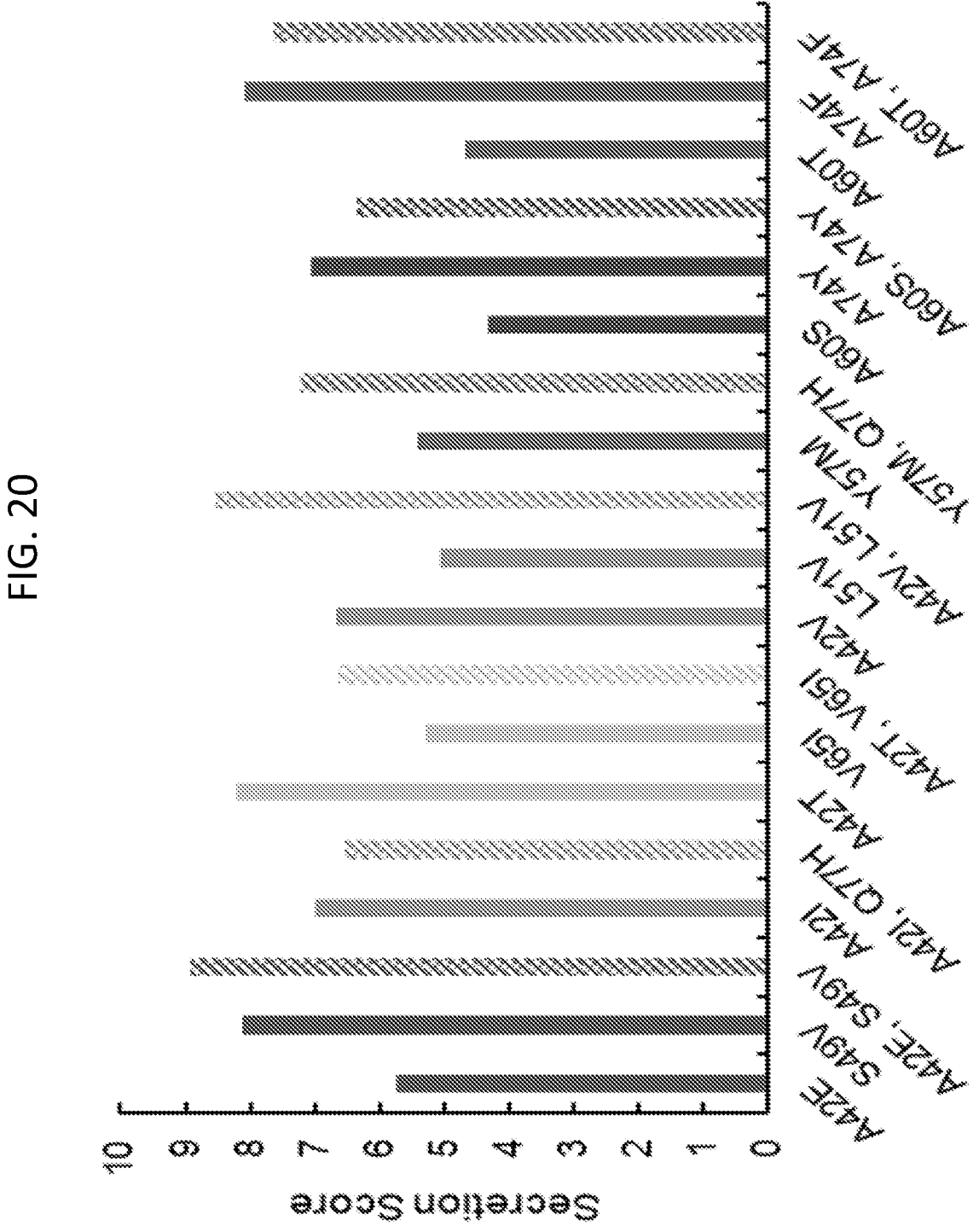
FIG. 20. Double mutants suggest epistatic effects. Secretion scores for double mutants were calculated from the correlation between relative secretion titer and secretion score in 19A and compared to secretion scores for each of the individual mutations.

The data processing workflow for the high throughput sequencing data deliberately discarded sequences with more than one amino acid change because multiple mutations were assumed to be sequencing or sample preparation errors. Sanger sequencing revealed that pool J contained several double mutants, however (FIG. 20). We hypothesize that the double mutants arose from assembling the library via recombineering, though it is possible they arose from errors in gene block synthesis. Experimental comparison of the secretion titers from the single and double mutants is necessary to confirm the patterns observed in FIG. 20, but the preliminary data suggests that an epistatic evaluation of mutant combinations would provide further insight into the design rules of the PrgI needle.

Materials and Methods

Strains and Growth Conditions for Secretion Experiments

Strains, plasmids, and primers used are listed in Table 16, Table 17 and Table 18. Secretion experiments were started by growing a single colony in the lysogeny broth Lennox formulation (10 g/L tryptone, 5 g/L yeast extract, 5 g/L NaCl) with appropriate antibiotics (34 μg/mL chloramphenicol for P$_{sic}$ vectors, 50 μg/mL kanamycin for P$_{lacUV5}$ hilA) for 12-16 hours overnight in an orbital shaker at 37° C. and 225 rpm unless otherwise specified. Overnight cultures were diluted 1:100 into the appropriate medium supplemented with appropriate antibiotics and 100 μg/mL isopropyl β-D-1-thiogalactopyranoside (IPTG) if the strain carried P$_{lacUV5}$ hilA. All culturing steps were performed in 24-well deep-well plates (Axygen) unless otherwise specified. Secretion was performed at 37° C. and 225 rpm in an orbital shaker for eight hours. The secreted fraction was harvested by centrifuging cultures at 4000×g for 10 minutes. SDS-PAGE samples for the secretion fraction were prepared by adding supernatant to Laemmli buffer in a 3:1 ratio; SDS-PAGE samples for whole culture lysate were prepared by adding cell suspension to Laemmli buffer in a 1:2 ratio. All SDS-PAGE samples were boiled at 95° C. for 5 minutes immediately after preparation.

TABLE 16

| Strains used in Example 5 | | |
| --- | --- | --- |
| Strain | Genotype | Reference |
| ASTE13 | LT2-derived lab strain similar to DW01 | This study; DW01 [65] |
| ASTE13 ΔprgI | ΔprgI | [41] |
| ASTE13 prgI::catsacB | prgI::catsacB | [181] |
| DTE509 | ASTE13 prgI::prgI$^{L9A}$ | [181] |
| DTE510 | ASTE13 prgI::prgI$^{Q48A}$ | [181] |
| DTE511 | ASTE13 prgI::prgI$^{Y54A}$ | [181] |
| DTE512 | ASTE13 prgI::prgI$^{D70A}$ | [181] |
| DTE513 | ASTE13 prgI::prgI$^{P41A}$ | [181] |
| DTE514 | ASTE13 prgI::prgI$^{P41C}$ | This study |
| DTE515 | ASTE13 prgI::prgI$^{P41D}$ | This study |
| DTE516 | ASTE13 prgI::prgI$^{P41E}$ | This study |
| DTE517 | ASTE13 prgI::prgI$^{P41F}$ | This study |
| DTE518 | ASTE13 prgI::prgI$^{P41G}$ | This study |
| DTE519 | ASTE13 prgI::prgI$^{P41H}$ | This study |
| DTE520 | ASTE13 prgI::prgI$^{P41I}$ | This study |
| DTE521 | ASTE13 prgI::prgI$^{P41K}$ | This study |
| DTE522 | ASTE13 prgI::prgI$^{P41L}$ | This study |
| DTE523 | ASTE13 prgI::prgI$^{P41M}$ | This study |
| DTE524 | ASTE13 prgI::prgI$^{P41N}$ | This study |
| DTE525 | ASTE13 prgI::prgI$^{P41O}$ | This study |
| DTE526 | ASTE13 prgI::prgI$^{P41R}$ | This study |
| DTE527 | ASTE13 prgI::prgI$^{P41S}$ | This study |
| DTE528 | ASTE13 prgI::prgI$^{P41T}$ | This study |
| DTE529 | ASTE13 prgI::prgI$^{P41V}$ | This study |
| DTE530 | ASTE13 prgI::prgI$^{P41W}$ | This study |
| DTE531 | ASTE13 prgI::prgI$^{P41Y}$ | This study |
| sLAB190 | ASTE13 sptP::sptP$^{(1-159)}$-phoA-2xFLAG-6xHis | This study |
| sLAB191 | ASTE13 sptP::sptP$^{(1-159)}$-phoA-2xFLAG-6xHis prgI::catsacB | This study |
| sLAB192 | ASTE13 sptP::sptp$^{(1-159)}$-phoA-2xFLAG-6xHis prgI::prgI$^{P41A}$ | This study |
| sLAB193 | ASTE13 sptP::sptp$^{(1-159)}$-phoA-2xFLAG-6xHis prgI::prgI$^{P41C}$ | This study |
| sLAB194 | ASTE13 sptP::sptP$^{(1-159)}$-phoA-2xFLAG-6xHis prgI::prgI$^{P41M}$ | This study |
| sLAB195 | ASTE13 sptP::sptp$^{(1-159)}$-phoA-2xFLAG-6xHis prgI::prgI$^{P41T}$ | This study |
| sLAB196 | ASTE13 sptP::sptp$^{(1-159)}$-phoA-2xFLAG-6xHis prgI::prgI$^{P41V}$ | This study |
| sLAB203 | ASTE13 sptP::sptP$^{(1-159)}$-phoA-2xFLAG-6xHis prgI::prgI$^{P41D}$ | This study |
| sLAB204 | ASTE13 sptP::sptP$^{(1-159)}$-phoA-2xFLAG-6xHis prgI::prgI$^{P41E}$ | This study |
| sLAB205 | ASTE13 sptP::sptP$^{(1-159)}$-phoA-2xFLAG-6xHis prgI::prgI$^{P41F}$ | This study |
| sLAB206 | ASTE13 sptP::sptP$^{(1-159)}$-phoA-2xFLAG-6xHis prgI::prgI$^{P41G}$ | This study |
| sLAB207 | ASTE13 sptP::sptP$^{(1-159)}$-phoA-2xFLAG-6xHis prgI::prgI$^{P41H}$ | This study |
| sLAB208 | ASTE13 sptP::sptP$^{(1-159)}$-phoA-2xFLAG-6xHis prgI::prgI$^{P41I}$ | This study |
| sLAB209 | ASTE13 sptP::sptP$^{(1-159)}$-phoA-2xFLAG-6xHis prgI::prgI$^{P41K}$ | This study |
| sLAB210 | ASTE13 sptP::sptP$^{(1-159)}$-phoA-2xFLAG-6xHis prgI::prgI$^{P41L}$ | This study |
| sLAB211 | ASTE13 sptP::sptP$^{(1-159)}$-phoA-2xFLAG-6xHis prgI::prgI$^{P41N}$ | This study |
| sLAB212 | ASTE13 sptP::sptP$^{(1-159)}$-phoA-2xFLAG-6xHis prgI::prgI$^{P41Q}$ | This study |
| sLAB213 | ASTE13 sptP::sptP$^{(1-159)}$-phoA-2xFLAG-6xHis prgI::prgI$^{P41R}$ | This study |
| sLAB214 | ASTE13 sptP::sptP$^{(1-159)}$-phoA-2xFLAG-6xHis prgI::prgI$^{P41S}$ | This study |
| sLAB215 | ASTE13 sptP::sptP$^{(1-159)}$-phoA-2xFLAG-6xHis prgI::prgI$^{P41W}$ | This study |
| sLAB216 | ASTE13 sptP::sptP$^{(1-159)}$-phoA-2xFLAG-6xHis prgI::prgI$^{P41Y}$ | This study |
| sLAB305 | ASTE13 sptP::sptP$^{(1-159)}$-phoA-2xFLAG-6xHis ΔinvA | This study |

TABLE 17

Plasmids used in Example 5.

| Plasmid Name | | ORFs under inducible control | ORI | ab$^R$ | Reference |
|---|---|---|---|---|---|
| P$_{sic}$ DH | sicP | sptP-DH-2xFLAG-6xHis | colE1 | cam | [41] |
| P$_{sic}$ AP | sicP | sptP-phoA-2xFLAG-6xHis | colE1 | cam | [38] |
| P$_{lacUV5}$ hilA | | hilA | p15a | kan | [41] |
| pSIM6 | | gam, beta, exo | pSC101 | cb | [152] |
| P$_{lacUV5}$ P41A | | prgI$^{P41A}$ | colE1 | kan | [181] |
| P$_{lacUV5}$ P41C | | prgI$^{P41C}$ | colE1 | kan | This study |
| P$_{lacUV5}$ P41D | | prgI$^{P41D}$ | colE1 | kan | This study |
| P$_{lacUV5}$ P41E | | prgI$^{P41E}$ | colE1 | kan | This study |
| P$_{lacUV5}$ P41F | | prgI$^{P41F}$ | colE1 | kan | This study |
| P$_{lacUV5}$ P41G | | prgI$^{P41G}$ | colE1 | kan | This study |
| P$_{lacUV5}$ P41H | | prgI$^{P41H}$ | colE1 | kan | This study |
| P$_{lacUV5}$ P41I | | prgI$^{P41I}$ | colE1 | kan | This study |
| P$_{lacUV5}$ P41K | | prgI$^{P41K}$ | colE1 | kan | This study |
| P$_{lacUV5}$ P41L | | prgI$^{P41L}$ | colE1 | kan | This study |
| P$_{lacUV5}$ P41M | | prgI$^{P41M}$ | colE1 | kan | This study |
| P$_{lacUV5}$ P4lN | | prgI$^{P41N}$ | colE1 | kan | This study |
| P$_{lacUV5}$ P41Q | | prgI$^{P41Q}$ | colE1 | kan | This study |
| P$_{lacUV5}$ P41R | | prgI$^{P41R}$ | colE1 | kan | This study |
| P$_{lacUV5}$ P41S | | prgI$^{P41S}$ | colE1 | kan | This study |
| P$_{lacUV5}$ P41T | | prgI$^{P41T}$ | colE1 | kan | This study |
| P$_{lacUV5}$ P41V | | prgI$^{P41V}$ | colE1 | kan | This study |
| P$_{lacUV5}$ P41W | | prgI$^{P41W}$ | colE1 | kan | This study |
| P$_{lacUV5}$ P41Y | | prgI$^{P41Y}$ | colE1 | kan | This study |

PCR and Cloning

Primers used in this study are listed in Table 18. PCR was performed with Phusion DNA polymerase for Quikchanges and constructing parts for recombineering. Saturation mutagenesis at position 41 was performed by introducing mutations to prgI carried on a P$_{lacUV5}$-inducible plasmid with a Quikchange protocol. Mutations were confirmed by Sanger sequencing. Double-stranded DNA fragments for recombineering contained the replacement gene(s) flanked 5' and 3' by 40 bp of homology to the genetic locus at which the replacement gene(s) should be inserted. The 40 bp of homology was included in oligos and attached via PCR using the primers listed in Table 18. The cat-sacB cassette was amplified from the purified genome of E. coli TUC01, PrgI position 41 mutants were amplified from the appropriate P$_{lacUV5}$-inducible plasmid, and sptP-phoA-2xFLAG-6x His was amplified from a P$_{sic}$ sicP sptP-phoA-2xFLAG-6x His secretion plasmid. Colony PCR was performed by diluting a colony in a 50 µL PCR reaction containing the appropriate primers and amplifying with GoTaq polymerase. Correct sequences were confirmed by Sanger sequencing.

TABLE 18

Primers used in Example 5.

| Sequence | Amplicon | Used to Construct |
|---|---|---|
| GCAGCAAAACCCTCCGATTGTGC GCTACTGGCGGCGTATC (SEQ ID NO: 155) | prgI$^{P41C}$ QC | P$_{lacUV5}$ P41C |
| GATACGCCGCCAGTAGCGCACAA TCGGAGGGTTTTGCTGC(SEQ ID NO: 156) | prgI$^{P41C}$ QC | P$_{lacUV5}$ P41C |
| GCAGCAAAACCCTCCGATGATCG CTACTGGCGGCGTATC (SEQ ID NO: 157) | prgI$^{P41D}$ QC | P$_{lacUV5}$ P41D |
| GATACGCCGCCAGTAGCGCATCA TCGGAGGGTTTTGCTGC (SEQ ID NO: 158) | prgI$^{P41D}$ QC | P$_{lacUV5}$ P41D |
| GCAGCAAAACCCTCCGATGAAGC GCTACTGGCGGCGTATC ((SEQ ID NO: 159) | prgI$^{P41E}$ QC | P$_{lacUV5}$ P41E |
| GATACGCCGCCAGTAGCGCTTCA TCGGAGGGTTTTGCTGC ((SEQ ID NO: 160) | prgI$^{P41E}$ QC | P$_{lacUV5}$ P41E |
| CAAAACCCTCCGATTTTGCGCTA CTGGCGGCG ((SEQ ID NO: 161) | prgI$^{P4lF}$ QC | P$_{lacUV5}$ P41F |
| CGCCGCCAGTAGCGCAAAATCGG AGGGTTTTG ((SEQ ID NO: 162) | prgI$^{P4lF}$ QC | P$_{lacUV5}$ P41F |

TABLE 18-continued

Primers used in Example 5.

| Sequence | Amplicon | Used to Construct |
|---|---|---|
| CAAAACCCTCCGATGGAGCGCTA CTGGCGGC (SEQ ID NO: 163) | $prgI^{P41G}$ QC | $P_{lacUV5}$ P41G |
| GCCGCCAGTAGCGCTCCATCGGA GGGTTTTG (SEQ ID NO: 164) | $prgI^{P41G}$ QC | $P_{lacUV5}$ P41G |
| CAGCAAAACCCTCCGATCATGCG CTACTGGCGGCGTATC ((SEQ ID NO: 165) | $prgI^{P41H}$ QC | $P_{lacUV5}$ P41H |
| GATACGCCGCCAGTAGCGCATGA TCGGAGGGTTTTGCTG ((SEQ ID NO: 166) | $prgI^{P41H}$ QC | $P_{lacUV5}$ P41H |
| CAAAACCCTCCGATATAGCGCTA CTGGCGGCG (SEQ ID NO: 167) | $prgI^{P411}$ QC | $P_{lacUV5}$ P41I |
| CGCCGCCAGTAGCGCTATATCGG AGGGTTTTG (SEQ ID NO: 168) | $prgI^{P41I}$ QC | $P_{lacuV5}$ P41I |
| CAAAACCCTCCGATAAGGCGCTA CTGGCG (SEQ ID NO: 169) | $prgI^{P41K}$ QC | $P_{lacuV5}$ P41K |
| CGCCAGTAGCGCCTTATCGGAGG GTTTTG (SEQ ID NO: 170) | $prgI^{P41K}$ QC | $P_{lacUV5}$ P41K |
| CAAAACCCTCCGATTTGGCGCTA CTGGCG (SEQ ID NO: 171) | $prgI^{P4lL}$ QC | $P_{lacUV5}$ P41L |
| CGCCAGTAGCGCCAAATCGGAG GGTTTTG (SEQ ID NO: 172) | $prgI^{P4lL}$ QC | $P_{lacUV5}$ P41L |
| CAAAACCCTCCGATATGGCGCTA CTGGCGGCG (SEQ ID NO: 173) | $prgI^{P41M}$ QC | $P_{lacuV5}$ P41M |
| CGCCGCCAGTAGCGCCATATCGG AGGGTTTTG (SEQ ID NO: 174) | $prgI^{P41M}$ QC | $P_{lacUV5}$ P41M |
| CAAAACCCTCCGATAATGCGCTA CTGGCGGCG (SEQ ID NO: 175) | $prgI^{P4lN}$ QC | $P_{lacUV5}$ P41N |
| CGCCGCCAGTAGCGCATTATCGG AGGGTTTTG (SEQ ID NO: 176) | $prgI^{P4lN}$ QC | $P_{lacUV5}$ P41N |
| CAGCAAAACCCTCCGATCAAGCG CTACTGGCGGCGTATC (SEQ ID NO: 177) | $prgI^{P41Q}$ QC | $P_{lacUV5}$ P41Q |
| GATACGCCGCCAGTAGCGCTTGA TCGGAGGGTTTTGCTG (SEQ ID NO: 178) | $prgI^{P41Q}$ QC | $P_{lacUV5}$ P41Q |
| GCAGCAAAACCCTCCGATAGAGC GCTACTGGCGGCGTATC (SEQ ID NO: 179) | $prgI^{P4lR}$ QC | $P_{lacUV5}$ P41R |
| GATACGCCGCCAGTAGCGCTCTA TCGGAGGGTTTTGCTGC (SEQ ID NO: 180) | $prgI^{P41R}$ QC | $P_{lacUV5}$ P41R |
| GCAGCAAAACCCTCCGATAGTGC GCTACTGGCGGCGTATC (SEQ ID NO: 181) | $prgI^{P415}$ QC | $P_{lacUV5}$ P41S |
| GATACGCCGCCAGTAGCGCACTA TCGGAGGGTTTTGCTGC (SEQ ID NO: 182) | $prgI^{P415}$ QC | $P_{lacUV5}$ P41S |
| GCAGCAAAACCCTCCGATACAGC GCTACTGGCGGCGTATC (SEQ ID NO: 183) | $prgI^{P4lT}$ QC | $P_{lacUV5}$ P41T |
| GATACGCCGCCAGTAGCGCTGTA TCGGAGGGTTTTGCTGC (SEQ ID NO: 184) | $prgI^{P4lT}$ QC | $P_{lacUV5}$ P4IT |

TABLE 18-continued

| Sequence | Amplicon | Used to Construct |
|---|---|---|
| GCAGCAAAACCCTCCGATGTAGC GCTACTGGCGGCGTATC (SEQ ID NO: 185) | prgI$^{P41V}$ QC | P$_{lacUV5}$ P41V |
| GATACGCCGCCAGTAGCGCTACA TCGGAGGGTTTTGCTGC (SEQ ID NO: 186) | prgI$^{P41V}$ QC | P$_{lacUV5}$ P41V |
| CAAAACCCTCCGATTGGGCGCTA CTGGCGGCG (SEQ ID NO: 187) | prgI$^{P41W}$ QC | P$_{lacUV5}$ P41W |
| CGCCGCCAGTAGCGCCCAATCGG AGGGTTTTG (SEQ ID NO: 188) | prgI$^{P41W}$ QC | P$_{lacUV5}$ P41W |
| CAAAACCCTCCGATTATGCGCTA CTGGCGGCG (SEQ ID NO: 189) | prgI$^{P41Y}$ QC | P$_{lacUV5}$ P41Y |
| CGCCGCCAGTAGCGCATAATCGG AGGGTTTTG (SEQ ID NO: 190) | prgI$^{P41Y}$ QC | P$_{lacUV5}$ P41Y |
| AACATACTGCAGGAATATGCTAA AGTATGAGGAGAGAAAA tgtgacggaagatcacttcg (SEQ ID NO: 191) | cat-sacB | ASTE13 sptP::catsacB |
| GCTTACTTTCAGATAGTTCTAAA AGTAAGCTATGTTTTTA atcaaagggaaaactgtccatat ((SEQ ID NO: 192) | cat-sacB | ASTE13 sptP::catsacB |
| CTTGAGTCATTTGTGAATCAGCA GGAAGCGCTCAAAAACATACTGC AGGAATATGCTAAAGTATGAGG AGAGAAAA ttgaataatttaacgttgtcttcg (SEQ ID NO: 193) | sptp$^{(1-159)}$-phoA-2xFLAG-6xHis | ASTE13 sptP::sptp$^{(1-159)}$-phoA-2xFLAG-6xHis |
| ACTTTCTATCGCGGCAAACAAAT AATTATACAGAAATAGCTTACTT TCAGATAGTTCTAAAAGTAAGCT ATGTTTTTA ttagtggtgatggtgatgatgc (SEQ ID NO: 194) | sptp$^{(1-159)}$-phoA-2xFLAG-6xHis | ASTE13 sptP::sptp$^{(1-159)}$-phoA-2xFLAG-6xHis |
| CCCAAGCCCACTTTAATTTAACG TAAATAAGGAAGTCATT atggcaacaccttggtcagg (SEQ ID NO: 195) | prgI | All ASTE13 prgI variants |
| GGACAATAGTTGCAATCGACATA ATCCACCTTATAACTGA ttaacggaagttctgaataatggc (SEQ ID NO: 196) | prgI | All ASTE13 prgI variants |
| CTATAGTGCTGCTTTCTCTACTTA ACAGTGCTCGTTTACG tgtgacggaagatcacttcg (SEQ ID NO: 197) | cat-sacB | ASTE13 sptP::sptp$^{(1-159)}$-phoA-2xFLAG-6xHis ΔinvA |
| GCCCTTATATTGTTTTTATAACAT TCACTGACTTGCTAT atcaaagggaaaactgtccat (SEQ ID NO: 198) | cat-sacB | ASTE13 sptP::sptp$^{(1-159)}$-phoA-2xFLAG-6xHis ΔinvA |
| TTATATTGTTTTTATAACATTCAC TGACTTGCTATCGTAAACGAGCA CTGTTAAGTAGAGAAAGCAGCAC (SEQ ID NO: 199) | N/A | ASTE13 sptP::sptp$^{(1-159)}$-phoA-2xFLAG-6xHis ΔinvA |
| TCGTCGGCAGCGTCAGATGTGTA TAAGAGACAG atggcaacaccttggtcag (SEQ ID NO: 200) | prgI | PrgI library for NGS - PCR step 1 |

TABLE 18-continued

Primers used in Example 5.

| Sequence | Amplicon | Used to Construct |
|---|---|---|
| GTCTCGTGGGCTCGGAGATGTGT ATAAGAGACAG ttaacggaagttctgaataatggc (SEQ ID NO: 201) | prgI | PrgI library for NGS - PCR step 1 |

Strain Construction for Single Genomic Modifications

Strain modifications were generated by λ Red recombineering as described by Thomason et al. [152]. Briefly, a colony of ASTE13 carrying the pSIM6 plasmid was inoculated in LB-L with 30 µg/mL carbenicillin and grown at 30° C. and 225 rpm for 16-20 hours. The overnight culture was diluted 1:70 into 35 mL of LB-L and grown at 30° C. until $OD_{600}$ reach 0.4-0.6. The culture was washed twice with 30 mL ice-cold sterile $ddH_2O$ and centrifugation at 4600×g for 3 minutes to collect the cells. After the second wash, cells were resuspended in ~400 µL of ice-cold sterile $ddH_2O$. Aliquots of 50 µL resuspended cells were mixed with 200 ng of the appropriate PCR fragment and electroporated at 1800V for 5 milliseconds. A negative control containing no added DNA was also electroporated. Cells were mixed with 950 µL SOC medium immediately after electroporation and either recovered at 30° C. for an hour for cat-sacB cassette introduction (first step of recombineering) or transferred to a test tube containing 9 mL of LB-L and grown at 37° C., 225 rpm for four hours for cat-sacB removal and replacement (second step of recombineering). Cells were diluted serially to $10^{-3}$ in sterile PBS. 200 µL of diluted cells was plated on 6% sucrose agar and grown at 37° C. overnight. The second step of recombineering for the ΔinvA knockout replaced the cat-sacB cassette by electroporating 1 µL of a 10 µM solution of a single 60 bp oligo containing the first and last 30 bp of the invA gene.

Library Construction

A library of gene blocks carrying all possible amino acid substitutions was synthesized and pooled by Twist Biosciences. Codons were fully randomized ("NNN"), but the library excluded wild-type residues and stop codons. Residues 1-6 and 76-80 were not modified. The lyophilized DNA from Twist Biosciences was reconstituted in ultrafiltered water to a concentration of 200 ng/µL. Recombineering was performed with an ASTE13 sptP::sptP$^{(1-159)}$-phoA-2× FLAG-6×His prgI::cat-sacB as described above with the following modifications. 200 ng (4 µL of a 50 ng/µL resuspended solution) of the library was transformed into 100 µL of recombination-competent cells via electroporation at 1800V and 5 milliseconds. A negative control containing no added DNA was also electroporated. Cells were immediately mixed with 900 µL SOC medium and transferred to a 14 mL disposable culture tube (Fisherbrand) containing 2 mL of LB-L for a four-hour recovery at 37° C. and 225 rpm. Recombination efficiency was assessed by plating 200 µL of cells diluted serially to $10^{-3}$ in sterile PBS from both the library and the negative control on 6% sucrose agar and allowing colonies to develop at room temperature for 24 hours. The remainder of the culture was mixed with 60% glycerol in a 1:3 ratio and aliquoted into three cryovials for storage at −80° C. Before storage, 2×33 µL aliquots of the glycerol mixture were diluted to facilitate plating single colonies for screening. The first aliquot was diluted in 1.2 mL sterile PBS, and the second aliquot was diluted in 1.2 mL PBS with 15% glycerol and frozen at −80° C. The 1.2 mL aliquot without glycerol was further split into 3×400 µL aliquots, and each was plated on a 15 cm agar plate with 6% sucrose LB-agar. Colonies developed for 24 hours at room temperature.

Library Screening

Single colonies were inoculated in 0.5 mL LB-L in a 2 mL square 96-well deepwell plate (Axygen) and grown overnight at 37° C., 350 rpm. ASTE13 sptP::sptP$^{(1-159)}$-phoA-2×FLAG-6×His, ASTE13 sptP::sptP$^{(1-159)}$-phoA-2×FLAG-6×His prgI::catsacB, and ASTE13 sptP::sptP$^{(1-159)}$-phoA-2×FLAG-6×His ΔinvA were included in each deepwell plate as controls. Overnight cultures were stored for analysis and high-throughput sequencing by diluting 180 µL of overnight culture with 60 µL 60% glycerol in a sterile, round-bottom 96-well plate (Corning), sealing the plate, and storing it at −80° C. To facilitate secretion, overnight cultures were diluted 1:100 into 0.5 mL TB in a fresh 2 mL square 96-well deepwell plate and grown for 8 hours at 37° C., 350 rpm. The secretion fraction was harvested by pelleting cells in the deepwell plates at 4000×g for 10 minutes, collecting 200 µL of the supernatant, and storing it in a sealed plate at 4° C.

Sample Preparation for High Throughput Sequencing

The randomly arrayed glycerol stocks were inoculated in identical arrangements in fresh media in sterile, flat-bottom 96-well plates using a Tecan Fluent and grown with lids in DigiLab HiGro shaking stacks at 37° C., 200 rpm for 18 hours. Each clone was assigned a pool according to its relative secretion titer (Table 19). A Tecan Fluent was used to reformat clones and sort them into their assigned pools. A VBA macro assigned pools according to relative secretion titer and assigned clones to a new plate and well ID to provide instructions for the Tecan Fluent. 150 µL of the fresh cell suspension was mixed with 50 µL 60% glycerol in a fresh sterile, round-bottom 96-well plate (Corning). The Tecan Fluent failed after sorting pools F-J, so the remainder were done by hand over the course of a week. Each well of the newly sorted glycerol stocks was sampled and pooled according to Table 19 for genomic DNA purification. Genomic DNA was purified from 1 mL of each pool and 0.5 mL of the naïve library using the GenElute Bacterial Genomic DNA kit (Sigma).

TABLE 19

Pools for high throughput sequencing according to relative secretion titer.

| Pool | Relative Secretion Titer | Number of Clones | Sample Volume for Mixture (µL) | Nextera XT Primer i5 | Nextera XT Primer i7 |
|---|---|---|---|---|---|
| A | 0.01-0.6 | 2015 | 5 | N707 | S502 |
| B | 0.6-0.8 | 575 | 10 | N710 | S502 |
| C | 0.8-1.0 | 691 | 10 | N711 | S502 |
| D | 1.0-1.2 | 480 | 20 | N712 | S502 |

TABLE 19-continued

Pools for high throughput sequencing according to relative secretion titer.

| Pool | Relative Secretion Titer | Number of Clones | Sample Volume for Mixture (µL) | Nextera XT Primer i5 | Nextera XT Primer i7 |
|---|---|---|---|---|---|
| E | 1.2-1.4 | 236 | 20 | N714 | S502 |
| F | 1.4-1.6 | 151 | 20 | N705 | S503 |
| G | 1.6-1.8 | 77 | 30 | N706 | S503 |
| H | 1.8-2.0 | 75 | 30 | N707 | S503 |
| I | 2.0-2.5 | 70 | 30 | N710 | S503 |
| J | >2.5 | 36 | 50 | N711 | S503 |

PCR for library preparation was conducted with Phusion polymerase. The purified genomes from the pool mixtures were amplified using the "Round 1" reaction recipe (Table 20) and cycling conditions (Table 21) with primers sLAB278 and sLAB279 (Table 18) to attach Illumina Nextera XT adapters. Reactions were purified using the Promega Wizard SV PCR cleanup kit. For each pool, 8×25 µL reactions were performed and pooled after PCR cleanup to minimize jackpot effects. A second round of PCR attached Nextera XT barcodes according to Table 19 using the "Round 2" reaction recipe and cycling conditions in Table 20 and Table 21 with the pooled Round 1 reactions as templates.

TABLE 20

PCR reactions for high throughput sequencing library preparation

| Component | Round 1 (25 µL × 8 per pool) | Round 2 (50 µL × 1 per pool) |
|---|---|---|
| 5× HF Buffer (NEB) | 5 µL | 10 µL |
| 10 mM dNTPs (NEB) | 0.5 µL | 1 µL |
| 10 µM FWD primer | 1.25 µL | 2.5 µL |
| 10 µM REV primer | 1.25 µL | 2.5 µL |
| Template DNA | 2.5 µL of 5 ng/µL gDNA | 5 µL purified and combined Round 1 reaction |
| Phusion (NEB) | 0.25 µL | 0.5 µL |
| $H^2O$ | 14.25 µL | 28.5 µL |

TABLE 21

PCR cycling conditions for high throughput sequencing library preparation

| Step | Round 1 (25 µL × 8 per pool) T (° C.) | Round 1 (25 µL × 8 per pool) Time (sec) | Round 2 (50 µL × 1 per pool) T (° C.) | Round 2 (50 µL × 1 per pool) Time (sec) |
|---|---|---|---|---|
| Initial Denaturation | 98 | 60 | 98 | 30 |
| Amplification | 98 | 10 | 98 | 10 |
| (Round 1-22 cycles) | 62 | 15 | 61 | 15 |
| (Round 2-8 cycles) | 72 | 30 | 72 | 30 |
| Elongation | 72 | 300 | 72 | 300 |
| Hold | 4 | indefinite | 4 | indefinite |

High-Throughput Sequencing Data Processing

The code for data processing using the Linux command-line interface (bash) is given following each explanation. Data were trimmed using Trimmomatic64 with a 2-unit sliding quality window of 30 and a minimum length of 30. Sequences were cropped to 243 bp.

```
java -jar trimmomatic-0.36.jar SE
input_forward_HTS001.fastq.gz HTS001_trimmed SLID-
INGWINDOW: 2:30 MINLEN: 30 CROP: 243
```

Reads were then aligned to the wild-type PrgI reference gene with Burrows-Wheeler Aligner (BWA-MEM) 66 and piped into Samtools to convert to a bam file.

```
bwa mem -p Reference/ref.fasta
HTS001_trimmed.fastq|samtools view -bT Reference/ref-
.fasta -o HTS001.bam
```

Reads that fully mapped to PrgI were kept for further analysis.

```
samtools view HTS001.bam|grep "243M"|sort|less-
S>HTS001.txt
```

The trimmed reads were further processed to generate a secretion fitness landscape using code written in-house.

REFERENCES FOR EXAMPLES 2-5

8. Widmaier D M, Tullman-Ercek D, Mirsky E A, Hill R, Govindarajan S, Minshull J, et al. Engineering the *Salmonella* type III secretion system to export spider silk monomers. Molecular Systems Biology. 2009; 5:309.

21. Anné J, Maldonado B, Van Impe J, Van Mellaert L, Bernaerts K. Recombinant protein production and streptomycetes. Journal of Biotechnology. 2012; 158:159-67.

22. Anné J, Vrancken K, Van Mellaert L, Van Impe J, Bernaerts K. Protein secretion biotechnology in Gram-positive bacteria with special emphasis on *Streptomyces lividans*. Biochim Biophys Acta. 2014; 1843:1750-61.

38. Metcalf K J, Bevington J L, Rosales S L, Burdette L A, Valdivia E, Tullman-Ercek D. Proteins adopt functionally active conformations after type III secretion. Microbial Cell Factories. 2016; 15:213.

41. Metcalf K J, Finnerty C, Azam A, Valdivia E, Tullman-Ercek D. Using Transcriptional Control To Increase Titers of Secreted Heterologous Proteins by the Type III Secretion System. Applied and Environmental Microbiology. 2014; 80:5927-34.

52. Glasgow A A, Wong H T, Tullman-Ercek D. A Secretion-Amplification Role for *Salmonella enterica* Translocon Protein SipD. ACS Synth Biol. 2017; 6:1006-15.

65. Song M, Sukovich D J, Ciccarelli L, Mayr J, Fernandez-Rodriguez J, Mirsky E A, et al. Control of type III protein secretion using a minimal genetic system. Nature Communications. 2017; 8:14737.

150. Laemmli U K. Cleavage of Structural Proteins during the Assembly of the Head of Bacteriophage T4. Nature. 1970; 227:680-5.

151. Engler C, Kandzia R, Marillonnet S. A One Pot, One Step, Precision Cloning Method with High Throughput Capability. PLoS ONE. 2008; 3:e3647.

152. Thomason L C, Sawitzke J A, Li X, Costantino N, Court D L. Recombineering: Genetic Engineering in Bacteria Using Homologous Recombination. Current Protocols in Molecular Biology. 2014; 106:1.16.1-1.16.39.

153. Studier F W. Protein production by auto-induction in high density shaking cultures. Protein Expr Purif. 2005; 41:207-34.

156. Kim E, Jakobson C M, Tullman-Ercek D. Engineering transcriptional regulation to control Pdu bacterial micro-compartment formation. PLoS ONE. 2014;

157. Neidhardt F C, Bloch P L, Smith D F. Culture Medium for Enterobacteria Culture Medium for Enterobacteria. 1974; 119.

158. Good N E, Winget G D, Winter W, Connolly T N, Izawa S, Singh R M. Hydrogen ion buffers for biological research. Biochemistry. 1966; 5:467-77.

159. Leysath C E, Monzingo A F, Maynard J A, Barnett J, Georgiou G, Iverson B L, et al. Crystal Structure of the Engineered Neutralizing Antibody M18 Complexed to Domain 4 of the Anthrax Protective Antigen. Journal of Molecular Biology. 2009; 387:680-93.

160. Maynard J A, Maassen C B M, Leppla S H, Brasky K, Patterson J L, Iverson B L, et al. Protection against anthrax toxin by recombinant antibody fragments correlates with antigen affinity. Nature Biotechnology. 2002; 20:597-601.

163. Widmaier D M, Voigt C A. Quantification of the physiochemical constraints on the export of spider silk proteins by *Salmonella* type III secretion. Microbial Cell Factories. 2010; 9:78.

164. Berkowitz D, Hushon J M, Whitfield H J, Roth J, Ames B N. Procedure for identifying nonsense mutations. J Bacteriol. 1968; 96:215-20.

175. Hu J, Worrall L J, Hong C, Vuckovic M, Atkinson C E, Caveney N, et al. Cryo-EM analysis of the T3S injectisome reveals the structure of the needle and open secretin. Nature Communications. 2018; 9:1-11.

181. Metcalf K J. Engineering heterologous protein secretion for improved production. University of California, Berkeley; 2016.

187. Hartman E C, Jakobson C M, Favor A H, Lobba M J, Álvarez-Benedicto E, Francis M B, et al. Quantitative characterization of all single amino acid variants of a viral capsid-based drug delivery vehicle. Nature Communications. 2018; 9:1385.

191. Loquet A, Sgourakis N G, Gupta R, Giller K, Riedel D, Goosmann C, et al. Atomic model of the type III secretion system needle. Nature. 2012; 486:276-9.

192. Buchholz K, Collins J. The roots—a short history of industrial microbiology and biotechnology. Appl Microbiol Biotechnol. 2013; 97:3747-62.

Example 6

The unexpected activation of SPI-1 when different coding sequences were fused to hilD is likely due to increased mRNA stability of the transcript. Adding a foreign DNA sequence to the end of the mRNA could potentially disrupt the native regulation of the hilD transcript due to the 3'UTR. Moreover, these coding sequences are used for protein expression and thus likely to form stable transcripts.

The slightly different effects of the different genomic alterations made in knocking out hilE and transcriptionally fusing reporter proteins to hilD on SPI-1 promoters suggests that combining them may have an additive effect.

As using IPTG on an industrial scale is costly, so we wanted to develop strains that can be used without IPTG induction. In addition, using a plasmid-based system to overexpress hilD would not be optimal. The final strains (ΔhilE, hilD:mCherry and ΔhilE hilD:mCherry) each showed promise as a general strain for bacterial protein secretion of different proteins. Although the reported titers here are lower than the maximum reported titer using synthetic overexpression of hilD, these titers are comparable to those observed with overexpressing hilA from a chemically induced promoter. In addition, the systems introduced here require one less plasmid, opening up the potential for co-expressing other helper factors that can benefit protein production and secretion. Lastly, problems such as plasmid instability, metabolic burden of plasmid maintenance and potential recombination of the plasmid with the native copy on the genome can be avoided with the use of these engineered strains.

Given that there are other layers of control on hilD, it might be possible to increase titer further even more by either further strain engineering or production optimization with process engineering. Specific options include the deletion of FnrS, a sRNA known to inhibit hilD translation [134]; and FliZ, a protein known to bind to HilD and prevents HilD from carrying out its function [155]. Further improvements can also be achieved by tuning environmental factors such as $O_2$ levels and ferric levels that are known to affect HilD levels [73,134]. Combining strain engineering, media optimization and growth optimization will lead to industrially relevant production titers.

Results

Overexpression of hilD Results in Earlier Activation of SPI-1 Promoters

Figure 21:
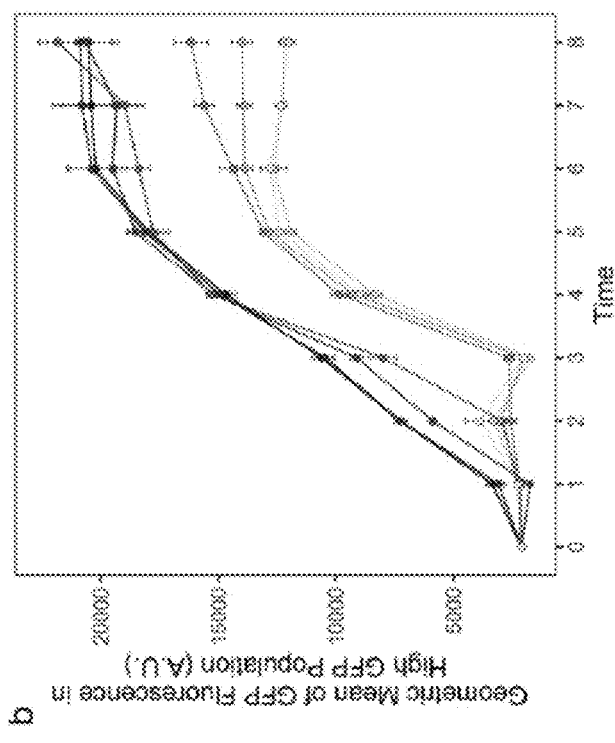
FIG. 21. Plots depicting the percentage of "on" population expressing high GFP under pHilA (a) and the GFP geometric mean of the on population (b) as a function of time. The percentage of "on" population expressing high GFP under all the SPI-1 promoters tested are shown in (a) and the GFP geometric mean of the "on" population in (b). Representative plots can be found in FIG. 22 and FIG. 23. Most of the SPI-1 promoters were highly active after 1 hour when hilD was overexpressed.
Figure 21:
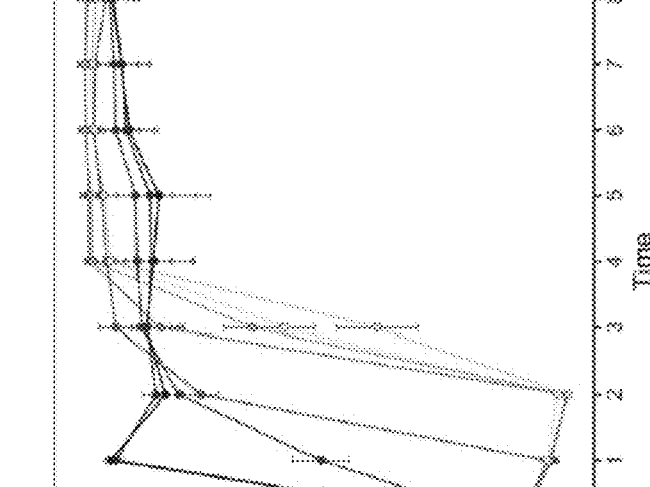
Figure 21:
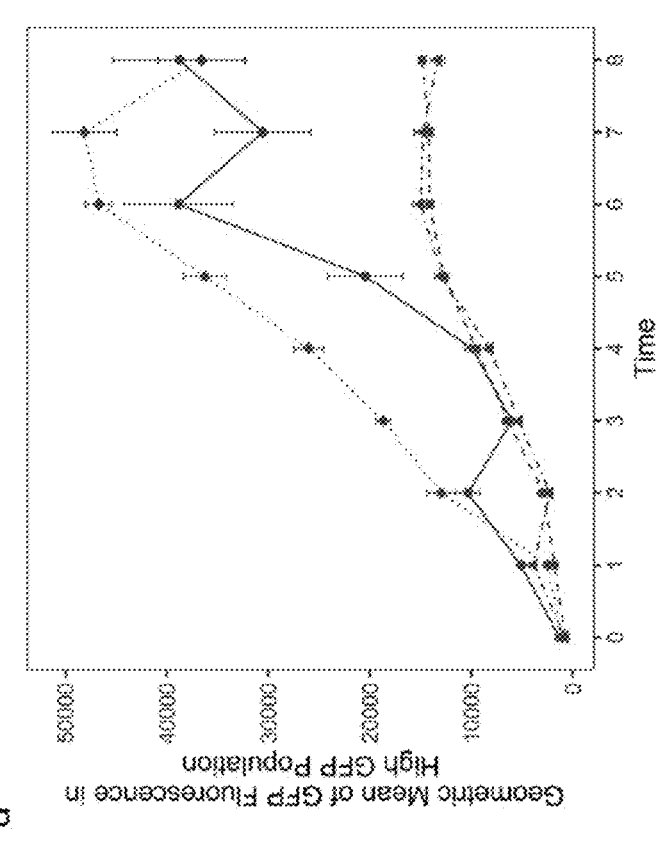
Figure 21:
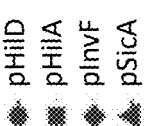
Figure 21:
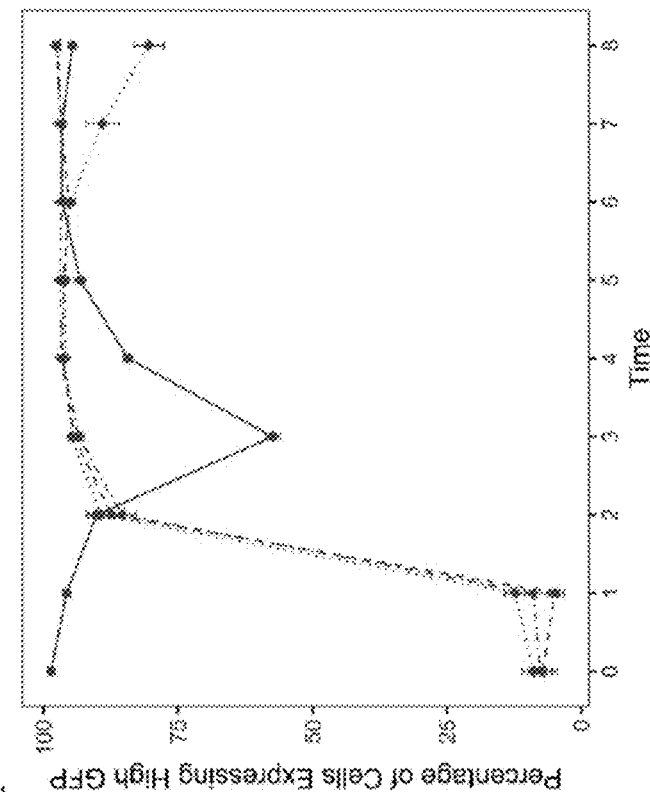

We further wanted to examine the activation of other key promoters in the system—pHilD, pInvF and pSicA—when the plasmid-borne hilD was induced with 100 μM IPTG. As with the pHilA experiment, we used GFPmut2 as the reporter protein and cloned it downstream of each of the three promoters, and then transformed cells harboring pLac hilD with each of these additional plasmids. Flow cytometry was again used to monitor fluorescence as a function of IPTG at various time points. Interestingly, for the two downstream promoters, pInvF and pSicA, more than 90% of the population expressed high levels of GFP after 2 hours (FIG. 21C) compared to previously reported data of 3 hours when overexpressing hilA43. Maximum GFP expression under the different promoters was achieved at 6 hours (FIG. 21D) which was similar to previous reports when overexpressing hilA. The earlier activation of the SPI-1 promoters could result in the higher secretion titer when overexpressing hilD as compared to overexpressing hilA.

Figures 28A, 28B, 28C:
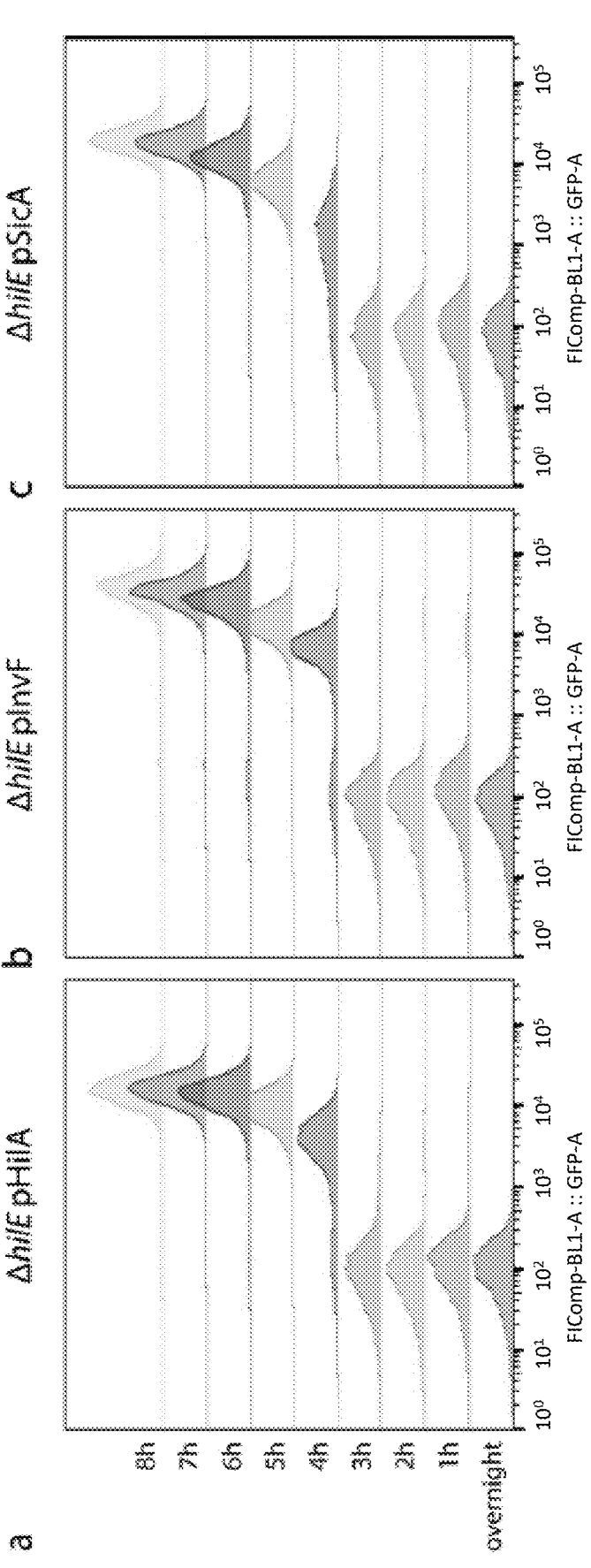
FIGS. 28A-28C. Representative flow plots of different promoters for ΔhilE.

The decrease in percentage of the "on" population for pHilD (FIG. 21C) from 1 to 3 hours was similar to the behavior observed without overexpression of the system (FIG. 28). This could be due to other cellular factors that can modulate the activity of the hill promoter.

Transcriptional Fusions to hilD on the Genome Lead to an Increase in Secretion Titer We reasoned that the use of the plasmid-based system for pHilD was not an accurate representation of the native hilD transcription and constructed a transcriptional fusion of GFPmut2 to hilD on the genome to better capture the native behavior. Before assessing fluorescence, we transformed this strain with our export plasmid to confirm that secretion titer is not affected by our strain engineering.

Unexpectedly, the addition of the GFPmut2 coding sequence after hilD resulted in an increase in secretion (FIG. 25) While this means that the genomic transcriptional fusion of GFPmut2 was also not a reliable measure of the hill transcription, it is a fortuitous finding given that our overall goal is to increase heterologous secretion titer. We hypothesized that changing the DNA sequence found at the 3' end of the hill transcript could be used to modulate the SPI-1 T3SS. We tested this hypothesis by appending DNA sequences of different compositions and lengths after the hill sequence. We chose mCherry, halotag, maltose binding protein (MBP) and the lacZα to transcriptionally fuse to hilD on the genome.

Figure 24A:
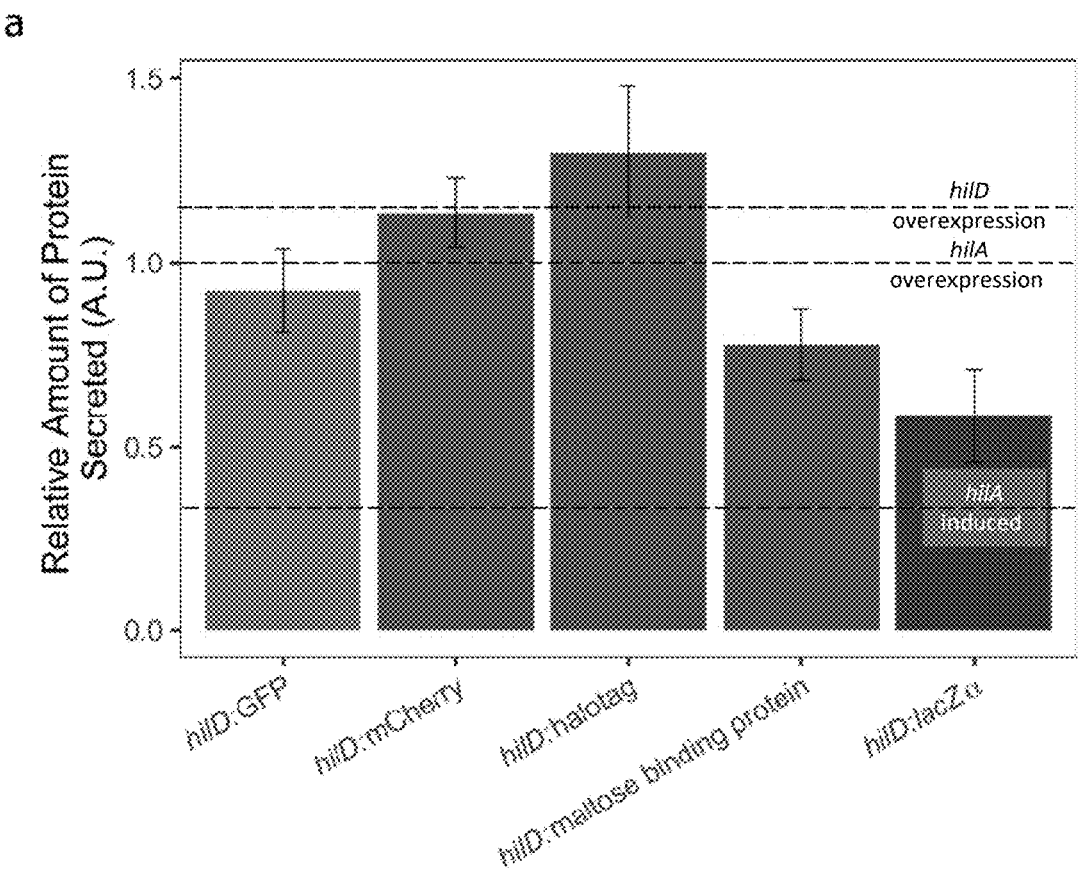
FIGS. 24A-24B. (A) Transcriptionally fusing different protein-encoding sequences led to increases in secretion titer as measured by western blotting. (B) Deleting hilE conferred an increase in secretion titer but not when the hill 3'UTR was deleted. For both plots, results are normalized to the secretion titer obtained by overexpressing hilA off the $P_{lacUV5}$ hilA vector with 100 μM IPTG (gray dashed line). For comparison, a blue dashed line is used to depict the relative secretion titer obtained by overexpressing hilD from a $P_{lacUV5}$ hilD vector with 100 μM IPTG is shown. A purple dashed line is also used to depict the relative secretion titer obtained from ASTE13 harboring the pLac hilA plasmid that had not been induced by IPTG.

The addition of a long DNA sequence (i.e. >700 bp) encoding soluble proteins—GFPmut2 (711 bp), mCherry (711 bp), halotag (894 bp), and MBP (1164 bp) significantly increased secretion and was comparable to the titers achieved by overexpressing hilD with 100 μM IPTG (FIG. 24). The addition of the lacZα sequence, which is much shorter at 270 bp in length, increased secretion titer to a much lower extent (FIG. 24A). The result here indicates that there may be an optimal length of DNA to insert downstream of hilD.

Removing Negative Regulators of HilD can Also Activate the System

Inspired by these results and the low levels of HilD needed to activate the system, we decided to remove existing negative regulators of hilD translation and activity. Our expectation was that this would also increase heterologous secretion to the levels observed with induced, plasmid-borned hilD.

Two important negative regulators of hilD are known—hilE and the 3'UTR of hilD. HilE binds to HilD, preventing the HilD dimer from binding to DNA[69,154]. Thus, by knocking out hilE, we expected increased binding of HilD to its cognate promoters and an overall increase in SPI-1 activation and heterologous secretion.

In contrast, Hfq can bind to the 3'UTR of hilD, preventing its translation[153]. We reasoned that by deleting the 3'UTR responsible for destabilizing the hilD transcript, we would be able to observe a similar increase in heterologous secretion that was observed with the transcriptional fusions in FIG. 24A. Deleting the 3'UTR could have a synergistic effect when combined with transcriptional fusions to the variety of proteins.

Figure 24B:
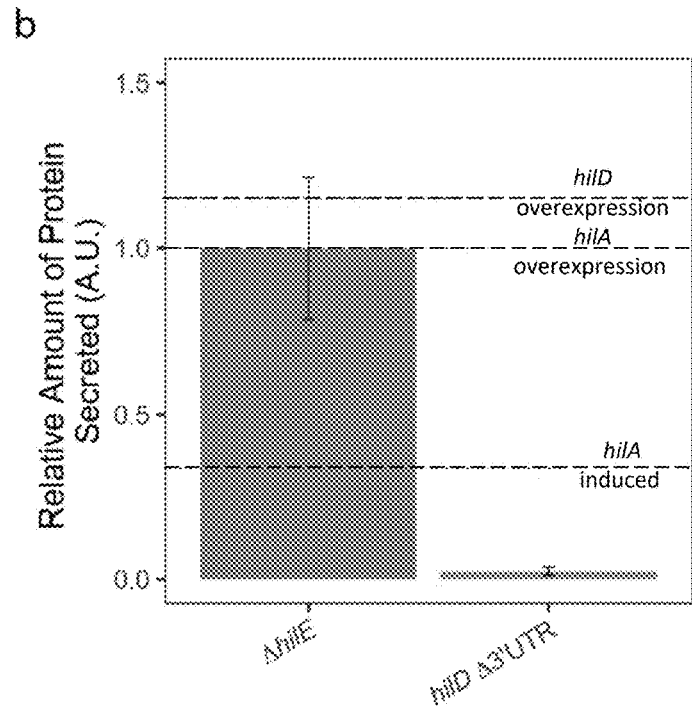

To test these hypotheses, we created two strains: one in which hilE is deleted and another in which the 3'UTR of hilD is deleted. We then transformed these strains with our export plasmid and carried out the secretion assay. Knocking out hilE resulted in secretion titer similar to the synthetic induction of hilI (FIG. 24B). Surprisingly, deleting the hilD 3'UTR resulted in no increase in secretion titer. As hilD is upstream of the operon containing hilA, we suspect that this deletion might be having a polar effect on HilA levels; alternatively, there may be regulation within this section of the transcript that is important for SPI-1 regulation.

Removing Negative Regulators of HilD can Also Activate the System

Inspired by these results and the low levels of HilD needed to activate the system, we decided to remove existing negative regulators of hilD translation and activity. Our expectation was that this would also increase heterologous secretion to the levels observed with induced, plasmid-borned hilD.

Two important negative regulators of hilD are known—hilE and the 3'UTR of hilD. HilE binds to HilD, preventing the HilD dimer from binding to DNA[69,154]. Thus, by knocking out hilE, we expected increased binding of HilD to its cognate promoters and an overall increase in SPI-1 activation and heterologous secretion.

In contrast, Hfq can bind to the 3'UTR of hilD, preventing its translation[153]. We reasoned that by deleting the 3'UTR responsible for destabilizing the hilI transcript, we would be able to observe a similar increase in heterologous secretion that was observed with the transcriptional fusions in FIG. 24A. Deleting the 3'UTR could have a synergistic effect when combined with transcriptional fusions to the variety of proteins.

To test these hypotheses, we created two strains: one in which hilE is deleted and another in which the 3'UTR of hilD is deleted. We then transformed these strains with our export plasmid and carried out the secretion assay. Knocking out hilE resulted in secretion titer similar to the synthetic induction of hilD (FIG. 24B). Surprisingly, deleting the hilI 3'UTR resulted in no increase in secretion titer. As hilD is upstream of the operon containing hilA, we suspect that this deletion might be having a polar effect on HilA levels;

alternatively, there may be regulation within this section of the transcript that is important for SPI-1 regulation.

Genomic Alterations Increased HilD Levels

Figure 25:
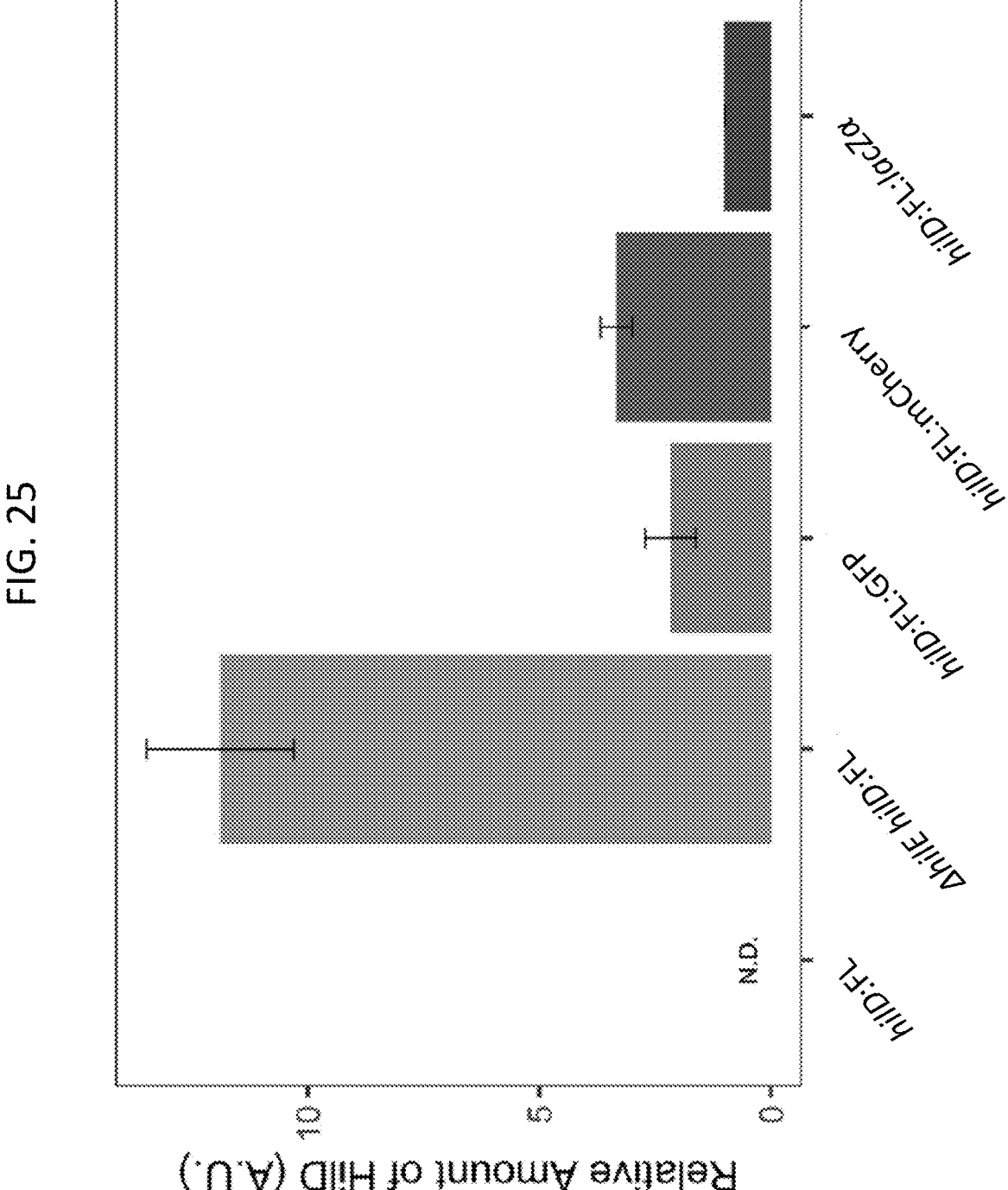
FIG. 25. The different engineered strains had increased HilD levels relative to the hilD:1×FLAG strain. Although knocking out hilE resulted in more HilD, this did not translate to higher secretion titer.

To explore the role of HilD level on secretion titer, we made several of the genomic manipulations described above in the strain harboring hilD:1×FLAG on the genome. Four strains were made—ΔhilE hilD:1×FLAG, hilD:1×FLAG: GFP, hilD:1×FLAG:mCherry, and hilD:1×FLAG:lacZα. HilD levels were determined by western blotting against the FLAG tag. Higher HilD levels were observed in all the engineered strains, and the levels of HilD in ΔhilE hilD:1× FLAG were approximately five times greater than in the hilI transcriptional fusions (FIG. 25). Despite the higher HilD level, knocking out hilE had comparable secretion titers to the other strains (FIG. 24). We hypothesized that the increased HilD levels observed in hilD:1×FLAG:mCherry, and hilD:1×FLAG:lacZα could be due to the stabilization of the hilD mRNA from the addition of DNA sequences to the 3' end of the transcript.

Genomic Engineering Approaches Turn on Different SPI-1 Promoters Differently

We wanted to determine how the different strain engineering approaches affect the behavior of the different SPI-1 promoters—pHilD, pInvF and pSicA. As GFPmut2 was used as the reporter protein, only hilD:mCherry, hilD:halotag, hilD: MBP and ΔhilE were transformed with the respective promoter fusion plasmids and assayed.

Figure 23:
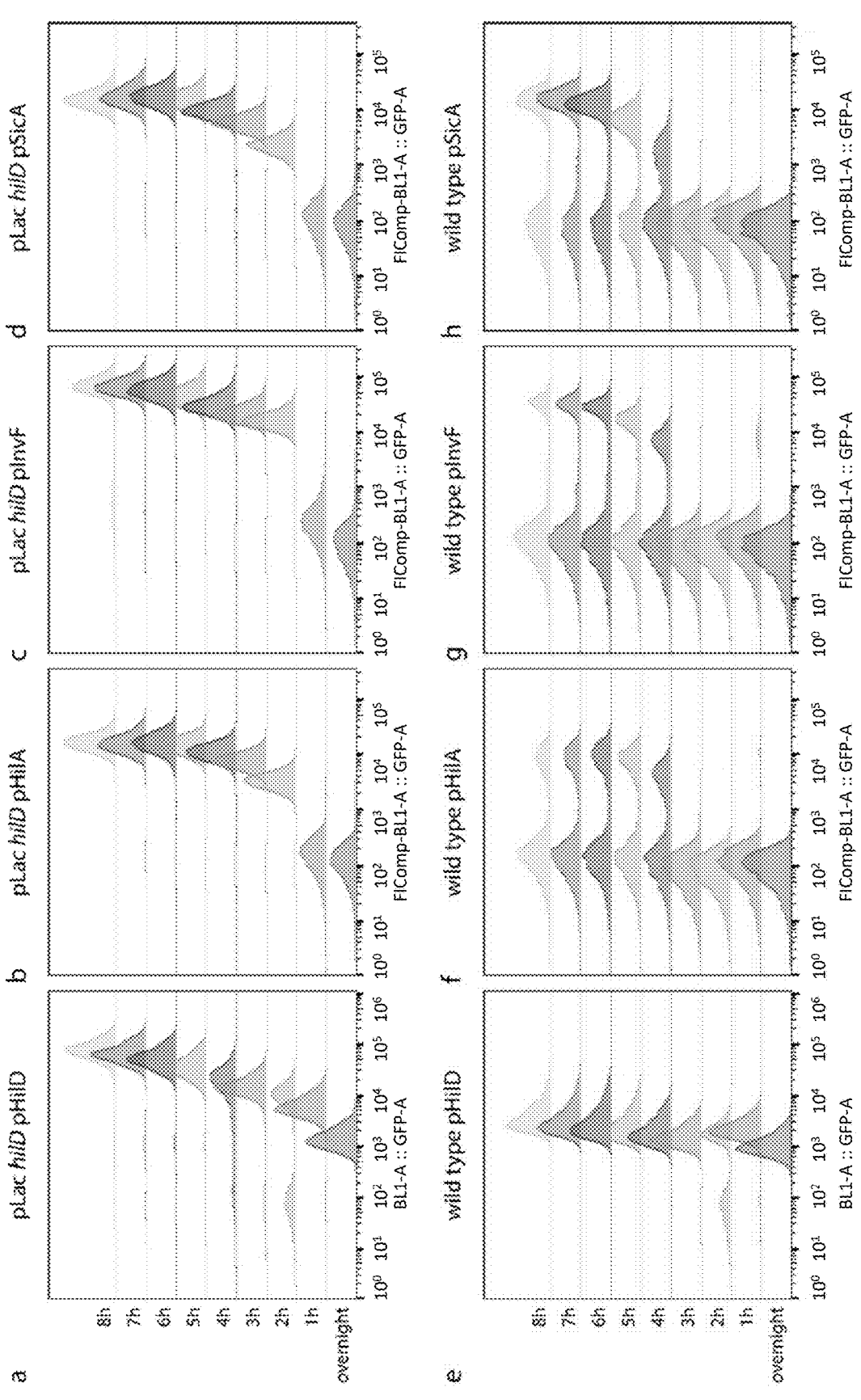
FIG. 23. Representative flow plots for different promoters when hilD is overexpressed. The wild type behavior for each promoter is also included for comparison.
Figure 26:
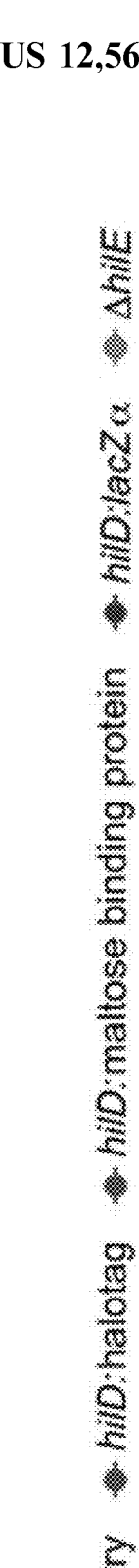
FIG. 26. The percentage of the "on" population expressing high GFP under (a) pHilA, (b) pInvF, and (c) pSicA for the different genomic mutations. The respective GFP geometric mean of each population is shown in (d), (e) and (f) for each of the promoters. Representative plots can be found in FIG. 27 and FIG. 28. The higher percentage of "on" population and higher geometric mean corresponded to increased activation of SPI-1 and thus higher observed titer.
Figure 26:
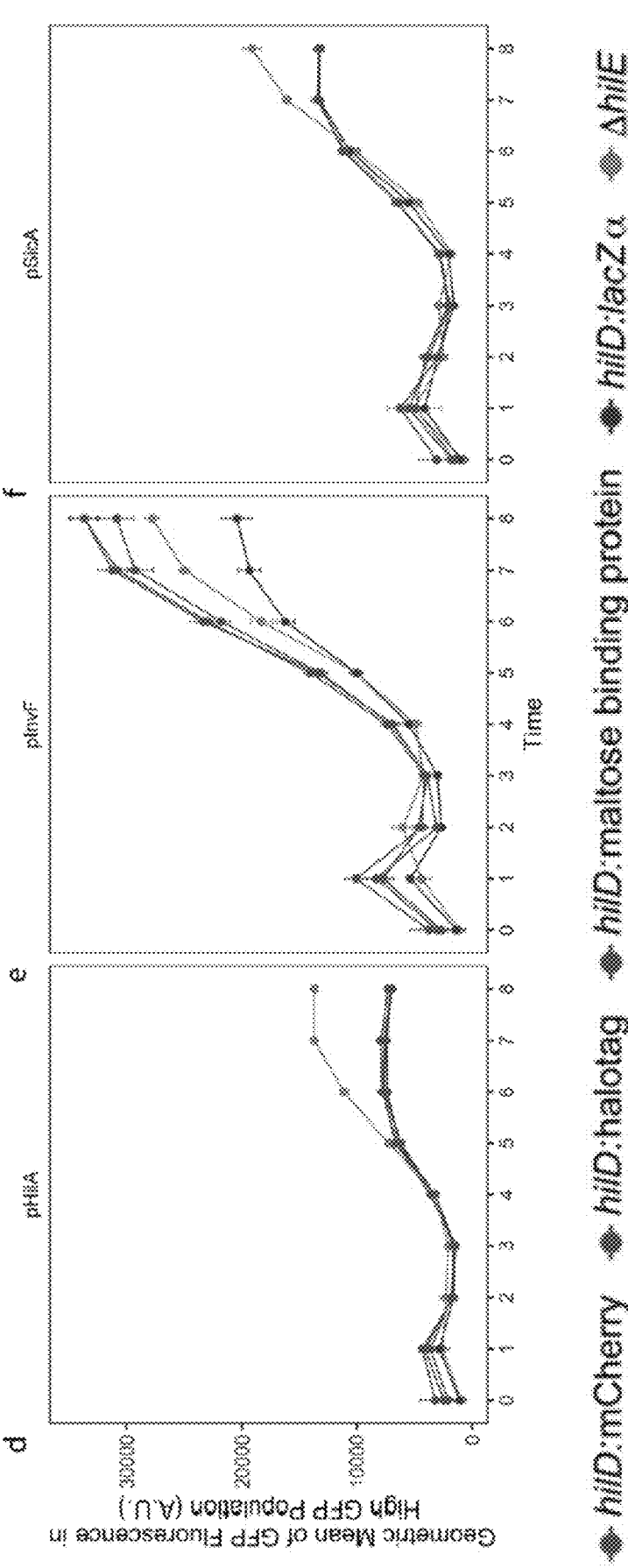
Figure 27:
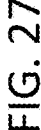
FIG. 27. Representative flow plots of different promoters for each hilD transcriptional fusion.
Figure 27:
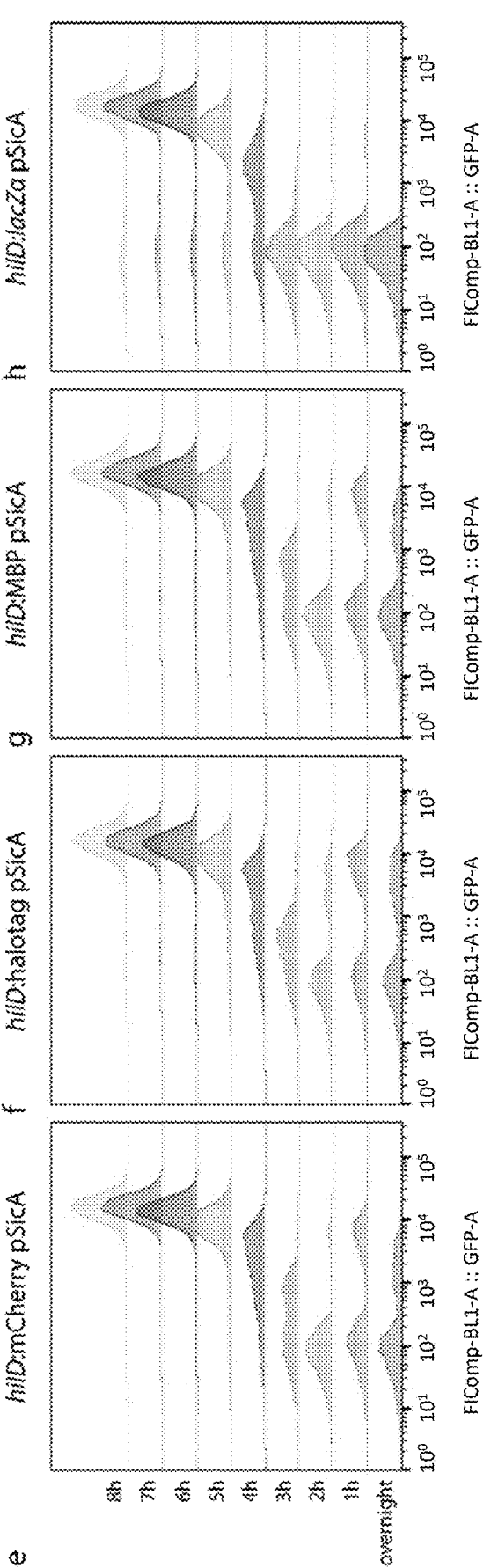

There was a higher background activation of pHilA, pInvF and pSicA in the strains with long coding sequence transcriptional fusions to hilD, as compared to the background activation in the wild type strain shown in FIG. 23 (FIG. 26). This is surprising as our protocol includes 0.4% glucose in the overnight culture prior to the experiment to repress such residual activity. This could be due to the stabilization of the hilI transcript. The overall temporal activations of the different promoters were largely similar in pattern in all the strains (FIG. 26A-C). There was a smaller percentage of the "on" population turning on for all the promoters in the strains harboring hilD:lacZα, which corresponds to the lower secretion titer observed in FIG. 24 (FIG. 26D-F).

Knocking out hilE resulted in a higher pHilA GFP geometric mean compared to the fluorescence of the strains harboring the hilI transcriptional fusions. The GFP geometric mean conferred by the pHilA GFP reporter for ΔhilE as seen in FIG. 26D was similar to GFP geometric mean of DW01/pLac-hilD at 50 µM IPTG (FIG. 21), suggesting comparable HilD activity in these two conditions. Despite the higher pHilA activity, this did not result in higher pInvF GFP geometric mean; instead, it is slightly lower than that of the long transcriptional fusions (FIG. 26E). Again, knocking out hilE unexpectedly resulted in higher geometric mean conferred by the pSicA GFP reporter compared to the long hilD transcriptional fusions (FIG. 26F). Despite the differences observed in the extent of activation in the different SPI-1 promoters, the secretion titers from strain harboring ΔhilE and the long transcriptional fusions were similar (FIG. 24).

Materials and Methods

Cloning of Various Constructs

The pLac plasmids were cloned using Gibson assembly[159]. hilD insert was prepared using PCR with overlaps flanking the 5' and 3' ends. Insert were then thermocycled with pLac p15a vector linearized by Phusion PCR using standard procedures as described previously. New primers were used to linearize the pLac hilD to add the FLAG tag and then assembled by Gibson assembly. The primers are found in Table 22. 5 µl of the Gibson assembly reaction was then used to transform chemically competent *E. coli* DH10B cells by heat shock. The chemically competent cells were subjected to 20 minutes on ice, followed by 60 seconds at 42° C., 2 minutes on ice and then recovery for 1 hour at 37° C. with 350 µl of SOC media. 50 µl of the transformed cells were plated on LB agar plates with kanamycin. All genes were sequenced-verified by Quintara Inc. (Boston, MA).

Strains, Media, Growth and Harvest of Bacteria

*Salmonella enterica* strains were grown overnight in LB Lennox (Dot Scientific Catalog no. DSL24066-500) with the appropriate antibiotics as per Metcalf 2014 at 37° C. and 225 rpm in 24-well blocks. The overnights were sub-cultured to an OD600 of 0.05 in 24-well blocks for all experiments (Axygen Catalog no. PDW10ML24C). Cells were electrotransformed with the required plasmids.

For secretion assay, cultures were grown for 8 hours at 37° C. and 225 rpm. The overexpression of hilA was induced by 0.1 mM IPTG (Dot Scientific Catalog no. DSI56000-5) at the point of subculture. Antibiotics were added as needed. At the point of harvest, 20 µL of the culture was added to 40 µL of 4× Laemilli buffer for the whole culture lysate (WCL) samples. The blocks were then spun at 4000 g for 10 minutes to collect the supernatant (Sup) fractions. 40 µL of the supernatant was added to 16 µL of 4× Laemilli buffer.

Generation of Strains Used

Genomic modifications made in this study were done using the Court lab recombineering method. Briefly, strains were transformed with pSIM6 and then grown overnight at 30° C., 225 rpm. The cells were then sub-cultured at a 1:100 dilution and grown for ~2 hrs to an OD of 0.4-0.8. The lambda red system was then induced at 42° C. for 15 minutes and then the cultures were cooled in an ice water bath for 10 minutes. The cells were spun down at 4600 g for 3 minutes at 4° C., washed thrice in ddH2O and finally resuspended in 200 µL of ddH2O. 200 ng of DNA products or 5 µL of 10 mM primers were electroporated into 50 µL of cells as needed. The DNA products used in round one of recombineering were generated by Phusion PCR using the TUC01 genomic DNA as a template using the primers in Table 22. The PCR reaction was then cleaned up with the Wizard SV Gel and PCR Clean-up kit (Promega Catalog no. A9282).

For round one of recombineering, the cells were recovered in 350 µL of SOC at 30° C. for an hour and then plated on LB agar plates with 10 µg/L of chloramphenicol. For round two, the cells were recovered in 10 mL of LB Lennox at 37° C. for 4 hours. Serial dilutions of the recovery were then plated on 6% sucrose plates. Patch plating on LB agar plates with 10 µg/mL of chloramphenicol or 30 µg/mL carbenicillin were used to determine successful recombination and loss of pSIM6 plasmid respectively. Colony PCR was then carried out using GoTaq (Promega Catalog no. M3008) to isolate the gene of interest to be Sanger sequence verified by Quintara BioSciences. The verified clones were then electroporated with the relevant plasmids as needed to generate the strains.

Figure 22:
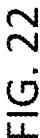
FIG. 22. Representative flow plots for the different levels of hilD induction. The wild type behavior for each promoter is also included for comparison.

The PCR products for inserting the transcriptional fusions into wild type were made with the primers in FIG. 22 with different plasmids using Phusion. To insert the transcriptional fusion into the hilD:1×FLAG background, the primers hilD FL rec F and hilD 3'UTR seq R were used to PCR out each fusion with the previously engineered strains using Phusion.

Western Blotting

Samples were run on a 12.5% SDS PAGE gel at 150V for 60 minutes. 2 µL and 4 µL of samples of WCL and supernatant were loaded respectively. The gels were then equilibrated in Towbin buffer with 20% methanol for 15 minutes. The samples were then transferred to a PVDF membrane (Millipore Catalog no. IPVH00010) using the Owl HEP-1 blotter at 0.3 A for 40 minutes. After which, the membrane was blocked in 5% milk in TBST for 1 hour. The membrane was then decorated with anti-FLAG M2 antibodies from mice (Sigma Catalog no. F3165-1 MG) in 1% milk (1:6666) overnight, followed by three 5-minutes washes in TBST (0.1% Tween-20). The membrane was then decorated with anti-mouse secondary antibody from goat conjugated with HRP (Thermo Fisher Catalog no. 32430) in TBST (1:1000) for 1 hour, followed by three 5-minutes washes in TBST. A different secondary antibody (Jackson ImmunoResearch Catalog no. 515-035-003) was used for the HilD: FLAG blots. Blots were then imaged using SuperSignal West Pico (Thermo Scientific Catalog no. 34080) on the Bio-Rad Chemidoc. The secretion titer was then quantified by densitometry using the Image Lab software v5.2.1 provided by Bio-Rad. The values were then normalized by OD600 and to pLac hilA induced by 100 µM IPTG.

The blots were then striped using the mild stripping protocol modified from Abcam to reprobe for GroEL. The membranes were incubated in mild stripping buffer for 8 minutes twice, washed twice in ddH2O for 10 minutes and then twice in TBST for 5 minutes. The stripped blot was blocked in 5% milk in TBST as above. The membrane was processed as above but using anti-GroEL antibodies from rabbit (Sigma Catalog no. G6532-.5ML) in 1% milk (1:10000) and anti-rabbit secondary from goat conjugated with HRP (Thermo Fisher catalog no. 32460) instead.

Flow Cytometry

The cells were grown overnight in LB Lennox (Dot Scientific Catalog no. DSL24066-500) with the appropriate antibiotics supplemented with 0.4% glucose. The overnight culture was diluted to an OD600 of 0.05 for subculturing and induced according as above. Samples were taken every hour and diluted to an OD of approximately 0.03 in PBS with 2 mg/mL of kanamycin sulfate. The samples were kept overnight at 4° C. and protected from light before running it on the Attune NXT Flow Cytometer (BY) using the autosampler. Data was collected for at least 20 thousand cells and processed with FlowJo v10.5.3. The resulting data was visualized with R and the ggplot2 package.

In order to have a cleaner background to measure the amount of catabolic repression on each strain, there was an additional outgrowth of 3 hours after the first subculture. 150 µL of the first subculture was added to 5 mL of LB-L supplemented with the respective amount of glucose.

TABLE 22

| Primers used in Example 6 Cloning of hilD constructs | |
| --- | --- |
| pLac F GA | TAAAAATGGCGAACCATTAAGGATCC AAACTCGAGTAAGG (SEQ ID NO: 129) |
| pLac R GA | ATTATCCCTTTGTTGATGTTAGATCTT TTGAATTCTGAAATTGTT (SEQ ID NO: 130) |

TABLE 22-continued

Primers used in Example 6 Cloning of hilD constructs

| hilD F GA | TTTCAGAATTCAAAAGATCTAACATC AACAAAGGGATAATATGG (SEQ ID NO: 131) |
|---|---|
| hilD R GA | CCTTACTCGAGTTTGGATCCTTAATG GTTCGCCATTTTTATGA (SEQ ID NO: 132) |
| pLac hilD:FL F GA | GATTATAAAGATGACGATGACAAGT AAGGATCCAAACTCGAGTAAG (SEQ ID NO: 133) |
| pLac hilD:FL R GA | CTTGTCATCGTCATCTTTATAATCATG GTTCGCCATTTTTATGAA (SEQ ID NO: 134) |

Recombineering Round 1 Primers

| hilD:catGsacB F | AACTACGCCATCGACATTCATAAAAA TGGCGAACCATTAATGTGACGGAAG ATCACTTCG (SEQ ID NO: 12) |
|---|---|
| hilD:FLAG catsacB R | AATGGCGAACCATGATTATAAAGATG ACGATGACAAGTAATGTGACGGAAG ATCACTTCG (SEQ ID NO: 135) |
| hilE catsacB F | ACGAAATGGCTGGAAAATGGAACGT TCTTTCATTGTTGGCTGTGACGGAAG ATCACTTCG (SEQ ID NO: 9) |
| hilE catsacB R | GTCCTCATCGCCACAGCGCCTGTCGG TGAAGAGGCCGCCATCAAAGGGAAA ACTGTCCAT (SEQ ID NO: 10) |

Recombineering Round 2 Primers

| hilD 3'UTR KO R | GCCGGCCTTAATCCACAGGGTTAAAG CCGGTTAATGGTTCGCCATTTTTATG AATGTCGA (SEQ ID NO: 136) |
|---|---|
| hilD:FLAG R | TTACTTAAGTGACAGATACAAAAAAT GTTACTTGTCATCGTCATCTTTATAAT CATGGTTCGCCATTTTTATGAATGTC GATGG (SEQ ID NO: 137) |
| hilE KO | ATGGCTGGAAAATGGAACGTTCTTTC ATTGTTGGCGGCGGCCTCTTCACCGA CAGGCGCTGTGGCGATGA (SEQ ID NO: 11) |
| hilD halotag F | AACTACGCCATCGACATTCATAAAAA TGGCGAACCATTAAATTAAAGAGGA GAAAGGTCATGGGATCCGAAATCGG TACTG (SEQ ID NO: 138) |
| hilD halotag R | ATAAAAATCTTTACTTAAGTGACAGA TACAAAAAATGTTAACCGGAAATCTC CAGAGTAG (SEQ ID NO: 139) |
| hilD MBP F | AACTACGCCATCGACATTCATAAAAA TGGCGAACCATTAAATTAAAGAGGA GAAAGGTCATGAAAATCGAAGAAGG TAAACTGGTA (SEQ ID NO: 140) |
| hilD MBP R | TAATAAAAATCTTTACTTAAGTGACA GATACAAAAAATGTTAGTTTTCCTCG ATCCCGAG (SEQ ID NO: 141) |
| hilD lacZalpha F | AACTACGCCATCGACATTCATAAAAA TGGCGAACCATTAAATTAAAGAGGA GAAAGGTCATGACCATGATTACGGAT TCACTG (SEQ ID NO: 142) |
| hilD lacZalpha R | TTAATAAAAATCTTTACTTAAGTGAC AGATACAAAAAATGTTATTCGCCATT CAGGCT (SEQ ID NO: 143) |

TABLE 22-continued

Primers used in Example 6 Cloning of hilD constructs

| hilD FL rec F | AATGGCGAACCATGATTATAAAGATG ACGATGACAAGTAAATTAAAGAGGA GAAAGGTCATG (SEQ ID NO: 144) |
|---|---|

Primers to amplify PCR product for Sanger Sequencing

| hilD 3'UTR seq F | ATCGGCAAGAATGAATCAGG (SEQ ID NO: 145) |
|---|---|
| hilD 3'UTR seq R | CAAGCGTGACTGTTTCGGTA (SEQ ID NO: 146) |
| hilE seq F | TCTATATTCCGATTCGGTGG (SEQ ID NO: 147) |
| hilE seq R | TGTGTTTCATCGCTTTTCC (SEQ ID NO: 148) |

Sanger Sequencing Primers

| hilD 3'UTR int seq F | AGCACGTCCTACTTCATTCAA (SEQ ID NO: 149) |
|---|---|

REFERENCES FOR EXAMPLE 6

69. Kim, K., Palmer, A. D., Vanderpool, C. K. & Slauch, J. M. The Small RNA PinT Contributes to PhoP-Mediated Regulation of the *Salmonella* Pathogenicity Island 1 Type III Secretion System in *Salmonella enterica* Serovar Typhimurium. J. Bacteriol. 201, (2019).

73. Ellermeier, J. R. & Slauch, J. M. Fur Regulates Expression of the *Salmonella* Pathogenicity Island 1 Type III Secretion System through HilD. J. Bacteriol. 190, 476-486 (2008).

134. Kim, K., Golubeva, Y. A., Vanderpool, C. K. & Slauch, J. M. Oxygen-dependent regulation of SPI1 type three secretion system by small RNAs in *Salmonella enterica* serovar Typhimurium. Mol. Microbiol. 111, 570-587 (2019).

153. López-Garrido, J., Puerta-Fernández, E. & Casadesús, J. A eukaryotic-like 3' untranslated region in *Salmonella enterica* hilD mRNA. Nucleic Acids Res. 42, 5894-5906 (2014).

154. Grenz, J. R., Chubiz, J. E. C., Thaprawat, P. & Slauch, J. M. HilE Regulates HilD by Blocking DNA Binding in *Salmonella enterica* Serovar Typhimurium. J. Bacteriol. 200, (2018).

155. Chubiz, J. E. C., Golubeva, Y. A., Lin, D., Miller, L. D. & Slauch, J. M. FliZ Regulates Expression of the *Salmonella* Pathogenicity Island 1 Invasion Locus by Controlling HilD Protein Activity in *Salmonella enterica* Serovar Typhimurium. J. Bacteriol. 192, 6261-6270 (2010).

The invention claimed is:

1. A recombinant *Salmonella* strain having a Type III secretion system (T3SS) comprising
   (a) an insertion of a protein coding sequence between the hilI coding sequence and the hilD 3'UTR suitable to increase hilD expression in the strain; or
   (b) an insertion of a protein coding sequence between the hilI coding sequence and the hilD 3'UTR suitable to increase hilD expression in the strain; and a deletion of hilE;
   wherein the protein coding sequence encodes a B-barrel protein.

2. The recombinant *Salmonella* strain of claim 1, wherein the strain is *enterica* serovar Typhimurium LT2.

3. The recombinant *Salmonella* strain of claim 1, wherein the strain comprises (b).

4. The recombinant *Salmonella* strain of claim 1, wherein the recombinant *Salmonella* strain has at least 4 fold increased secretion titer of a protein of interest by the Type III secretion system as compared to a non-recombinant *Salmonella* strain having a Type III secretion system.

5. The recombinant *Salmonella* strain of claim 1, wherein the strain further comprises at least one modification to reduce the pathogenicity or virulence of the *Salmonella* strain, wherein the at least one modification comprises a deletion of at least one of sipB, sipC, sipD, flhDC, pathogenicity island 4 (SPI-4), and pathogenicity island 5 (SPI-5).

6. The recombinant *Salmonella* strain of claim 1, wherein the protein coding sequence comprises at least 270 base pairs.

7. The recombinant *Salmonella* strain of claim 6, wherein the wherein the protein coding sequence comprises at least 700 base pairs.

8. The recombinant *Salmonella* strain of claim 5, wherein the at least one gene is sipD.

9. The recombinant *Salmonella* strain of claim 3, wherein the strain is a hilE gene knockout.

10. The recombinant *Salmonella* strain of claim 1, wherein the β-barrel protein is a fluorescent protein.

11. An in vitro method of making a heterologous protein of interest, the method comprising
   (a) expressing a heterologous protein of interest in the recombinant *Salmonella* strain of claim 1, wherein the protein of interest is fused to a targeting polypeptide that directs the protein to the Type Ill secretion system (T3SS) of the strain, and wherein the protein of interest is secreted into the medium in which the recombinant *Salmonella* strain is suspended.

12. The in vitro method of claim 11, wherein the method comprises introducing a vector encoding the heterologous protein of interest into the recombinant *Salmonella* strain before (a).

13. The method of claim 11, wherein the targeting polypeptide is an N-terminal secretion tag under control of a promoter that participates in the activation signal cascade for T3SS.

14. The method of claim 11, wherein the heterologous protein of interest comprises a cleavable linker between the targeting polypeptide and the protein of interest.

15. The method of claim 11, wherein the method further comprises
   (b) isolating the heterologous protein of interest from the medium.

16. The method of claim 15, wherein the method further comprises
   (c) contacting the heterologous protein of interest with an enzyme capable of cleaving the protein of interest from the targeting tag.

17. The method of claim 12, wherein only one vector is introduced into the recombinant *Salmonella* strain.

18. The method of claim 11, wherein the recombinant *Salmonella* strain is cultured in a defined medium able to increase protein secretion comprising
   about 10 g/L peptone,
   about 5 g/L yeast extract,
   glycerol or glucose in an amount effective to increase the osmolality of the medium,
   about 80 mM to about 120 mM potassium phosphate pH 7.4; and
   optionally about 150 mM to about 210 mM NaCl.

19. The method of claim 18, wherein the defined medium comprises about 0.4% w/v glycerol.

20. An in vitro culture comprising
   (a) the recombinant *Salmonella* strain of claim 1; and
   (b) defined culture medium for increasing protein secretion comprising:
   about 10 g/L peptone,
   about 5 g/L yeast extract,
   glycerol or glucose in an amount effective to increase the osmolarity of the medium,
   about 80 mM to about 120 mM potassium phosphate pH 7.4, and optionally about 150 mM to about 210 mM NaCl.

21. The in vitro culture of claim 20, wherein the defined medium comprises about 0.2 to about 0.6% w/v glycerol or glucose in an amount effective to increase the osmolarity of the medium.

22. A kit for making a protein of interest comprising (a) the recombinant *Salmonella* strain of claim 1; or (b) an in vitro culture comprising (i) the recombinant *Salmonella* strain of claim 1; and (ii) defined culture medium for increasing protein secretion comprising:

about 10 g/L peptone, about 5 g/L yeast extract, glycerol or glucose in an amount effective to increase the osmolality of the medium, about 80 mM to about 120 mM potassium phosphate pH 7.4; and optionally about 150 mM to about 210 mM NaCl.

\* \* \* \* \*

SEQUENCE LISTING

<160> NUMBER OF SEQ ID NOS: 201

<210> SEQ ID NO 1
<211> LENGTH: 64
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 1
aactacgcca tcgacattca taaaaatggc gaaccattaa attaaagagg agaaaggtca      60
tgag                                                                   64

<210> SEQ ID NO 2
<211> LENGTH: 67
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 2
ttaataaaaa tctttactta agtgacagat acaaaaaatg ttatttgtat agttcatcca      60
tgccatg                                                                67

<210> SEQ ID NO 3
<211> LENGTH: 75
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 3
aactacgcca tcgacattca taaaaatggc gaaccattaa attaaagagg agaaaggtca      60
tggtttccaa gggcg                                                       75

<210> SEQ ID NO 4
<211> LENGTH: 63
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 4
ttaataaaaa tctttactta agtgacagat acaaaaaatg ttatttgtac agctcatcca      60
tgc                                                                    63

<210> SEQ ID NO 5
<211> LENGTH: 35
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 5
aactacgcca tcgacattca taaaaatggc gaacc                                 35

<210> SEQ ID NO 6
<211> LENGTH: 25
<212> TYPE: DNA

-continued

```
<213> ORGANISM: Artificial Sequence
<220> FEATURE:
<223> OTHER INFORMATION: Synthetic- primer for recombineering Salmonella
      strains

<400> SEQUENCE: 6
attaatgtga cggaagatca cttcg                                          25

<210> SEQ ID NO 7
<211> LENGTH: 35
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 7
ataaaaatct ttacttaagt gacagataca aaaaa                               35

<210> SEQ ID NO 8
<211> LENGTH: 25
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 8
tgatcaaagg gaaaactgtc catat                                          25

<210> SEQ ID NO 9
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 9
acgaaatggc tggaaaatgg aacgttcttt cattgttggc tgtgacggaa gatcacttcg    60

<210> SEQ ID NO 10
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 10
gtcctcatcg ccacagcgcc tgtcggtgaa gaggccgcca tcaaagggaa aactgtccat    60

<210> SEQ ID NO 11
<211> LENGTH: 70
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 11
atggctggaa aatggaacgt tctttcattg ttggcggcgg cctcttcacc gacaggcgct    60
gtggcgatga                                                           70

<210> SEQ ID NO 12
<211> LENGTH: 60
```

-continued

```
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 12
aactacgcca tcgacattca taaaaatggc gaaccattaa tgtgacggaa gatcacttcg      60

<210> SEQ ID NO 13
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 13
ataaaaatct ttacttaagt gacagataca aaaaatgatc aaagggaaaa ctgtccatat      60

<210> SEQ ID NO 14
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 14
ttataatttc attacggttt aagtaaagac ttatattcag tgtgacggaa gatcacttcg      60

<210> SEQ ID NO 15
<211> LENGTH: 63
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 15
aagttaaaga tgatattttc ggtgcaggag ctatcatgtg atcaaaggga aaactgtcca      60
tat                                                                    63

<210> SEQ ID NO 16
<211> LENGTH: 70
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 16
tttcattacg gtttaagtaa agacttatat tcagcacatg atagctcctg caccgaaaat      60
atcatcttta                                                             70

<210> SEQ ID NO 17
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 17
aggaattcta atgaagatat catcaggcgc aattaatttt tgtgacggaa gatcacttcg      60
```

<210> SEQ ID NO 18
<211> LENGTH: 63
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 18
tgaggctgga ctacgcccag gccagtggca ggatggatga atcaaaggga aaactgtcca        60
tat                                                                      63

<210> SEQ ID NO 19
<211> LENGTH: 70
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 19
ttctaatgaa gatatcatca ggcgcaatta atttttcatc catcctgcca ctggcctggg        60
cgtagtccag                                                               70

<210> SEQ ID NO 20
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 20
acgtattaaa ttatgcataa tgctctttca attgcttcac tgtgacggaa gatcacttcg        60

<210> SEQ ID NO 21
<211> LENGTH: 63
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 21
taaaaacgct atgcaaatac agagcttcta tcactcagct atcaaaggga aaactgtcca        60
tat                                                                      63

<210> SEQ ID NO 22
<211> LENGTH: 70
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 22
ttaaattatg cataatgctc tttcaattgc ttcacagctg agtgatagaa gctctgtatt        60
tgcatagcgt                                                               70

<210> SEQ ID NO 23
<211> LENGTH: 60
<212> TYPE: DNA
<213> ORGANISM: Artificial Sequence
<220> FEATURE:

-continued

<223> OTHER INFORMATION: Synthetic- primer for recombineering Salmonella
strains

<400> SEQUENCE: 23
ggaaaatatt atgccagtca ctttaagctt cggtaatcat tgtgacggaa gatcacttcg        60

<210> SEQ ID NO 24
<211> LENGTH: 63
<212> TYPE: DNA
<213> ORGANISM: Artificial Sequence
<220> FEATURE:
<223> OTHER INFORMATION: Synthetic- primer for recombineering Salmonella
strains

<400> SEQUENCE: 24
ctgactatct ttatgtcagt aatatattac gactgcaccc atcaaaggga aaactgtcca        60
tat                                                                      63

<210> SEQ ID NO 25
<211> LENGTH: 70
<212> TYPE: DNA
<213> ORGANISM: Artificial Sequence
<220> FEATURE:
<223> OTHER INFORMATION: Synthetic- primer for recombineering Salmonella
strains

<400> SEQUENCE: 25
atattatgcc agtcacttta agcttcggta atcatgggtg cagtcgtaat atattactga        60
cataaagata                                                               70

<210> SEQ ID NO 26
<211> LENGTH: 60
<212> TYPE: DNA
<213> ORGANISM: Artificial Sequence
<220> FEATURE:
<223> OTHER INFORMATION: Synthetic- primer for recombineering Salmonella
strains

<400> SEQUENCE: 26
tttactacca tcaggaggca ttctgaagat acttattcgc tgtgacggaa gatcacttcg        60

<210> SEQ ID NO 27
<211> LENGTH: 63
<212> TYPE: DNA
<213> ORGANISM: Artificial Sequence
<220> FEATURE:
<223> OTHER INFORMATION: Synthetic- primer for recombineering Salmonella
strains

<400> SEQUENCE: 27
gagaactacc gtgactaaca taacactatc cacccagcac atcaaaggga aaactgtcca        60
tat                                                                      63

<210> SEQ ID NO 28
<211> LENGTH: 70
<212> TYPE: DNA
<213> ORGANISM: Artificial Sequence
<220> FEATURE:
<223> OTHER INFORMATION: Synthetic- primer for recombineering Salmonella
strains

<400> SEQUENCE: 28
taccatcagg aggcattctg aagatactta ttcgcgtgct gggtggatag tgttatgtta        60
gtcacggtag                                                               70

```
<210> SEQ ID NO 29
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 29
ggaaagtaaa ttgcaagcac accaggatat tatcgctaat tgtgacggaa gatcacttcg       60

<210> SEQ ID NO 30
<211> LENGTH: 63
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 30
tatgttttta tcagcttgcc gtcgtcataa gcaactgggc atcaaaggga aaactgtcca       60
tat                                                                     63

<210> SEQ ID NO 31
<211> LENGTH: 70
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 31
gtaaattgca agcacaccag gatattatcg ctaatgccca gttgcttatg acgacggcaa       60
gctgataaaa                                                              70

<210> SEQ ID NO 32
<211> LENGTH: 70
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 32
gcttcctgca aggataacag aagaggatat taataatggt tacaagtgta tgtgacggaa       60
gatcacttcg                                                              70

<210> SEQ ID NO 33
<211> LENGTH: 73
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 33
tcaatatcca tattcatcgc atctttcccg gttaattaac gctgcatgtg atcaaaggga       60
aaactgtcca tat                                                          73

<210> SEQ ID NO 34
<211> LENGTH: 100
<212> TYPE: DNA
<213> ORGANISM: Artificial Sequence
```

-continued

```
<220> FEATURE:
<223> OTHER INFORMATION: Synthetic- primer for recombineering Salmonella
      strains

<400> SEQUENCE: 34
cagtacgata agtagcagcc tggaaaccgc caaaagcttc ctgcaaggat aacagaagag      60
gatattaata atggttacaa gtgtacacat gcagcgttaa                          100

<210> SEQ ID NO 35
<211> LENGTH: 100
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 35
caatacaaga ggtgatcact tttttgactc ttgcttcaat atccatattc atcgcatctt      60
tcccggttaa ttaacgctgc atgtgtacac ttgtaaccat                          100

<210> SEQ ID NO 36
<211> LENGTH: 70
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 36
acagagcagc acagtgaaca agaaaaggaa taattatggt aaatgacgca tgtgacggaa      60
gatcacttcg                                                           70

<210> SEQ ID NO 37
<211> LENGTH: 73
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 37
attaacatat ttttctccct ttattttggc agtttttatg cgcgactctg atcaaaggga      60
aaactgtcca tat                                                       73

<210> SEQ ID NO 38
<211> LENGTH: 100
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 38
cgttggtcta tctggaggcg ctaaaaacgg cggagacaga gcagcacagt gaacaagaaa      60
aggaataatt atggtaaatg acgcacagag tcgcgcataa                          100

<210> SEQ ID NO 39
<211> LENGTH: 100
<212> TYPE: DNA
<213> ORGANISM: Artificial Sequence
<220> FEATURE:
<223> OTHER INFORMATION: Synthetic- primer for recombineering Salmonella
      strains
```

<400> SEQUENCE: 39
ttaaataagc ggcgggattt attcccacat tactaattaa catatttttc tccctttatt      60
ttggcagttt ttatgcgcga ctctgtgcgt catttaccat                           100

<210> SEQ ID NO 40
<211> LENGTH: 70
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 40
gcgcataaaa actgccaaaa taaagggaga aaaatatgtt aattagtaat tgtgacggaa      60
gatcacttcg                                                            70

<210> SEQ ID NO 41
<211> LENGTH: 73
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 41
tcacacccat gatggcgtat agatgacctt tcagattaag cgcgaatatt atcaaaggga      60
aaactgtcca tat                                                        73

<210> SEQ ID NO 42
<211> LENGTH: 100
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 42
tgcggatgct tcgcgtttta ttctgcgcca gagtcgcgca taaaaactgc caaaataaag      60
ggagaaaaat atgttaatta gtaataatat tcgcgcttaa                           100

<210> SEQ ID NO 43
<211> LENGTH: 100
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 43
aatatcccca gttcgccatc aggagcgcga ttaaatcaca cccatgatgg cgtatagatg      60
acctttcaga ttaagcgcga atattattac taattaacat                           100

<210> SEQ ID NO 44
<211> LENGTH: 70
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 44
tttaatcgcg ctcctgatgg cgaactgggg atattatgct taatattcaa tgtgacggaa      60

-continued gatcacttcg                                                      70

<210> SEQ ID NO 45
<211> LENGTH: 73
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 45
cttacacttg taaccattat taatatcctc ttctgttatc cttgcaggaa atcaaaggga      60
aaactgtcca tat                                                  73

<210> SEQ ID NO 46
<211> LENGTH: 100
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 46
tctgaaaggt catctatacg ccatcatggg tgtgatttaa tcgcgctcct gatggcgaac      60
tggggatatt atgcttaata ttcaattcct gcaaggataa                    100

<210> SEQ ID NO 47
<211> LENGTH: 100
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 47
tctgcatacc tggcattatg acggggggct gagtccttac acttgtaacc attattaata      60
tcctcttctg ttatccttgc aggaattgaa tattaagcat                    100

<210> SEQ ID NO 48
<211> LENGTH: 87
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 48
tggtctatct ggaggcgcta aaaacggcgg agacagagca gcacagtgaa caagaaaagg      60
aataacagaa gaggatatta ataatgg                                  87

<210> SEQ ID NO 49
<211> LENGTH: 87
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 49
ggtctgcata cctggcatta tgacgggggg ctgagtcctt acacttgtaa ccattattaa      60
tatcctcttc tgttattcct tttcttg                                  87

<210> SEQ ID NO 50

<211> LENGTH: 59
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 50
tgtgtaattc aagggaaatc catgaaacat aaattaatga tgtgacggaa gatcacttc        59

<210> SEQ ID NO 51
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 51 ggatatttt ttatgctgcg tatcgctatt aaggaaatca aagggaaac tgtccatatg        60

<210> SEQ ID NO 52
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 52
aagggaaatc catgaaacat aaattaatga ttccttaata gcgatacgca gcataaaaaa        60

<210> SEQ ID NO 53
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 53
accgtttcgg ttaaacagcc tgttcgatct gttcatccag tgtgacggaa gatcacttcg        60

<210> SEQ ID NO 54
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 54
gtgtaaggcg aatctcagtg ggaggctgcg ttatacgtca tcaaagggaa aactgtccat        60

<210> SEQ ID NO 55
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 55
ttaaacagcc tgttcgatct gttcatccag gacgtataac gcagcctccc actgagattc        60

<210> SEQ ID NO 56
<211> LENGTH: 59

<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 56
gtaatatcag gagacaacat ggaagacgaa agtaatccgt tgtgacggaa gatcacttc        59

<210> SEQ ID NO 57
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 57
tgcgtcacca tgatcaacgt tttcccatga ataaacatca aagggaaaac tgtccatatg        60

<210> SEQ ID NO 58
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 58
gagacaacat ggaagacgaa agtaatccgt gtttattcat gggaaaacgt tgatcatggt        60

<210> SEQ ID NO 59
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 59
cccgatgtgt ctatttattg aagatgtaga ccattctggg tgtgacggaa gatcacttcg        60

<210> SEQ ID NO 60
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 60
tgggaacctt tatgaaaaag tatcttgcat cgccgatca aagggaaaac tgtccatatg        60

<210> SEQ ID NO 61
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 61
ctatttattg aagatgtaga ccattctggg cggcgaatgc aagatacttt ttcataaagg        60

<210> SEQ ID NO 62
<211> LENGTH: 60
<212> TYPE: DNA

<213> ORGANISM: Artificial Sequence
<220> FEATURE:
<223> OTHER INFORMATION: Synthetic- primer for recombineering Salmonella
      strains

<400> SEQUENCE: 62
aatggcagaa cagcgtcgta ctattgaaaa gctgtcttaa tgtgacggaa gatcacttcg      60

<210> SEQ ID NO 63
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 63
gagaaagcag cactataggt atcctgttaa tattaaaatc aaagggaaaa ctgtccatat      60

<210> SEQ ID NO 64
<211> LENGTH: 64
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 64
aatggcagaa cagcgtcgta ctattgaaaa gctgtcttaa attaaagagg agaaaggtca      60
tgag                                                                  64

<210> SEQ ID NO 65
<211> LENGTH: 67
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 65
gtagagaaag cagcactata ggtatcctgt taatattaaa ttatttgtat agttcatcca      60
tgccatg                                                               67

<210> SEQ ID NO 66
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 66
aatgagccca ggccattggt atttcccaag cccactttaa tgtgacggaa gatcacttcg      60

<210> SEQ ID NO 67
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 67
aaggtgttgc cataatgact tccttattta cgttaaaatc aaagggaaaa ctgtccatat      60

<210> SEQ ID NO 68
<211> LENGTH: 64
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 68
aatgagccca ggccattggt atttcccaag cccactttaa attaaagagg agaaaggtca       60
tgag                                                                    64

<210> SEQ ID NO 69
<211> LENGTH: 67
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 69
accaaggtgt tgccataatg acttccttat ttacgttaaa ttatttgtat agttcatcca       60
tgccatg                                                                 67

<210> SEQ ID NO 70
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 70
atccgcactc gctgctatcg caggcaatat tcgcgcttaa tgtgacggaa gatcacttcg       60

<210> SEQ ID NO 71
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 71
aatcacaccc atgatggcgt atagatgacc tttcagaatc aaagggaaaa ctgtccatat       60

<210> SEQ ID NO 72
<211> LENGTH: 64
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 72
atccgcactc gctgctatcg caggcaatat tcgcgcttaa attaaagagg agaaaggtca       60
tgag                                                                    64

<210> SEQ ID NO 73
<211> LENGTH: 67
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 73
ttaaatcaca cccatgatgg cgtatagatg acctttcaga ttatttgtat agttcatcca         60
tgccatg                                                                    67

<210> SEQ ID NO 74
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 74
aaattatggc gagacgtatt ctggtcgtag aagatgaggc tgtgacggaa gatcacttcg         60

<210> SEQ ID NO 75
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 75
ggcattaaaa gcgggtcgaa aaacgatacc ctgtcccgca tcaaagggaa aactgtccat         60

<210> SEQ ID NO 76
<211> LENGTH: 70
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 76
atggcgagac gtattctggt cgtagaagat gaggcgcggg acagggtatc gttttttcgac        60 ccgcttttaa                                                                 70

<210> SEQ ID NO 77
<211> LENGTH: 70
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 77
tttaatcgcg ctcctgatgg cgaactgggg atattatgct taatattcaa tgtgacggaa         60
gatcacttcg                                                                 70

<210> SEQ ID NO 78
<211> LENGTH: 35
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 78
aggtctcagc ttgatatgtt gaccccaact gaaag                                    35

<210> SEQ ID NO 79
<211> LENGTH: 103
<212> TYPE: DNA

-continued

<213> ORGANISM: Artificial Sequence
<220> FEATURE:
<223> OTHER INFORMATION: Synthetic- primer for recombineering Salmonella
      strains

<400> SEQUENCE: 79
aggtctcccg ctggtgatgc ccgccgcgtt cacgtattca tgcagcacca tatgatcccg      60
cgaaccaccc ccagatccac ccccagagtt ctccttctcc cgc                        103

<210> SEQ ID NO 80
<211> LENGTH: 31
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 80
aggtctcagc ttcacccaga aacgctggtg a                                      31

<210> SEQ ID NO 81
<211> LENGTH: 104
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 81
aggtctcccg ctggtgatgc ccgccgcgtt cacgtattca tgcagcacca tatgatcccg      60
cgaaccaccc ccagatccac cccccaatg cttaatcagt gagg                        104

<210> SEQ ID NO 82
<211> LENGTH: 40
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 82
gcagcaaaac cctccgattg tgcgctactg gcggcgtatc                             40

<210> SEQ ID NO 83
<211> LENGTH: 40
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 83
gatacgccgc cagtagcgca caatcggagg gttttgctgc                             40

<210> SEQ ID NO 84
<211> LENGTH: 39
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 84
gcagcaaaac cctccgatga tcgctactgg cggcgtatc                              39

-continued

```
<210> SEQ ID NO 85
<211> LENGTH: 40
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 85
gatacgccgc cagtagcgca tcatcggagg gttttgctgc                            40

<210> SEQ ID NO 86
<211> LENGTH: 40
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 86
gcagcaaaac cctccgatga agcgctactg gcggcgtatc                            40

<210> SEQ ID NO 87
<211> LENGTH: 40
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 87
gatacgccgc cagtagcgct tcatcggagg gttttgctgc                            40

<210> SEQ ID NO 88
<211> LENGTH: 32
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 88
caaaaccctc cgattttgcg ctactggcgg cg                                    32

<210> SEQ ID NO 89
<211> LENGTH: 32
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 89
cgccgccagt agcgcaaaat cggagggttt tg                                    32

<210> SEQ ID NO 90
<211> LENGTH: 31
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 90
caaaaccctc cgatggagcg ctactggcgg c                                     31

<210> SEQ ID NO 91
```

<211> LENGTH: 31
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 91
gccgccagta gcgctccatc ggagggtttt g                                           31

<210> SEQ ID NO 92
<211> LENGTH: 39
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 92
cagcaaaacc ctccgatcat gcgctactgg cggcgtatc                                   39

<210> SEQ ID NO 93
<211> LENGTH: 39
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 93
gatacgccgc cagtagcgca tgatcggagg gttttgctg                                   39

<210> SEQ ID NO 94
<211> LENGTH: 32
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 94
caaaaccctc cgatatagcg ctactggcgg cg                                          32

<210> SEQ ID NO 95
<211> LENGTH: 32
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 95
cgccgccagt agcgctatat cggagggttt tg                                          32

<210> SEQ ID NO 96
<211> LENGTH: 29
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 96
caaaaccctc cgataaggcg ctactggcg                                              29

<210> SEQ ID NO 97
<211> LENGTH: 29

-continued

```
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 97
cgccagtagc gccttatcgg agggttttg                                           29

<210> SEQ ID NO 98
<211> LENGTH: 29
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 98
caaaaccctc cgatttggcg ctactggcg                                           29

<210> SEQ ID NO 99
<211> LENGTH: 29
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 99
cgccagtagc gccaaatcgg agggttttg                                           29

<210> SEQ ID NO 100
<211> LENGTH: 32
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 100
caaaaccctc cgatatggcg ctactggcgg cg                                       32

<210> SEQ ID NO 101
<211> LENGTH: 32
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 101
cgccgccagt agcgccatat cggagggttt tg                                       32

<210> SEQ ID NO 102
<211> LENGTH: 32
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 102
caaaaccctc cgataatgcg ctactggcgg cg                                       32

<210> SEQ ID NO 103
<211> LENGTH: 32
<212> TYPE: DNA
```

<213> ORGANISM: Artificial Sequence
<220> FEATURE:
<223> OTHER INFORMATION: Synthetic- primer for recombineering Salmonella
      strains

<400> SEQUENCE: 103
cgccgccagt agcgcattat cggagggttt tg                                        32

<210> SEQ ID NO 104
<211> LENGTH: 39
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 104
cagcaaaacc ctccgatcaa gcgctactgg cggcgtatc                                 39

<210> SEQ ID NO 105
<211> LENGTH: 39
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 105
gatacgccgc cagtagcgct tgatcggagg gttttgctg                                 39

<210> SEQ ID NO 106
<211> LENGTH: 40
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 106
gcagcaaaac cctccgatag agcgctactg gcggcgtatc                                40

<210> SEQ ID NO 107
<211> LENGTH: 40
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 107
gatacgccgc cagtagcgct ctatcggagg gttttgctgc                                40

<210> SEQ ID NO 108
<211> LENGTH: 40
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 108
gcagcaaaac cctccgatag tgcgctactg gcggcgtatc                                40

<210> SEQ ID NO 109
<211> LENGTH: 40
<212> TYPE: DNA
<213> ORGANISM: Artificial Sequence -continued
<220> FEATURE:
<223> OTHER INFORMATION: Synthetic- primer for recombineering Salmonella
      strains

<400> SEQUENCE: 109
gatacgccgc cagtagcgca ctatcggagg gttttgctgc                              40

<210> SEQ ID NO 110
<211> LENGTH: 40
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 110
gcagcaaaac cctccgatac agcgctactg gcggcgtatc                              40

<210> SEQ ID NO 111
<211> LENGTH: 40
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 111
gatacgccgc cagtagcgct gtatcggagg gttttgctgc                              40

<210> SEQ ID NO 112
<211> LENGTH: 40
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 112
gcagcaaaac cctccgatgt agcgctactg gcggcgtatc                              40

<210> SEQ ID NO 113
<211> LENGTH: 40
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 113
gatacgccgc cagtagcgct acatcggagg gttttgctgc                              40

<210> SEQ ID NO 114
<211> LENGTH: 32
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 114
caaaaccctc cgattgggcg ctactggcgg cg                                     32

<210> SEQ ID NO 115
<211> LENGTH: 32
<212> TYPE: DNA
<213> ORGANISM: Artificial Sequence
<220> FEATURE:

-continued

<223> OTHER INFORMATION: Synthetic- primer for recombineering Salmonella
      strains

<400> SEQUENCE: 115
cgccgccagt agcgcccaat cggagggttt tg                                          32

<210> SEQ ID NO 116
<211> LENGTH: 32
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 116
caaaaccctc cgattatgcg ctactggcgg cg                                          32

<210> SEQ ID NO 117
<211> LENGTH: 32
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 117
cgccgccagt agcgcataat cggagggttt tg                                          32

<210> SEQ ID NO 118
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 118
aacatactgc aggaatatgc taaagtatga ggagagaaaa tgtgacggaa gatcacttcg          60

<210> SEQ ID NO 119
<211> LENGTH: 63
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 119
gcttactttc agatagttct aaaagtaagc tatgttttta atcaaaggga aaactgtcca          60
tat                                                                         63

<210> SEQ ID NO 120
<211> LENGTH: 100
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 120
cttgagtcat ttgtgaatca gcaggaagcg ctcaaaaaca tactgcagga atatgctaaa          60
gtatgaggag agaaaattga ataatttaac gttgtcttcg                                 100

<210> SEQ ID NO 121
<211> LENGTH: 100

<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 121
actttctatc gcggcaaaca aataattata cagaaatagc ttactttcag atagttctaa      60
aagtaagcta tgtttttatt agtggtgatg gtgatgatgc                          100

<210> SEQ ID NO 122
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 122
cccaagccca ctttaattta acgtaaataa ggaagtcatt atggcaacac cttggtcagg      60

<210> SEQ ID NO 123
<211> LENGTH: 64
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 123
ggacaatagt tgcaatcgac ataatccacc ttataactga ttaacggaag ttctgaataa      60
tggc                                                                   64

<210> SEQ ID NO 124
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 124
ctatagtgct gctttctcta cttaacagtg ctcgtttacg tgtgacggaa gatcacttcg      60

<210> SEQ ID NO 125
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 125
gcccttatat tgtttttata acattcactg acttgctata tcaaagggaa aactgtccat      60

<210> SEQ ID NO 126
<211> LENGTH: 70
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 126
ttatattgtt tttataacat tcactgactt gctatcgtaa acgagcactg ttaagtagag      60

```
aaagcagcac                                                       70
```

```
<210> SEQ ID NO 127
<211> LENGTH: 52
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 127
tcgtcggcag cgtcagatgt gtataagaga cagatggcaa caccttggtc ag         52
```

```
<210> SEQ ID NO 128
<211> LENGTH: 58
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 128
gtctcgtggg ctcggagatg tgtataagag acagttaacg gaagttctga ataatggc    58
```

```
<210> SEQ ID NO 129
<211> LENGTH: 40
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 129
taaaaatggc gaaccattaa ggatccaaac tcgagtaagg                        40
```

```
<210> SEQ ID NO 130
<211> LENGTH: 45
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 130
attatccctt tgttgatgtt agatcttttg aattctgaaa ttgtt                  45
```

```
<210> SEQ ID NO 131
<211> LENGTH: 44
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 131
tttcagaatt caaaagatct aacatcaaca aagggataat atgg                   44
```

```
<210> SEQ ID NO 132
<211> LENGTH: 43
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 132
ccttactcga gtttggatcc ttaatggttc gccattttta tga                    43
```

<210> SEQ ID NO 133
<211> LENGTH: 46
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 133
gattataaag atgacgatga caagtaagga tccaaactcg agtaag                         46

<210> SEQ ID NO 134
<211> LENGTH: 45
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 134
cttgtcatcg tcatctttat aatcatggtt cgccattttt atgaa                         45

<210> SEQ ID NO 135
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 135
aatggcgaac catgattata aagatgacga tgacaagtaa tgtgacggaa gatcacttcg        60

<210> SEQ ID NO 136
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 136
gccggcctta atccacaggg ttaaagccgg ttaatggttc gccattttta tgaatgtcga        60

<210> SEQ ID NO 137
<211> LENGTH: 84
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 137
ttacttaagt gacagataca aaaaatgtta cttgtcatcg tcatctttat aatcatggtt        60
cgccattttt atgaatgtcg atgg                                               84

<210> SEQ ID NO 138
<211> LENGTH: 81
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 138
aactacgcca tcgacattca taaaaatggc gaaccattaa attaaagagg agaaaggtca      60
tgggatccga aatcggtact g                                               81

<210> SEQ ID NO 139
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 139
ataaaaatct ttacttaagt gacagataca aaaaatgtta accggaaatc tccagagtag      60

<210> SEQ ID NO 140
<211> LENGTH: 86
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 140
aactacgcca tcgacattca taaaaatggc gaaccattaa attaaagagg agaaaggtca      60
tgaaaatcga agaaggtaaa ctggta                                          86

<210> SEQ ID NO 141
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 141
taataaaaat ctttacttaa gtgacagata caaaaaatgt tagttttcct cgatcccgag      60

<210> SEQ ID NO 142
<211> LENGTH: 83
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 142
aactacgcca tcgacattca taaaaatggc gaaccattaa attaaagagg agaaaggtca      60
tgaccatgat tacggattca ctg                                             83

<210> SEQ ID NO 143
<211> LENGTH: 58
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 143
ttaataaaaa tctttactta agtgacagat acaaaaaatg ttattcgcca ttcaggct      58

<210> SEQ ID NO 144
<211> LENGTH: 62
<212> TYPE: DNA
<213> ORGANISM: Artificial Sequence
<220> FEATURE:

-continued

<223> OTHER INFORMATION: Synthetic- primer for recombineering Salmonella
      strains

<400> SEQUENCE: 144
aatggcgaac catgattata aagatgacga tgacaagtaa attaaagagg agaaaggtca      60
tg                                                                      62

<210> SEQ ID NO 145
<211> LENGTH: 20
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 145
atcggcaaga atgaatcagg                                                   20

<210> SEQ ID NO 146
<211> LENGTH: 20
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 146
caagcgtgac tgtttcggta                                                   20

<210> SEQ ID NO 147
<211> LENGTH: 20
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 147
tctatattcc gattcggtgg                                                   20

<210> SEQ ID NO 148
<211> LENGTH: 19
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 148
tgtgtttcat cgcttttcc                                                    19

<210> SEQ ID NO 149
<211> LENGTH: 21
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 149
agcacgtcct acttcattca a                                                 21

<210> SEQ ID NO 150
<211> LENGTH: 80
<212> TYPE: PRT
<213> ORGANISM: Artificial Sequence
<220> FEATURE:
<223> OTHER INFORMATION: Synthetic- exemplary gene block coding for a
      single amino acid change in PrgI

<400> SEQUENCE: 150

Met Ala Thr Pro Trp Ser Gly Tyr Leu Asp Asp Val Ser Ala Lys Phe
1               5                   10                  15

Asp Thr Gly Val Asp Asn Leu Gln Thr Gln Val Thr Glu Ala Leu Asp
            20                  25                  30

Lys Leu Ala Ala Lys Pro Ser Asp Pro Ala Leu Leu Ala Ala Tyr Gln
        35                  40                  45

Ser Lys Leu Ser Glu Tyr Asn Leu Tyr Arg Asn Ala Gln Ser Asn Thr
    50                  55                  60

Val Lys Val Phe Lys Asp Ile Asp Ala Ala Ile Ile Gln Asn Phe Arg
65                  70                  75                  80

<210> SEQ ID NO 151
<211> LENGTH: 70
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 151
ttatggtaaa tgacgcaagt agcattagcc gtagcgccca gttgcttatg acgacggcaa        60
gctgataaaa                                                              70

<210> SEQ ID NO 152
<211> LENGTH: 59
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 152
ccgcgaagcg gtcgacgtta ccggtggcga acgccgcaaa tgtgacggaa gatcacttc         59

<210> SEQ ID NO 153
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 153
ccacagtagc aactattacc ccagcgccca gaaacaatca aagggaaaac tgtccatatg        60

<210> SEQ ID NO 154
<211> LENGTH: 60
<212> TYPE: DNA
<213> ORGANISM: Artificial Sequence
<220> FEATURE:
<223> OTHER INFORMATION: Synthetic- primer for recombineering Salmonella
      strains

<400> SEQUENCE: 154
gtcgacgtta ccggtggcga acgccgcaaa tgtttctggg cgctggggta atagttgcta        60

<210> SEQ ID NO 155
<211> LENGTH: 40
<212> TYPE: DNA

```
<213> ORGANISM: Artificial Sequence
<220> FEATURE:
<223> OTHER INFORMATION: synthetic

<400> SEQUENCE: 155
gcagcaaaac cctccgattg tgcgctactg gcggcgtatc                                    40

<210> SEQ ID NO 156
<211> LENGTH: 40
<212> TYPE: DNA
<213> ORGANISM: Artificial Sequence
<220> FEATURE:
<223> OTHER INFORMATION: synthetic

<400> SEQUENCE: 156
gatacgccgc cagtagcgca caatcggagg gttttgctgc                                    40

<210> SEQ ID NO 157
<211> LENGTH: 39
<212> TYPE: DNA
<213> ORGANISM: Artificial Sequence
<220> FEATURE:
<223> OTHER INFORMATION: synthetic

<400> SEQUENCE: 157
gcagcaaaac cctccgatga tcgctactgg cggcgtatc                                     39

<210> SEQ ID NO 158
<211> LENGTH: 40
<212> TYPE: DNA
<213> ORGANISM: Artificial Sequence
<220> FEATURE:
<223> OTHER INFORMATION: synthetic

<400> SEQUENCE: 158
gatacgccgc cagtagcgca tcatcggagg gttttgctgc                                    40

<210> SEQ ID NO 159
<211> LENGTH: 40
<212> TYPE: DNA
<213> ORGANISM: Artificial Sequence
<220> FEATURE:
<223> OTHER INFORMATION: synthetic

<400> SEQUENCE: 159
gcagcaaaac cctccgatga agcgctactg gcggcgtatc                                    40

<210> SEQ ID NO 160
<211> LENGTH: 40
<212> TYPE: DNA
<213> ORGANISM: Artificial Sequence
<220> FEATURE:
<223> OTHER INFORMATION: synthetic

<400> SEQUENCE: 160
gatacgccgc cagtagcgct tcatcggagg gttttgctgc                                    40

<210> SEQ ID NO 161
<211> LENGTH: 32
<212> TYPE: DNA
<213> ORGANISM: Artificial Sequence
<220> FEATURE:
<223> OTHER INFORMATION: synthetic

<400> SEQUENCE: 161
caaaaccctc cgattttgcg ctactggcgg cg                                            32
```

```
<210> SEQ ID NO 162
<211> LENGTH: 32
<212> TYPE: DNA
<213> ORGANISM: Artificial Sequence
<220> FEATURE:
<223> OTHER INFORMATION: synthetic

<400> SEQUENCE: 162
cgccgccagt agcgcaaaat cggagggttt tg                               32

<210> SEQ ID NO 163
<211> LENGTH: 31
<212> TYPE: DNA
<213> ORGANISM: Artificial Sequence
<220> FEATURE:
<223> OTHER INFORMATION: synthetic

<400> SEQUENCE: 163
caaaaccctc cgatggagcg ctactggcgg c                               31

<210> SEQ ID NO 164
<211> LENGTH: 31
<212> TYPE: DNA
<213> ORGANISM: Artificial Sequence
<220> FEATURE:
<223> OTHER INFORMATION: synthetic

<400> SEQUENCE: 164
gccgccagta gcgctccatc ggagggtttt g                               31

<210> SEQ ID NO 165
<211> LENGTH: 39
<212> TYPE: DNA
<213> ORGANISM: Artificial Sequence
<220> FEATURE:
<223> OTHER INFORMATION: synthetic

<400> SEQUENCE: 165
cagcaaaacc ctccgatcat gcgctactgg cggcgtatc                       39

<210> SEQ ID NO 166
<211> LENGTH: 39
<212> TYPE: DNA
<213> ORGANISM: Artificial Sequence
<220> FEATURE:
<223> OTHER INFORMATION: synthetic

<400> SEQUENCE: 166
gatacgccgc cagtagcgca tgatcggagg gttttgctg                       39

<210> SEQ ID NO 167
<211> LENGTH: 32
<212> TYPE: DNA
<213> ORGANISM: Artificial Sequence
<220> FEATURE:
<223> OTHER INFORMATION: synthetic

<400> SEQUENCE: 167
caaaaccctc cgatatagcg ctactggcgg cg                              32

<210> SEQ ID NO 168
<211> LENGTH: 32
<212> TYPE: DNA
<213> ORGANISM: Artificial Sequence
<220> FEATURE:
```

-continued

<223> OTHER INFORMATION: synthetic

<400> SEQUENCE: 168
cgccgccagt agcgctatat cggagggttt tg                                    32

<210> SEQ ID NO 169
<211> LENGTH: 29
<212> TYPE: DNA
<213> ORGANISM: Artificial Sequence
<220> FEATURE:
<223> OTHER INFORMATION: synthetic

<400> SEQUENCE: 169
caaaaccctc cgataaggcg ctactggcg                                        29

<210> SEQ ID NO 170
<211> LENGTH: 29
<212> TYPE: DNA
<213> ORGANISM: Artificial Sequence
<220> FEATURE:
<223> OTHER INFORMATION: synthetic

<400> SEQUENCE: 170
cgccagtagc gccttatcgg agggttttg                                        29

<210> SEQ ID NO 171
<211> LENGTH: 29
<212> TYPE: DNA
<213> ORGANISM: Artificial Sequence
<220> FEATURE:
<223> OTHER INFORMATION: synthetic

<400> SEQUENCE: 171
caaaaccctc cgatttggcg ctactggcg                                        29

<210> SEQ ID NO 172
<211> LENGTH: 29
<212> TYPE: DNA
<213> ORGANISM: Artificial Sequence
<220> FEATURE:
<223> OTHER INFORMATION: synthetic

<400> SEQUENCE: 172
cgccagtagc gccaaatcgg agggttttg                                        29

<210> SEQ ID NO 173
<211> LENGTH: 32
<212> TYPE: DNA
<213> ORGANISM: Artificial Sequence
<220> FEATURE:
<223> OTHER INFORMATION: synthetic

<400> SEQUENCE: 173
caaaaccctc cgatatggcg ctactggcgg cg                                    32

<210> SEQ ID NO 174
<211> LENGTH: 32
<212> TYPE: DNA
<213> ORGANISM: Artificial Sequence
<220> FEATURE:
<223> OTHER INFORMATION: synthetic

<400> SEQUENCE: 174
cgccgccagt agcgccatat cggagggttt tg                                    32

```
<210> SEQ ID NO 175
<211> LENGTH: 32
<212> TYPE: DNA
<213> ORGANISM: Artificial Sequence
<220> FEATURE:
<223> OTHER INFORMATION: synthetic

<400> SEQUENCE: 175
caaaaccctc cgataatgcg ctactggcgg cg                                      32

<210> SEQ ID NO 176
<211> LENGTH: 32
<212> TYPE: DNA
<213> ORGANISM: Artificial Sequence
<220> FEATURE:
<223> OTHER INFORMATION: synthetic

<400> SEQUENCE: 176
cgccgccagt agcgcattat cggagggttt tg                                      32

<210> SEQ ID NO 177
<211> LENGTH: 39
<212> TYPE: DNA
<213> ORGANISM: Artificial Sequence
<220> FEATURE:
<223> OTHER INFORMATION: synthetic

<400> SEQUENCE: 177
cagcaaaacc ctccgatcaa gcgctactgg cggcgtatc                               39

<210> SEQ ID NO 178
<211> LENGTH: 39
<212> TYPE: DNA
<213> ORGANISM: Artificial Sequence
<220> FEATURE:
<223> OTHER INFORMATION: synthetic

<400> SEQUENCE: 178
gatacgccgc cagtagcgct tgatcggagg gttttgctg                               39

<210> SEQ ID NO 179
<211> LENGTH: 40
<212> TYPE: DNA
<213> ORGANISM: Artificial Sequence
<220> FEATURE:
<223> OTHER INFORMATION: synthetic

<400> SEQUENCE: 179
gcagcaaaac cctccgatag agcgctactg gcggcgtatc                              40

<210> SEQ ID NO 180
<211> LENGTH: 40
<212> TYPE: DNA
<213> ORGANISM: Artificial Sequence
<220> FEATURE:
<223> OTHER INFORMATION: synthetic

<400> SEQUENCE: 180
gatacgccgc cagtagcgct ctatcggagg gttttgctgc                              40

<210> SEQ ID NO 181
<211> LENGTH: 40
<212> TYPE: DNA
<213> ORGANISM: Artificial Sequence
<220> FEATURE:
<223> OTHER INFORMATION: synthetic
```

-continued

```
<400> SEQUENCE: 181
gcagcaaaac cctccgatag tgcgctactg gcggcgtatc                          40

<210> SEQ ID NO 182
<211> LENGTH: 40
<212> TYPE: DNA
<213> ORGANISM: Artificial Sequence
<220> FEATURE:
<223> OTHER INFORMATION: synthetic

<400> SEQUENCE: 182
gatacgccgc cagtagcgca ctatcggagg gttttgctgc                          40

<210> SEQ ID NO 183
<211> LENGTH: 40
<212> TYPE: DNA
<213> ORGANISM: Artificial Sequence
<220> FEATURE:
<223> OTHER INFORMATION: synthetic

<400> SEQUENCE: 183
gcagcaaaac cctccgatac agcgctactg gcggcgtatc                          40

<210> SEQ ID NO 184
<211> LENGTH: 40
<212> TYPE: DNA
<213> ORGANISM: Artificial Sequence
<220> FEATURE:
<223> OTHER INFORMATION: synthetic

<400> SEQUENCE: 184
gatacgccgc cagtagcgct gtatcggagg gttttgctgc                          40

<210> SEQ ID NO 185
<211> LENGTH: 40
<212> TYPE: DNA
<213> ORGANISM: Artificial Sequence
<220> FEATURE:
<223> OTHER INFORMATION: synthetic

<400> SEQUENCE: 185
gcagcaaaac cctccgatgt agcgctactg gcggcgtatc                          40

<210> SEQ ID NO 186
<211> LENGTH: 40
<212> TYPE: DNA
<213> ORGANISM: Artificial Sequence
<220> FEATURE:
<223> OTHER INFORMATION: synthetic

<400> SEQUENCE: 186
gatacgccgc cagtagcgct acatcggagg gttttgctgc                          40

<210> SEQ ID NO 187
<211> LENGTH: 32
<212> TYPE: DNA
<213> ORGANISM: Artificial Sequence
<220> FEATURE:
<223> OTHER INFORMATION: synthetic

<400> SEQUENCE: 187
caaaaccctc cgattgggcg ctactggcgg cg                                  32

<210> SEQ ID NO 188
<211> LENGTH: 32
```

```
<212> TYPE: DNA
<213> ORGANISM: Artificial Sequence
<220> FEATURE:
<223> OTHER INFORMATION: synthetic

<400> SEQUENCE: 188
cgccgccagt agcgcccaat cggagggttt tg                                   32

<210> SEQ ID NO 189
<211> LENGTH: 32
<212> TYPE: DNA
<213> ORGANISM: Artificial Sequence
<220> FEATURE:
<223> OTHER INFORMATION: synthetic

<400> SEQUENCE: 189
caaaaccctc cgattatgcg ctactggcgg cg                                   32

<210> SEQ ID NO 190
<211> LENGTH: 32
<212> TYPE: DNA
<213> ORGANISM: Artificial Sequence
<220> FEATURE:
<223> OTHER INFORMATION: synthetic

<400> SEQUENCE: 190
cgccgccagt agcgcataat cggagggttt tg                                   32

<210> SEQ ID NO 191
<211> LENGTH: 60
<212> TYPE: DNA
<213> ORGANISM: Artificial Sequence
<220> FEATURE:
<223> OTHER INFORMATION: synthetic

<400> SEQUENCE: 191
aacatactgc aggaatatgc taaagtatga ggagagaaaa tgtgacggaa gatcacttcg     60

<210> SEQ ID NO 192
<211> LENGTH: 63
<212> TYPE: DNA
<213> ORGANISM: Artificial Sequence
<220> FEATURE:
<223> OTHER INFORMATION: synthetic

<400> SEQUENCE: 192
gcttactttc agatagttct aaaagtaagc tatgttttta atcaaaggga aaactgtcca     60
tat                                                                   63

<210> SEQ ID NO 193
<211> LENGTH: 100
<212> TYPE: DNA
<213> ORGANISM: Artificial Sequence
<220> FEATURE:
<223> OTHER INFORMATION: synthetic

<400> SEQUENCE: 193
cttgagtcat ttgtgaatca gcaggaagcg ctcaaaaaca tactgcagga atatgctaaa     60
gtatgaggag agaaaattga ataatttaac gttgtcttcg                          100

<210> SEQ ID NO 194
<211> LENGTH: 100
<212> TYPE: DNA
<213> ORGANISM: Artificial Sequence
<220> FEATURE:
```

-continued

```
<223> OTHER INFORMATION: synthetic

<400> SEQUENCE: 194
actttctatc gcggcaaaca aataattata cagaaatagc ttactttcag atagttctaa      60
aagtaagcta tgtttttatt agtggtgatg gtgatgatgc                           100

<210> SEQ ID NO 195
<211> LENGTH: 60
<212> TYPE: DNA
<213> ORGANISM: Artificial Sequence
<220> FEATURE:
<223> OTHER INFORMATION: synthetic

<400> SEQUENCE: 195
cccaagccca ctttaattta acgtaaataa ggaagtcatt atggcaacac cttggtcagg      60

<210> SEQ ID NO 196
<211> LENGTH: 64
<212> TYPE: DNA
<213> ORGANISM: Artificial Sequence
<220> FEATURE:
<223> OTHER INFORMATION: synthetic

<400> SEQUENCE: 196
ggacaatagt tgcaatcgac ataatccacc ttataactga ttaacggaag ttctgaataa      60
tggc                                                                  64

<210> SEQ ID NO 197
<211> LENGTH: 60
<212> TYPE: DNA
<213> ORGANISM: Artificial Sequence
<220> FEATURE:
<223> OTHER INFORMATION: synthetic

<400> SEQUENCE: 197
ctatagtgct gctttctcta cttaacagtg ctcgtttacg tgtgacggaa gatcacttcg      60

<210> SEQ ID NO 198
<211> LENGTH: 60
<212> TYPE: DNA
<213> ORGANISM: Artificial Sequence
<220> FEATURE:
<223> OTHER INFORMATION: synthetic

<400> SEQUENCE: 198
gcccttatat tgtttttata acattcactg acttgctata tcaaagggaa aactgtccat      60

<210> SEQ ID NO 199
<211> LENGTH: 70
<212> TYPE: DNA
<213> ORGANISM: Artificial Sequence
<220> FEATURE:
<223> OTHER INFORMATION: synthetic

<400> SEQUENCE: 199
ttatattgtt tttataacat tcactgactt gctatcgtaa acgagcactg ttaagtagag      60
aaagcagcac                                                            70

<210> SEQ ID NO 200
<211> LENGTH: 52
<212> TYPE: DNA
<213> ORGANISM: Artificial Sequence
<220> FEATURE:
<223> OTHER INFORMATION: synthetic
```

-continued

```
<400> SEQUENCE: 200
tcgtcggcag cgtcagatgt gtataagaga cagatggcaa caccttggtc ag          52

<210> SEQ ID NO 201
<211> LENGTH: 58
<212> TYPE: DNA
<213> ORGANISM: Artificial Sequence
<220> FEATURE:
<223> OTHER INFORMATION: synthetic

<400> SEQUENCE: 201
gtctcgtggg ctcggagatg tgtataagag acagttaacg gaagttctga ataatggc          58
```